(12) United States Patent
Bagwell et al.

(10) Patent No.: US 11,793,543 B2
(45) Date of Patent: Oct. 24, 2023

(54) DEVICE AND METHOD FOR AUTOMATED INSERTION OF PENETRATING MEMBER

(71) Applicants: Obvius Robotics, Inc., Asheville, NC (US); Baylor College of Medicine, Houston, TX (US)

(72) Inventors: Roger B. Bagwell, Bellefonte, PA (US); Ryan S. Clement, State College, PA (US); Maureen L. Mulvihill, Bellefonte, PA (US); Casey A. Scruggs, Middleburg, PA (US); Kevin A. Snook, State College, PA (US); William E. Cohn, Bellaire, TX (US); James Patrick Herlihy, Houston, TX (US); Kenneth Wayne Rennicks, Pearland, TX (US)

(73) Assignees: Obvius Robotics, Inc., Asheville, NC (US); Baylor College of Medicine, Houston, TX (US)

( * ) Notice: Subject to any disclaimer, the term of this patent is extended or adjusted under 35 U.S.C. 154(b) by 448 days.

(21) Appl. No.: 16/837,675

(22) Filed: Apr. 1, 2020

(65) Prior Publication Data
US 2020/0261113 A1     Aug. 20, 2020

Related U.S. Application Data

(63) Continuation-in-part of application No. 15/267,801, filed on Sep. 16, 2016, now abandoned.
(Continued)

(51) Int. Cl.
*A61B 17/34*          (2006.01)

(52) U.S. Cl.
CPC ...... *A61B 17/3403* (2013.01); *A61B 17/3423* (2013.01); *A61B 2017/3409* (2013.01);
(Continued)

(58) Field of Classification Search
CPC ...... A61M 5/427; A61M 5/3287; A61M 5/46; A61M 25/065; A61M 2205/505;
(Continued)

(56) References Cited

U.S. PATENT DOCUMENTS

| 4,428,748 A | 1/1984 | Peyman |
| 4,527,569 A | 7/1985 | Klob |

(Continued)

FOREIGN PATENT DOCUMENTS

| CA | 2729803 | 1/2010 |
| CA | 2999060 | 3/2017 |

(Continued)

OTHER PUBLICATIONS

American College of Surgeons, Revised Statement on Recommendations for Use of Real-Time Ultrasound Guidance for Placement of Central Venous Catheters, Statements from the college, https://www.facs.org/about-acs/statements/60-real-time-ultrasound#sthash.fTgorRkl.dpuf, online Feb. 1, 2011.

(Continued)

*Primary Examiner* — John Denny Li
(74) *Attorney, Agent, or Firm* — Pandiscio & Pandiscio

(57) ABSTRACT

An automatic insertion device and method of using the same is provided. A vibrator and an extender are connected to a penetrating member and are both in electrical communication with a controller. A detector identifies a subcutaneous target for insertion and the insertion angle, distance and trajectory for the penetrating member are calculated. The vibrator provides vibrations to the penetrating member and the extender advances the penetrating member for insertion. The vibrator and extender are in electrical communication with one another during the insertion process and adjustments to the insertion speed are made based on feedback of vibrational load encountered by the vibrator during inser- (Continued)

tion, and adjustments to the vibrations are made based on feedback of insertion load encountered by the extender during insertion. Iterative samples are taken to constantly adjust the operation of one motor based on the operations and feedback from the other motor.

15 Claims, 28 Drawing Sheets

Related U.S. Application Data

(60) Provisional application No. 62/220,567, filed on Sep. 18, 2015.

(52) U.S. Cl.
CPC .............. *A61B 2017/3413* (2013.01); *A61B 2560/0204* (2013.01); *A61B 2562/0257* (2013.01)

(58) Field of Classification Search
CPC ..... A61B 8/0833; A61B 8/0841; A61B 8/085; A61B 17/3403; A61B 17/3423; A61B 2090/3929; A61B 2017/3409; A61B 2017/3413; A61B 5/150748; A61B 2034/301; A61B 34/10
See application file for complete search history.

(56) References Cited

U.S. PATENT DOCUMENTS

| | | |
|---|---|---|
| 4,553,541 A | 11/1985 | Burns |
| 4,623,335 A | 11/1986 | Jackson |
| 4,648,406 A | 3/1987 | Miller |
| 4,771,660 A | 9/1988 | Yacowitz |
| 4,801,293 A | 1/1989 | Jackson |
| 4,911,161 A | 3/1990 | Schechter |
| 5,024,662 A | 6/1991 | Menes et al. |
| 5,095,910 A | 3/1992 | Powers |
| 5,221,282 A | 6/1993 | Wuchinich |
| 5,320,613 A | 6/1994 | Houge |
| 5,403,276 A | 4/1995 | Schechter et al. |
| 5,449,370 A | 9/1995 | Vaitekunas |
| 5,471,102 A | 11/1995 | Becker et al. |
| 5,526,820 A | 6/1996 | Khoury |
| 5,575,789 A | 11/1996 | Bell et al. |
| 5,647,373 A | 7/1997 | Palteli |
| 5,647,851 A | 7/1997 | Pokras |
| 5,681,283 A | 10/1997 | Brownfield |
| 5,711,302 A | 1/1998 | Lampropoulos |
| 5,728,089 A | 3/1998 | Lal et al. |
| 5,728,130 A | 3/1998 | Ishikawa et al. |
| 5,729,077 A | 3/1998 | Newnham et al. |
| 5,735,813 A | 4/1998 | Lewis |
| 5,769,086 A | 6/1998 | Ritchart |
| 5,840,026 A | 11/1998 | Uber, III et al. |
| 5,865,764 A | 2/1999 | Moorhead |
| 5,871,470 A | 2/1999 | McWha |
| 5,885,226 A | 3/1999 | Rubinstein et al. |
| 5,954,701 A | 9/1999 | Matalon |
| 6,019,775 A | 2/2000 | Sakurai |
| 6,019,776 A | 2/2000 | Preissman et al. |
| 6,068,604 A | 5/2000 | Krause et al. |
| 6,096,004 A | 8/2000 | Meglan et al. |
| 6,190,333 B1 | 2/2001 | Valencia |
| 6,245,028 B1 | 6/2001 | Furst et al. |
| 6,273,861 B1 | 8/2001 | Bates et al. |
| 6,379,371 B1 | 4/2002 | Novak et al. |
| 6,423,014 B1 | 7/2002 | Churchill et al. |
| 6,443,910 B1 | 9/2002 | Krueger et al. |
| 6,465,936 B1 | 10/2002 | Knowles et al. |
| 6,402,769 B1 | 11/2002 | Boukhny |
| 6,491,708 B2 | 12/2002 | Madan et al. |
| 6,497,714 B1 | 12/2002 | Ishikawa et al. |
| 6,623,429 B2 | 1/2003 | Percival |
| 6,514,267 B2 | 2/2003 | Jewett |
| 6,602,229 B2 | 8/2003 | Coss |
| 6,629,922 B1 | 10/2003 | Puria |
| 6,664,712 B2 | 12/2003 | Rayner |
| 6,673,086 B1 | 1/2004 | Hofmeier et al. |
| 6,689,087 B2 | 2/2004 | Pal et al. |
| 6,718,196 B1 | 4/2004 | Mah et al. |
| 6,726,698 B2 | 4/2004 | Cimino |
| 6,730,043 B2 | 5/2004 | Krueger et al. |
| 6,785,572 B2 | 8/2004 | Yanof et al. |
| 6,817,973 B2 | 11/2004 | Merril et al. |
| 6,869,439 B2 | 3/2005 | White et al. |
| 6,939,317 B2 | 9/2005 | Zacharias |
| 6,942,677 B2 | 9/2005 | Nita et al. |
| 6,984,220 B2 | 1/2006 | Wuchinich |
| 7,018,343 B2 | 3/2006 | Plishka |
| 7,025,774 B2 | 4/2006 | Freeman et al. |
| 7,206,626 B2 | 4/2007 | Quaid, III |
| 7,297,131 B2 | 11/2007 | Nita |
| 7,328,064 B2 | 2/2008 | Mathiesen et al. |
| 7,335,997 B2 | 2/2008 | Wiener |
| 7,364,567 B2 | 4/2008 | Beyerlein |
| 7,374,544 B2 | 5/2008 | Freeman et al. |
| 7,518,479 B2 | 4/2009 | Mask et al. |
| 7,585,280 B2 | 9/2009 | Wilson |
| 7,618,409 B2 | 11/2009 | Hochman |
| 7,648,468 B2 | 1/2010 | Boecker et al. |
| 7,651,475 B2 | 1/2010 | Angel et al. |
| 7,651,490 B2 | 1/2010 | Boukhny et al. |
| 7,654,825 B2 | 2/2010 | Ray |
| 7,776,027 B2 | 8/2010 | Manna et al. |
| 7,896,833 B2 | 3/2011 | Hochman |
| 7,922,689 B2 | 4/2011 | Lechner |
| 7,955,301 B1 | 6/2011 | McKay |
| 8,043,229 B2 | 10/2011 | Mulvihill et al. |
| 8,043,308 B2 | 10/2011 | Bittenson |
| 8,075,496 B2 | 12/2011 | Deck |
| 8,142,365 B2 | 3/2012 | Miller |
| 8,177,753 B2 | 5/2012 | Vitullo et al. |
| 8,231,645 B2 | 7/2012 | List |
| 8,308,741 B2 | 11/2012 | Hyde et al. |
| 8,328,738 B2 | 12/2012 | Frankhouser et al. |
| 8,777,871 B2 | 7/2014 | Frankhouser et al. |
| 8,870,865 B2 | 10/2014 | Frankhouser et al. |
| 8,951,195 B2 | 2/2015 | Sheldon et al. |
| 8,992,439 B2 | 3/2015 | Mulvihill et al. |
| 9,220,483 B2 | 12/2015 | Frankhouser et al. |
| 9,408,571 B2 | 8/2016 | Gilgunn et al. |
| 9,420,992 B2 | 8/2016 | Sheldon et al. |
| 9,861,739 B2 | 1/2018 | Sheldon et al. |
| 9,987,468 B2 | 6/2018 | Bagwell et al. |
| 9,999,440 B2 | 6/2018 | Sheldon et al. |
| 10,052,458 B2 | 8/2018 | Fischer et al. |
| 10,219,832 B2 | 3/2019 | Bagwell et al. |
| 2001/0014785 A1 | 8/2001 | Sussman et al. |
| 2002/0010390 A1 | 1/2002 | Guice |
| 2002/0026127 A1 | 2/2002 | Balbierz et al. |
| 2002/0042594 A1 | 4/2002 | Lum |
| 2002/0049462 A1 | 4/2002 | Friedman |
| 2002/0077589 A1 | 6/2002 | Tessari |
| 2002/0109433 A1 | 8/2002 | Rayner |
| 2002/0156376 A1 | 10/2002 | Wang et al. |
| 2002/0183774 A1 | 12/2002 | Witt et al. |
| 2002/0198555 A1 | 12/2002 | White et al. |
| 2003/0040737 A1 | 2/2003 | Merril |
| 2003/0078495 A1 | 4/2003 | Goodwin |
| 2003/0109871 A1 | 6/2003 | Johnson et al. |
| 2003/0195468 A1 | 10/2003 | Lal et al. |
| 2003/0199899 A1 | 10/2003 | Boecker et al. |
| 2003/0199909 A1 | 10/2003 | Boecker |
| 2003/0233046 A1 | 12/2003 | Ferguson |
| 2004/0010204 A1 | 1/2004 | Weber |
| 2004/0010251 A1 | 1/2004 | Pitaru |
| 2004/0024358 A1 | 2/2004 | Meythaler |
| 2004/0049216 A1 | 3/2004 | Verdaasdonk |
| 2004/0059285 A1 | 3/2004 | Mathiesen |
| 2004/0082884 A1 | 4/2004 | Pal |
| 2004/0106894 A1 | 6/2004 | Hunter et al. |

(56) References Cited

U.S. PATENT DOCUMENTS

| | | |
|---|---|---|
| 2004/0215080 A1 | 10/2004 | Lechner |
| 2004/0260240 A1 | 12/2004 | Beyerlein |
| 2005/0070458 A1 | 3/2005 | John |
| 2005/0131345 A1 | 6/2005 | Miller |
| 2005/0148940 A1 | 7/2005 | Miller |
| 2005/0177201 A1 | 8/2005 | Freeman |
| 2006/0058783 A1 | 3/2006 | Buchman, III |
| 2006/0122555 A1 | 6/2006 | Hochman |
| 2006/0129091 A1 | 6/2006 | Bonnette |
| 2006/0135882 A1 | 6/2006 | Bleich |
| 2006/0142657 A1 | 6/2006 | Quaid et al. |
| 2006/0149141 A1 | 7/2006 | Sheets |
| 2006/0149161 A1 | 7/2006 | Wilson |
| 2006/0195043 A1 | 8/2006 | Rutherford |
| 2006/0224144 A1 | 10/2006 | Lee |
| 2007/0038129 A1 | 2/2007 | Kishimoto |
| 2007/0063618 A1 | 3/2007 | Bromfield |
| 2007/0079455 A1 | 4/2007 | Brewer |
| 2007/0088297 A1 | 4/2007 | Redding |
| 2007/0088376 A1 | 4/2007 | Zacharias |
| 2007/0123888 A1 | 5/2007 | Bleich |
| 2007/0129628 A1 | 6/2007 | Hirsh |
| 2007/0129732 A1 | 6/2007 | Zacharias |
| 2007/0142766 A1 | 6/2007 | Sundar et al. |
| 2007/0191758 A1 | 8/2007 | Hunter et al. |
| 2007/0219496 A1 | 9/2007 | Kamen et al. |
| 2007/0250113 A1 | 10/2007 | Hegeman et al. |
| 2007/0255220 A1 | 11/2007 | King |
| 2008/0009791 A1 | 1/2008 | Cohen et al. |
| 2008/0021490 A1 | 1/2008 | Briggs et al. |
| 2008/0031413 A1* | 2/2008 | Bouvier ............... A61B 6/4441 378/63 |
| 2008/0055028 A1 | 3/2008 | Mask |
| 2008/0097287 A1 | 4/2008 | Nelson |
| 2008/0103413 A1 | 5/2008 | Cicenas et al. |
| 2008/0139961 A1 | 6/2008 | Slama et al. |
| 2008/0147094 A1 | 6/2008 | Bittenson |
| 2008/0154188 A1 | 6/2008 | Hochman |
| 2008/0228104 A1 | 9/2008 | Uber et al. |
| 2008/0255444 A1 | 10/2008 | Li |
| 2009/0005703 A1 | 1/2009 | Fasciano |
| 2009/0030339 A1 | 1/2009 | Cheng |
| 2009/0069712 A1 | 3/2009 | Mulvihill et al. |
| 2009/0131830 A1 | 5/2009 | Freeman |
| 2009/0131832 A1 | 5/2009 | Sacristan Rock |
| 2009/0157044 A1 | 6/2009 | Liyanagama |
| 2009/0204119 A1 | 8/2009 | Bleich |
| 2009/0240205 A1 | 9/2009 | Wen |
| 2009/0247865 A1 | 10/2009 | Spohn et al. |
| 2009/0270759 A1 | 10/2009 | Wilson |
| 2009/0275823 A1 | 11/2009 | Ayati et al. |
| 2010/0004558 A1 | 1/2010 | Frankhouser |
| 2010/0010505 A1 | 1/2010 | Herlihy et al. |
| 2010/0036245 A1 | 2/2010 | Yu et al. |
| 2010/0036256 A1 | 2/2010 | Boukhny |
| 2010/0069828 A1 | 3/2010 | Steen |
| 2010/0069851 A1 | 3/2010 | Vad |
| 2010/0094143 A1 | 4/2010 | Mahapatra |
| 2010/0094310 A1 | 4/2010 | Waring et al. |
| 2011/0004159 A1 | 1/2011 | Nelson |
| 2011/0125107 A1 | 5/2011 | Slocum |
| 2011/0130758 A9 | 6/2011 | Bleich |
| 2011/0224623 A1 | 9/2011 | Velez Rivera |
| 2011/0298628 A1 | 12/2011 | Vad |
| 2012/0078231 A1 | 3/2012 | Hoshinouchi |
| 2012/0210569 A1 | 8/2012 | Schmitt |
| 2012/0220942 A1 | 8/2012 | Hall |
| 2012/0243488 A1 | 9/2012 | Aviles |
| 2012/0259221 A1 | 10/2012 | Sheldon |
| 2013/0072856 A1 | 3/2013 | Frankhouser et al. |
| 2013/0107569 A1 | 5/2013 | Suganuma |
| 2013/0131502 A1 | 5/2013 | Blavias et al. |
| 2013/0172713 A1 | 7/2013 | Kirschenman |
| 2014/0005667 A1* | 1/2014 | Stulen .................. A61B 34/30 606/45 |
| 2014/0142553 A1 | 5/2014 | Poncon |
| 2014/0221968 A1* | 8/2014 | Ransbury ........... A61B 5/15003 604/506 |
| 2014/0299568 A1 | 10/2014 | Browne |
| 2015/0065916 A1 | 3/2015 | Maguire |
| 2015/0182232 A1 | 7/2015 | Peterson |
| 2015/0216557 A1 | 8/2015 | Mulvihill et al. |
| 2015/0297449 A1 | 10/2015 | Browne |
| 2015/0306358 A1 | 10/2015 | Duffy |
| 2016/0317242 A1 | 11/2016 | Herlihy et al. |
| 2017/0188990 A1* | 7/2017 | Von Allmen ........... A61B 5/153 |
| 2018/0256862 A1 | 9/2018 | Bagwell et al. |
| 2018/0325547 A1 | 11/2018 | Bagwell et al. |
| 2018/0368883 A1 | 12/2018 | Rossa et al. |
| 2020/0261113 A1 | 8/2020 | Bagwell et al. |
| 2021/0045711 A1 | 2/2021 | Brattain et al. |

FOREIGN PATENT DOCUMENTS

| | | |
|---|---|---|
| CA | 2967482 | 11/2017 |
| EP | 0266058 | 5/1988 |
| EP | 1647255 | 4/2006 |
| JP | 9239031 | 9/1997 |
| JP | 2001346874 | 12/2001 |
| JP | 2012035010 | 2/2012 |
| JP | 2013-172549 | 9/2013 |
| JP | WO2015037418 | 3/2015 |
| WO | 2004091693 | 10/2004 |
| WO | 2008086560 | 7/2008 |
| WO | 2008097609 | 8/2008 |
| WO | 2009083600 | 7/2009 |
| WO | 2009092164 | 7/2009 |
| WO | 2009097621 | 8/2009 |
| WO | WO 2010/006335 | 1/2010 |
| WO | WO 2012/109621 | 8/2012 |
| WO | WO 2014/066937 | 5/2014 |

OTHER PUBLICATIONS

Backlund, Brandon H. et al., Ultrasound Guidance for Central Venous Access by Emergency Physicians in Colorado, Western Journal of Emergency Medicine, Sep. 2012, pp. 320-325, vol. XIII, No. 4.

Bernard, Robert W. et al., Subclavian Vein Catheterizations: A Prospective Study: I. Non-Infectious Complications, Annals of Surgery, Feb. 1971, pp. 184-190, vol. 173, No. 2.

CDC, Guidelines for the Prevention of Intravascular Catheter-Related Infections, 2011, http://stacks.cdc.gov/view/cdc/5916/.

Defalque, Ray J., M.D., Percutaneous Catheterization of the Internal Jugular Vein, Anesthesia and Analgesia, Jan.-Feb. 1974, pp. 116-121, vol. 53, No. 1.

Dodge, Kelly L., MD, et al., Use of Ultrasound Guidance Improves Central Venous Catheter Insertion Success Rates Among Junior Residents, Journal of Ultrasound Medicine, 2012, 31:1519-26.

Froehlich, Curt D. et al., Ultrasound-guided central venous catheter placement decreases complications and decreases placement attempts compared with the landmark technique in patients in a pediatric intensive care unit, Crit Care Med, 2009, pp. 1090-1096, vol. 37, No. 3.

Hind, Daniel et al., Ultrasonic locating devices for central venous cannulation: meta-analysis, BMJ, Aug. 16, 2003, pp. 1-7, vol. 327:361.

Krell, Kenneth, MD, Critical care workforce, Crit Care Med, 2008, pp. 1350-1353, vol. 36, No. 4.

McGee David C., M.D et al., Preventing Complications of Central Venous Catheterization, The New England Journal of Medicine, Mar. 20, 2003, pp. 1123-1133, 348;12.

Randolph, Adrienne G. MD, et al., Ultrasound guidance for placement of central venous catheters: A meta-analysis of the literature, Crit Care Med, Dec. 1996, pp. 2053-2058, 24.

Rothschild, Jeffrey M., MD, MPH, Ultrasound Guidance of Central Vein Catheterization, On Making Health Care Safer: A Critical Analysis of Patient Safety Practices. Rockville, MD: AHRQ, Publications; 2001; Chapter 21: 245-255, https://archive.ahrq.gov/clinic/ptsafety/chap21.htm.

(56) References Cited

OTHER PUBLICATIONS

Schweber, Bill, Medical Design, Medical "Vampire" Robot Seeks Human Vein, Inserts Needle, Sucks Blood, Jul. 30, 2020, https://www.machinedesign.com/medical-design/article/21137988/medical-vampire-robot-seeks-human-vein-inserts-needle-sucks-blood.

Seldinger, Sven Ivar, Catheter Replacement of the Needle in Percutaneous Arteriography: A new technique, Acta Radiologica, 1953, pp. 368-376, 39:5.

Sznajder, J. I., et al., Central Vein Catheterization. Failure and Complication Rates by Three Percutaneous Approaches, Arch. Intern. Med., 1986, pp. 259-261, 146.

Visiontech Partners, 2020, Xact Medical Uses Robotics to "Stick" Patients and Wants You to Join Them, http://visiontech-partners.com/blog/xact-medical-uses-robotics-to-stick-patients-and-wants-you-to-join-them/.

Xact Medical, Inc., 2018, https://xactmedical.com/.

Yonei, Akitomo, M.D. et al., Real-time Ultrasonic Guidance for Percutaneous Puncture of the Internal Jugular Vein, Anesthesiology, Jun. 1986, pp. 830-831, vol. 64, No. 6.

Meyer, Jr., R.J., et al., Displacement Amplification of Electroactive Materials Using the Cymbal Flextensional Transducer, Sensors and Actuators A 87 (2001) 157-162.

Podder, T.K., et al., Effects of Velocity Modulation During Surgical Needle Insertion, Proceedings of the 2005 IEEE, Engineering in Medicine and Biology 27th Annual Conference, Sep. 1-4, 2005.

Luis, J., et al., Rectangular Cymbal Arrays for Improved Ultrasonic Transdermal Insulin Delivery, J. Acoust. Soc. Am., vol. 122, Issue 4, Oct. 2007.

Yang, M., et al., "Microneedle Insertion Force Reduction Using Vibratory Actuation", Biomedical Microdevices 6:3, 177-182, 2004.

Zorcolo, et al., Catheter Insertion Simulation With Combined Visual and Haptic Feedback, Center for Advanced Studies, Research and Development in Sardinia 09101 Uta (CA) Italy.

Piccin, et al., "A Robotized Needle Insertion Device for Percutaneous Procedures", Proceedings of IDETC/CIE 2005, 2006 ASME International Design Engineering Technical Conferences and Computers and Information in Engineering Conference, Long Beach, CA, USA, Sep. 24-28, 2005.

Loeffel, et al., Development of an Advanced Injection Device for Highly Viscous Materials, European Cells and Materials, vol. 11, Supp. 1, 2006, p. 51.

Dario, et al., Smart Surgical Tools and Augmenting Devices, IEEE Transactions on Robotics and Automation, vol. 19, No. 5, Oct. 2003, pp. 782-792.

Sonic Drill Could Go Into Space, R&D, Sep. 2000, p. 135.

Goethals, P., Tactile Feedback for Robot Assisted Minimally Invasive Surgery: An Overview, Division PMA, Department of Engineering, K.U. Leuven, Jul. 14, 2008.

Zorcolo, et al., "Catheter Insertion Simulation with Combined Visual and Haptic Feedback", Center for Advanced Studies, Research and Development in Sardinia, 09101 Uta (CA) Italy; Proceedings of The First PHANTOM Users Research Symposium, May 21-22, 1999, Deutsches Krebsfordschungszentrum, Heidelberg, Germany.

Mark V ProVis Angiographic Injection System, Medrad, Inc., Copyright 2006-2010.

Kwon, et al., Realistic Force Reflection in the Spine Biopsy Simulator, IEEE International Conference on Robotics and Automation, 2001. Proceedings 2001 ICRA, May 21-26, 2001, Seoul, Korea 2001, vol. 2, 1358-1363.

R&D 100 Awards Winners Reveal 21st Century Technologies, 38th Annual R&D Awards, R&D Research & Development, Sep. 2000, p. 135.

Silicon-Based Ultrasonic Surgical Actuators, Amit Lal, Member, IEEE; Proceedings of the 20th Annual International Conference of the IEEE Engineering in Medicine and Biology Society, vol. 20, No. 6, 1998, pp. 2785-2790.

Terrett, et al., 3538 Study Assessing the Effectiveness of a Vibrating Dental Syringe Attachment, Pain Management, Oral Pathology, Malodor, and Indices, Mar. 13, 2004.

Hing, et al., Reality-Based Needle Insertion Simulation for Haptic Feedback in Prostate Brachytherapy, Proceedings of the 2006 IEEE International Conference on Robotics and Automation, Orlando, Florida, May 2006.

Hing, et al., Reality-Based Estimation of Needle and Soft-Tissue Interaction for Accurate Haptic Feedback in Prostate Brachytherapy Simulation, Program for Robotics, Intelligent Sensing, and Mechatronics (PRISM) Labaoratory, Drexel University, Philadelphia, PA, Drexel University College of Medicine, Philadelphia, PA.

International Preliminary Report on Patentability for PCT Application No. PCT/AU2008/000019, dated Jul. 21, 2009.

International Search Report for PCT Application No. PCT/US2009/060387, dated May 18, 2010.

International Search Report for PCT Application No. PCT/US2009/056864, dated Apr. 26, 2010.

United States Patent and Trademark Office; Office Action; Office Action from U.S. Appl. No. 13/222,363;copyright and dated Dec. 11, 2014; pp. 1-9; publisher United States Patent and Trademark Office; Published Alexandria, Virginia, USA; copyright and dated Dec. 11, 2014; (9 pages).

United States Patent and Trademark Office; Office Action; Office Action from U.S. Appl. No. 14/329,177; copyright and dated Nov. 18, 2014; pp. 1-19; publisher United States Patent and Trademark Office; Published Alexandria, Virginia, USA; copyright and dated Nov. 18, 2014; copy enclosed (19 pages).

International Searching Authority; International Search Report and Written Opinion of the International Searching Authority;International Application No. PCT/US2014/062099; Patent Cooperation Treaty; pp. 1-10; publisher United States International Searching Authority; Published Alexandria Virginia, US; copyright and mailing date Mar. 11, 2015; copy enclosed (10 pages).

Shin-Ei T, et al., Reduction of Insertion Force of Medical Devices Into Biological Tissues By Vibration, Japanese Journal of Medical Electronics and Biological Engineering, (2001) 39:292-6.

Marx, J.A., et al., The Effect of Vibration on the Needle Dynamics of Sclerotherapy, Australian College of Phlebology, 12th Annual Scientific Meeting, 2008; Gold Coast, Australia.

Huang, Y., et al., A Piezoelectric Vibration-Based Syringe for Reducing Insertion Force, IOP Conference Series: Materials Science and Engineering, 2012, 42:012020.

Khalaji, I., et al., Analysis of Needle-Tissue Friction During Vibration-Assisted Needle Insertion, Intelligent Robots and Systems (IROS), 2013 IEEE/RSJ International Conference on; 2013 Nov. 3-7, 2013, pp. 4099-4104.

Begg, ND, et al., Audible Frequency Vibration of Puncture-Access Medical Devices. Medical Eng Phys 2014; 36:371-7.

Ramasubramanian, MK, et al., Mechanics of a Mosquito Bite With Applications to Microneedle Design. Raleigh, NC 27695-7810, USA, North Carolina State University, 2008.

Mahvash, M., et al., Fast Needle Insertion to Minimize Tissue Deformation and Damage. IEEE International Conference on Robotics and Automation 2009: 3097-102.

Mahvash, M., et al., Mechanics of Dynamic Needle Insertion into a Biological Material. IEEE Trans Biomed Eng 2009.

Van Gerwen, D.J., et al., Needle-Tissue Interaction Forces—A Survey of Experimental Data. Med Eng Phys 2012; 34:665-80.

Yang, M., et al., Microneedle Insertion Force Reduction Using Vibrator Actuation. Biomed Microdevices, 2004, 6:177-182, Kluwer Academic Publishers, The Netherlands.

Cohen, D., This Won't Hurt a Bit. New Scientist, 2002:21.

Kong, XQ, et al., Mosquito Proboscis: An Elegant Biomicroelectromechanical System. Phys Rev E Stat Nonlin Soft Matter Phys 2010, 82:011910.

Chan, K.K., et al., The Mode of Action of Surgical Tissue Removing Devices, IEEE 1985 Ultrasonics Symposium, 1985 Oct. 16-18, 1985, p. 855-9.

Muralidharan, K., Mechanics of Soft Tissue Penetration By a Vibrating Needle, Baltimore, Maryland, University of Maryland Baltimore County, 2007.

International Searching Authority; International Search Report and Written Opinion of the International Searching Authority; International Application No. PCT/US16/41499; Patent Cooperation Treaty;

(56) References Cited

OTHER PUBLICATIONS pp. 1-8; publisher United States International Searching Authority; Published Alexandria, Virginia, US; copyright and dated Oct. 20, 2016; copy enclosed (8 pages).
Castelvecchi, D., This Bite Won't Hurt a Bit—Science News. Science News 2008:11.
Elgezua, et al., Survey on Current State-of-the-Art in Needle Insertion Robots: Open Challenges for Application in Real Surgery, ProCedia CIRP 5 (2013) 94-99, Elsevier, Amsterdam, Netherlands.
United States Patent and Trademark Office; Office Action; Office Action from U.S. Appl. No. 15/205,357; pp. 1-48; publisher United States Patent and Trademark Office;published Alexandria, Virginia, USA; copyright and dated Jun. 22, 2017; copy enclosed (48 pages).
European Patent Office, Communication Pursuant to Article 94(3) EPC, Communication from European Application No. 16847434.4; pp. 1-9, publisher European Patent Office, published Munich Germany, copyright and dated Apr. 17, 2019; copy enclosed (9 pages).
United States Patent and Trademark Office; Office Action; Office Action from U.S. Appl. No. 15/205,357; pp. 1-16; publisher United States Patent and Trademark Office;published Alexandria, Virginia, USA; copyright and dated Dec. 23, 2016; copy enclosed (16 pages).
International Searching Authority; International Search Report and Written Opinion of the International Searching Authority; International Application No. PCT/US16/52228; Patent Cooperation Treaty; pp. 1-9; publisher United States International Searching Authority; Published Alexandria, Virginia, US; copyright and dated Dec. 20, 2016; copy enclosed (9 pages).
Zevallos, N. et al., Toward Robotically Automated Femoral Vascular Access, ArXiv, Jul. 2021.
Cleary, K. et al., Image-Guided Robotic Delivery System for Precise Placement of Therapeutic Agents, JJ. Controlled Release, 2001, vol 74, No. 1, pp. 363-368.
Okazawa, Stephen et al., Hand-Held Steerable Needle Device, IEEE/ASME Transactions on Mechatronics, Jun. 2005, vol 10, Issue 3.
Khalaji, Iman et al., Analysis of needle-tissue friction during vibration-assisted needle insertion, 2013 IEEE/RSJ International Conference on Intelligent Robots and Systems, Nov. 3-7, 2013.
Adebar, Troy K. et al., 3-D Ultrasound-Guided Robotic Needle Steering in Biological Tissue, IEEE Trans Biomed Eng, Dec. 2014, 61(12):2899-2910.

\* cited by examiner

DEVICE AND METHOD FOR AUTOMATED INSERTION OF PENETRATING MEMBER

CROSS-REFERENCE TO RELATED APPLICATIONS

The present application is a continuation-in-part of co-pending U.S. application Ser. No. 15/267,801 filed on Sep. 16, 2016, which claims the benefit of U.S. Provisional Application Ser. No. 62/220,567, filed on Sep. 18, 2015, now expired, the contents of which are incorporated herein by reference in their entireties.

FIELD OF THE INVENTION

The present invention relates generally to devices for penetrating tissues within a body by automated means for the delivery or removal of bodily fluids, tissues, nutrients, medicines, therapies, and for obtaining percutaneous access to body compartments (e.g., vasculature, spinal cavity) for secondary placement of medical devices (e.g., guidewires, catheters).

BACKGROUND

Central venous catheters (CVCs) allow access to the central circulation of medical patients. More than 5 million CVCs are placed each year in the United States. The CVC is a key platform from which to launch a multitude of critical medical interventions for acutely ill patients, and patients requiring major surgeries or procedures. There are over 15 million CVC days per year alone in Intensive Care Units (ICUs) of US hospitals, and 48% of ICU patients have a CVC inserted at some point during their ICU stay. A CVC is also necessary for patients requiring urgent hemodialysis, such as in acute kidney failure, plasma exchange for various immune mediated diseases, multiple forms of chemotherapy for cancer patients, parenteral nutrition for patients whose gastrointestinal tract cannot be used for feeding, and many other medical interventions.

CVC placement has, since the 1950s, been performed using the eponymous technique developed by the Swedish Radiologist Sven-Ivar Seldinger. Using this technique a hollow bore needle, also referred to as an introducer needle, is advanced through a patient's skin and subcutaneous tissue and finally into a central vein, located millimeters to centimeters below the skin surface. The "central veins" are the internal jugular, subclavian, and femoral veins. Once the central vein is entered, a wire is manually place through the hollow bore needle and into the vein. The needle is then removed, and often a plastic co-axial tissue dilator is then run over the wire into the vein, then removed, also over the wire. This dilates the tissue around the wire, and allows smooth passage of a CVC, next placed over the wire and into the vein. Once the CVC is in place, the wire is removed, leaving the CVC in the vein.

Since the original description of the Seldinger technique, the standard guide for where to place the introducer needle through the skin has been the patient's surface anatomy. Veins are usually located, millimeters to centimeters below the skin, in specific relationship to certain surface landmarks like bones or muscles. However, CVC placement failure rates and the rates of serious complications such as arterial puncture, laceration, and pneumothorax or "collapsed lung" using surface anatomy have been reported to be as high as 35%, and 21% respectively, in well-respected studies. These failure rates are attributed to the fact that surface anatomy does not reliably predict the location of the deep central veins for every patient. In 1986, ultrasonography (US) was used to visualize veins below the skin surface and to use such images to more accurately guide the manual placement of CVCs. The use of this technique lowered the failure and complications rate for placement of CVCs to 5-10%. However, the ultrasound guided CVC placement technique requires substantial training and experience to perform reliably. As such, general and cardiovascular surgeons, anesthesiologists, critical care specialists, and interventional radiologists are typically required to place these catheters. Unfortunately, these specialists are often not available for placement of a CVC in the urgent or emergent time frame in which they are frequently required.

Even well trained, experienced providers can fail at the same rates to place a CVC due to factors that are not possible to account for, or are beyond their control, given the current state of insertion technique. Two premier factors are tissue deformity and venous wall deformation. When the introducer needle is pushed through the skin and subcutaneous tissues, the force can cause the central vein target to move from its original position, causing what is referred to as a "needle pass miss." When a needle comes to the venous wall, it can also push the vein into a different position, called "rolling," again causing needle pass miss. Needle pass misses can result in the needle hitting vital structures in the vicinity of the central vein such as arteries, lungs, or nerves and can cause serious complications. The vein wall can also be compressed by the force of the needle, causing the vein to collapse, making it nearly impossible to enter the vessel lumen and usually promoting passage of the needle through the back wall of the vessel, an event referred to as "vein blowing." Vein blowing usually results in bleeding into the peri-venous tissue. Not only is bleeding a notable complication of and by itself, but it disrupts local anatomy usually precluding subsequent successful CVC placement.

Therefore, there has been interest in various alternative systems of CVC placement, including automated systems that any clinician or medical personnel could operate. Such a system could allow more widely available, reliable, and faster placement of a CVC, with lessened chance of complications. To this point, however, most investigation has focused on steerable needles to solve the fundamental challenges of tissue and vessel deformity. However, there has not been a satisfactory automated CVC placement system developed.

SUMMARY

An automated insertion device, system and method is disclosed combining actuated positional guidance for targeted placement with vibration of a penetrating member, such as a needle, for penetrating the skin, subcutaneous tissues and venous wall that mitigates the tissue and vessel wall deformity problems that plague needle insertion. The device and system includes a series of mechanical actuators that direct the path of the penetrating member, or needle, in accordance with a processor that calculates and directs the positioning and path of the needle placement. The various actuators may be automated for action as directed by the processor. Although described as being used for automated insertion of a penetrating member, such as a needle, the same device and system may be used to insert additional medical devices, including guidewires and catheters, within any body cavity, vessel, or compartment.

The insertion device employs the use of a specific vibrating penetrating member. Prior research has demonstrated that vibrating needles during insertion leads to reductions in both puncture and friction forces. This phenomenon is utilized in nature by mosquitos when they vibrate their proboscis to penetrate the skin of their host. The increased needle velocity from oscillation results in decreased tissue deformation, energy absorption, penetration force, and tissue damage. These effects are partly due to the viscoelastic properties of the biological tissue and can be understood through a modified non-linear Kelvin model that captures the force-deformation response of soft tissue. Since internal tissue deformation for viscoelastic bodies is dependent on velocity, increasing the needle insertion speed results in less tissue deformation. The reduced tissue deformation prior to crack extension increases the rate at which energy is released from the crack, and ultimately reduces the force of rupture. The reduction in force and tissue deformation from the increased rate of needle insertion is especially significant in tissues with high water content such as soft tissue. In addition to reducing the forces associated with cutting into tissue, research has also shown that needle oscillation during insertion reduces the frictional forces between the needle and surrounding tissues.

Therefore, adding oscillatory motion, also referred to herein as vibration and/or reciprocating motion, to the needle during insertion can overcome three challenges in advancing the needle tip to the desired location, as compared to the use of a static needle. First, tissue deformation between the skin and the target vein is minimized by the vibration. This tissue deformation and the "pop through" that occurs as the needle tip traverses different tissue layers can cause the target to move relative to the planned path of the needle. Second, the vibrating needle mitigates the rolling of the target vein. Third, the vibrating needle provides additional contrast in an ultrasound image for the user to observe the advancing needle and final placement location. Imaging modes that are particularly sensitive to velocity changes, such as ultrasound with color Doppler overlay, are especially sensitive in detecting vibrated needles.

The system also provides a way to change a target point before deploying the penetrating member. When the target point is changed, the processor recalculates and updates the positional information for the penetrating member, and provides updated adjustment data for the various actuators to perform, so as to align the penetrating member to the new target point. Imaging may be used with the insertion device, so that images of the subdermal area may be visualized and seen by a user. The target point may be selected and updated on the display by a user, for interactive control.

The insertion device may also be handheld for ease of use by a practitioner or user.

In certain embodiments, the automated insertion device includes a vibration assembly and an extension assembly in electrical communication with one another and/or a controller or processor. The vibration assembly includes a vibrational actuator that generates axial vibrations when activated and imparts or transmits these vibrations to a connected penetrating member. The extension assembly includes an extension actuator connected to the penetrating member, either directly or indirectly, which is capable of moving the penetrating member along an insertion axis to insert the penetrating member into target tissue to a desired preselected target. The distance for insertion may be calculated or determined by a controller or processor based on imaging data from a detector, such as an ultrasound probe, that is positioned to detect a subcutaneous target site and provide visualization of or three-dimensional coordinates for the target site. The angle of insertion for the penetrating member may also be adjusted based on the targeting information and/or imaging data on which the targeting information is derived.

In action, the vibrational actuator vibrates the penetrating member axially according to operative parameters for the actuator. While vibration is occurring, the extension actuator advances the penetrating member along the insertion axis by the determined distance to reach the target site. The vibrational actuator and extension actuator operate at initial modes for each by default. During insertion, the load on the vibrational actuator and extension actuator are monitored at intervals, such as every few milliseconds. When the load and/or power consumption of the vibrational actuator or the extension actuator changes by a predetermined value, a control signal may be sent to the other actuator to change its operative parameters to compensate. For instance, the extension actuator may adopt a different operative mode with a faster or slower insertion speed in response to the load on the vibrational actuator. Similarly, a control signal may be sent to the vibrational actuator to change the vibration parameters, such as power, amplitude and/or frequency of oscillation, to adopt a different vibrational mode of higher or lower power, amplitude or frequency in response to the load on the extension actuator. If further deviation from the predetermined values for load and/or power consumption of the vibrational and/or extension actuators occurs, additional signals may be sent to the extension actuator and/or to the vibrational actuator to further adjust the insertion speed and/or vibrations. This may be an increase or decrease in one motor or actuator to compensate for a decrease or increase, respectively, of the other motor or actuator. Each determination of whether the load and/or power consumption deviation of the vibrational or extension actuators has exceeded the predetermined values for each may be based on or compared to the load and/or power consumption levels most recently detected or to initial starting load and/or power consumption levels for each actuator.

Therefore, there may be a number of insertion speeds and modes of operation, which are adjusted automatically throughout the insertion process depending on the load and/or power consumption of the vibrational and/or extensional actuator. The vibrational and extension actuators act collectively, responsively, and automatically to adjust their operative parameters during insertion in response to what the other actuator is experiencing to achieve the most effective and efficient insertion of the penetrating member to a subcutaneous target. This results in avoiding the problems of tissue deformation that previously plagued practitioners.

In this manner, the insertion speed and rate of vibration are not constant throughout the insertion process. Rather, they may be sped up or slowed down based on input from the other motor. When one motor gets "bogged down" (e.g., is consuming increased power beyond a predefined amount as a result of excessive resistance during tissue penetration), the other motor adjusts to compensate. For instance, when the vibrational actuator is vibrating with decreased amplitude, the insertion speed of the extension actuator may be decreased. Conversely, when the penetrating member is vibrating without issue, the extension actuator may operate at full insertion speed. The vibration may also be adjusted based on the action of the extension actuator. When the extension actuator begins to draw too much power, indicating it is meeting with excessive resistance during tissue penetration, this input is conveyed to the vibrational actuator and triggers a change to a more aggressive vibrational mode to assist penetrating denser tissue. This communication between the extension and vibrational actuators, whether it occurs directly or indirectly through the processor, is bidirectional.

The insertion device and method, together with their particular features and advantages, will become more apparent from the following detailed description and with reference to the appended drawings.

DESCRIPTION OF THE DRAWINGS

Like reference numerals refer to like parts throughout the several views of the drawings.

DETAILED DESCRIPTION

As shown in the accompanying drawings, the present invention is directed to an insertion device, system and method that permits subcutaneous access to body cavities, such as blood vessels, for needle insertion and potential placement of guidewires, dilators, catheters such as CVCs, and the like. The device and system includes a plurality of actuators that may be automated for adjusting the position and deploying a penetrating member into the tissue of a subject, such as the skin of a patient. A target point is preselected and used to calculate the position and adjustments to the penetrating member, and the series of actuators are adjusted to control the various components of the device to produce the proper alignment so as to reach the preselected target position upon deployment. The actuators may be adjusted automatically based on calculations made by a processor, and may further be adjusted as the target point location is changed. In at least one embodiment, an image-based modality is used to obtain data on the tissue or cavity to be targeted. The entire device is preferably handheld for ease of use.

Figure 1:
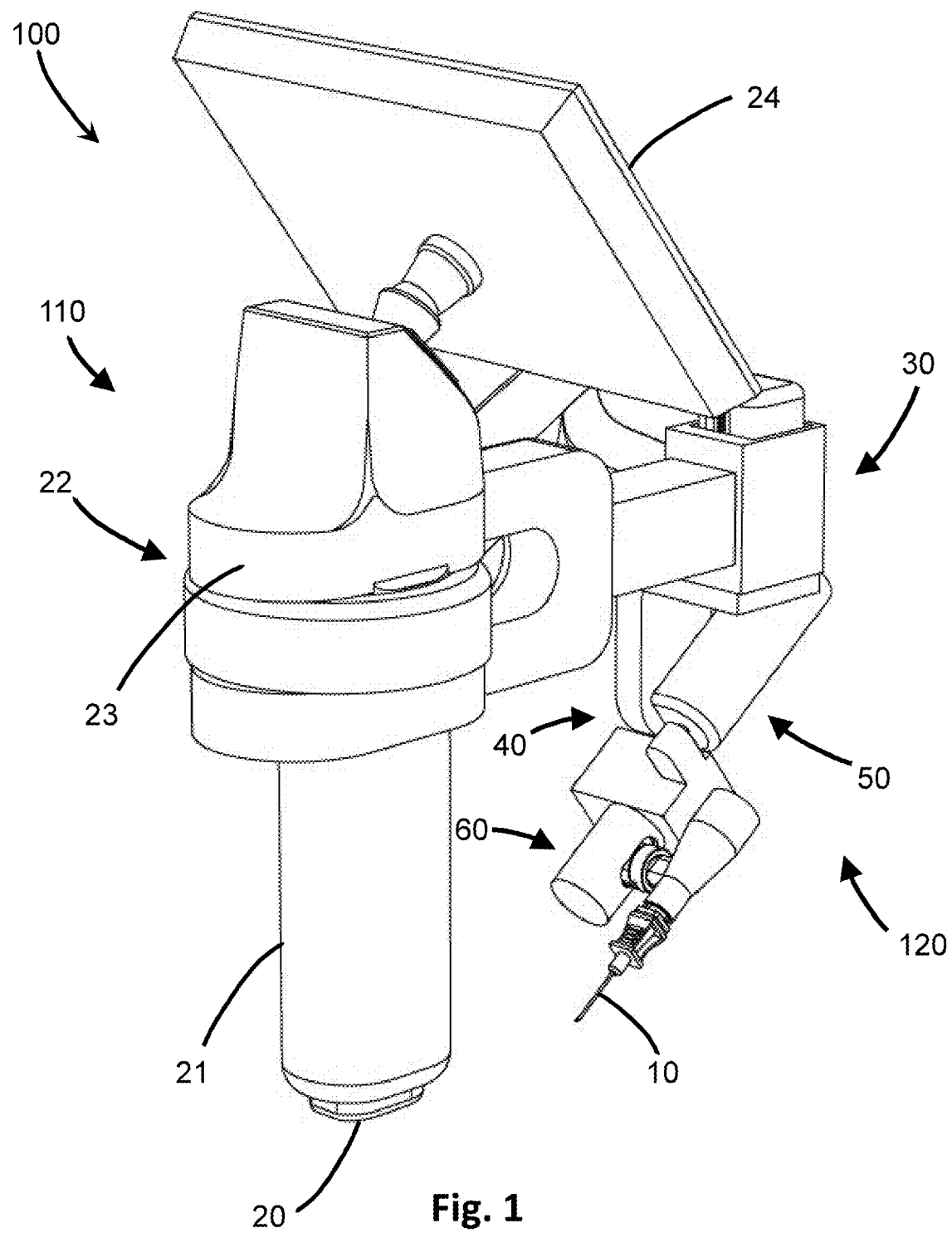
FIG. 1 is a perspective view of one embodiment of the insertion device of the present invention.
Figure 2:
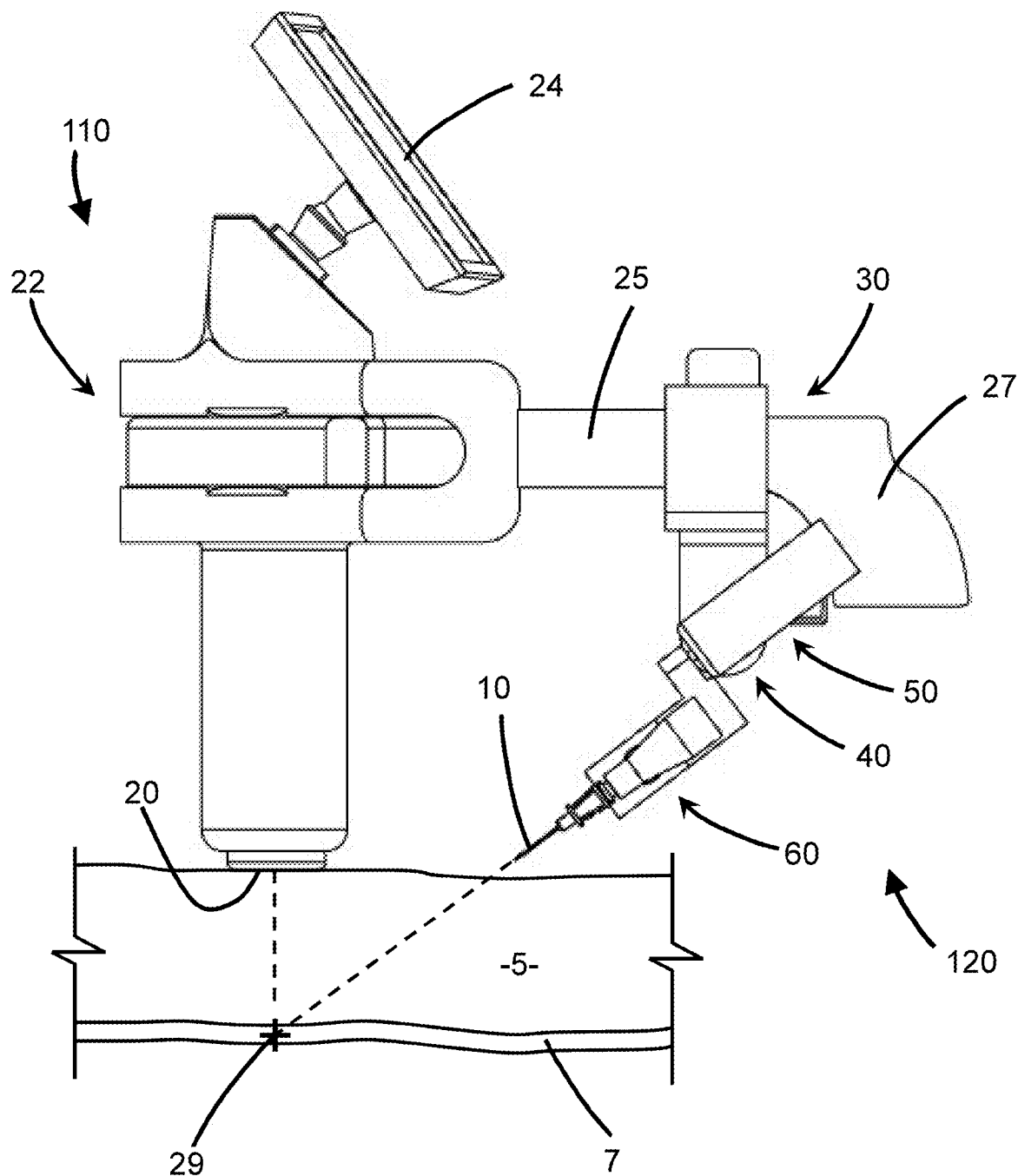
FIG. 2 is a side view of the insertion device of FIG. 1 and schematic diagram of placement for use.

The insertion device 100, such as shown in the embodiments of FIGS. 1 and 2, includes a detector 20 to obtain data and information on the tissue of a subcutaneous area, a processor 22 to use this data to calculate various positioning and adjustment parameters for a penetrating member 10, such as a needle which may be an introducer needle, for insertion to a desired preselected target point 29 within the tissue based on the calculated parameters. The target point 29 may be any point located subcutaneously within a patient, such as in a blood vessel. Identifying the target vessel is a skill typical of many trained medical professionals in the healthcare industry. Guiding a needle to that target is the challenge, however, given the complications and risks to the patient from tissue deformation and vein rolling.

In at least one embodiment, the insertion device 100 allows the user to obtain information about a target vessel within tissue through an imaging modality, such as by ultrasound, and select a target point 29 on a display 24 showing a corresponding image of the vessel. The target point 29 can be adjusted on the display 24 by a user, such as on a touch screen, and a processor 22 automatically calculates the resulting height, trajectory, angle and distance the tip of a penetrating member needs to travel from its current location to reach the targeted location within the patient. Using these calculations, the processor 22 provides operative data or instructions to various actuators 32, 42, 52 of the positioner 120 to move the tip of the penetrating member 10 in various directions in an automated fashion to arrive at the desired position ready for deployment. Each actuator 32, 42, 52 may include sensors that send positional information to the processor 20 to be used in making the adjustment calculations. Once the desired position is achieved, the device 100 may be actuated to deploy the penetrating member 10 to advance the calculated distance. The processor 22 may also instruct the penetrating member 10 to automatically stop once it reaches the preselected target point 29 so that it does not go past the target point 29. The processor may also provide instructions to a vibrational actuator 62 to initiate and induce vibrating, such as reciprocating, motion to the penetrating member 10 during deployment to overcome the tissue deformation and vein rolling complications typically encountered in needle insertion.

Figure 3:
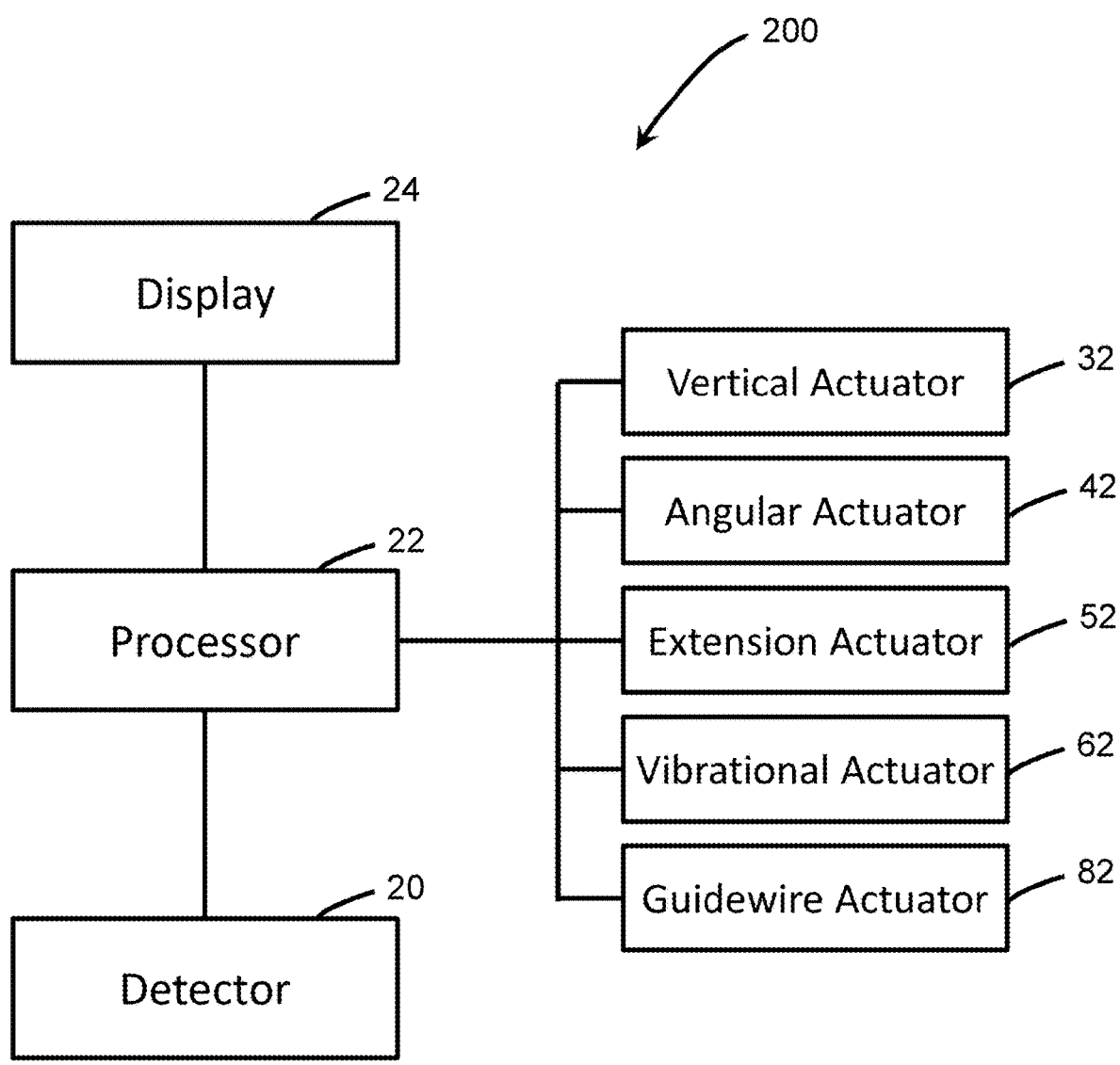
FIG. 3 is a schematic diagram of the system for insertion of a penetrating member.

As seen in FIG. 3, the insertion device 100 also includes a system 200 in which information or data representative of the tissue below the surface, including cavities such as blood vessels, is obtained by a detector 20. In some embodiments, these data are images obtained by the detector 20, which may be an imaging detector. The data of the tissue beneath the surface are transmitted to a processor 22, which calculates the distance between a preselected target point 29 within the tissue or body cavity and the tissue surface. Computational software, logic circuits, and the like of the processor 22 uses this calculated distance to calculate adjustment data for vertical actuator 32, angular actuator 42, and extension actuator 52 and transmits this data to the corresponding actuator for movement of the penetrating member 10. The processor 22 also determines vibrational data for a vibrational actuator 62 based on the operative parameters of the actuator 62, and transmits this data to the vibrational actuator 62 for activation and inducing vibrational or reciprocating motion in the penetrating member 10 for deployment. Transmission of data to and activation of the various actuators 32, 42, 52, 62 may occur in any order or in a predetermined or defined order as set forth by the processor 22. The penetrating member 10 may be deployed automatically based on the extension adjustment data sent to the extension actuator 52. In some embodiments, a user decides when the appropriate positioning for the penetrating member 10 has been reached to align with the projected path to intersect the target point 29, and he/she may activate a deployment command, which is transmitted to the processor 22 and relayed on to the extension actuator 52, which extends the penetrating member 10 by a pre-calculated distance to the target point 29 below the skin based on the information from the images obtained.

In some embodiments, the detector 20 is an imaging detector, such as an ultrasound probe or other transceiver. The data obtained by the detector 20 may be presented on a display 24, which can be viewed by a user. A representation of a pre-selected target point 29' may be overlaid on the image presented on the display 24, and may be moved around by a user. In at least one embodiment, the user may interact with the image or representations on the display 24, such as through an interactive touch screen or joystick, to move the representative target point 29' around on the display 24. As the representative target point 29' is moved on the display 24, the processor 22 calculates updated adjustment data for the vertical actuator 32, angular actuator 42, and extension actuator 52 based on the new representative target point 29'. This may be performed any number of times before a final target point is decided by a user, at which point the user may decide to deploy the penetrating member 10 for insertion and the corresponding instruction is sent to the extension actuator 52.

Figure 4A:
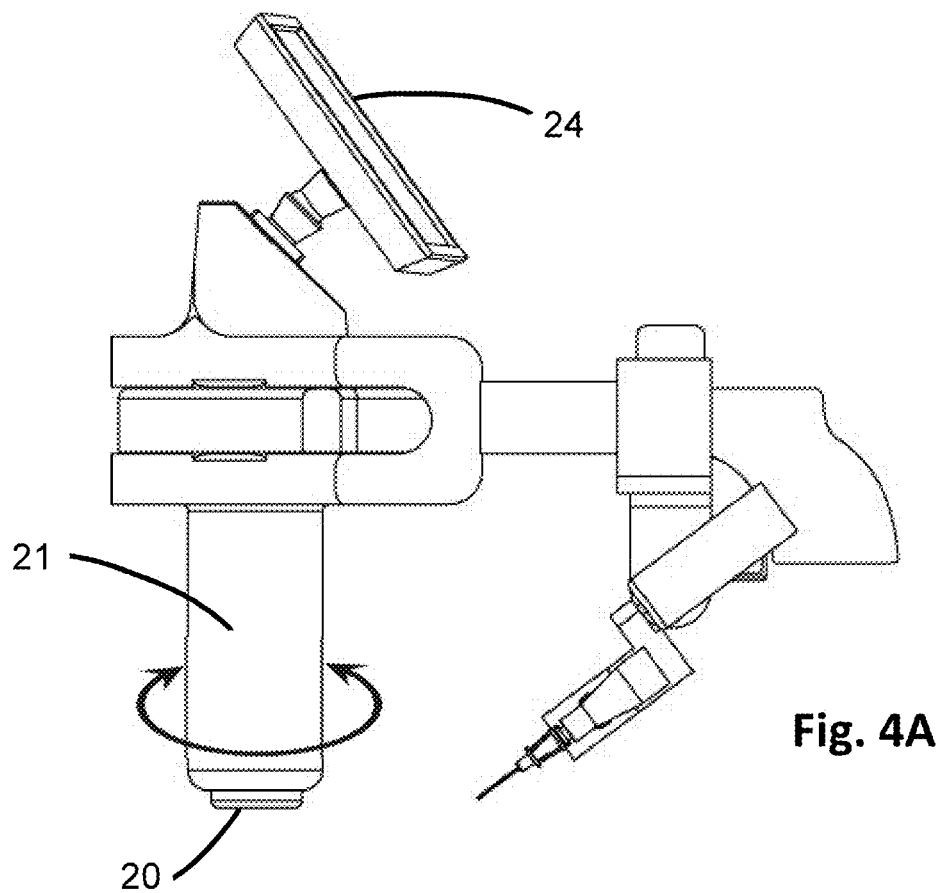
FIG. 4A is a side view of the insertion device of FIG. 2 showing adjustment of the handle.

In use, the insertion device 100 is placed alongside or adjacent to the tissue, such as skin, of a patient in order to locate a target vessel, such as a vein. In at least one embodiment, as in FIGS. 1 and 2, the device 100 is handheld and includes a handle 21 which may be gripped by a user, such as a clinician or medical personnel. The handle 21 may be ergonomically shaped for increased efficiency and comfort in holding, particularly for a prolonged period of time if necessary. The handle 21 is preferably gripped by the non-dominant hand of a user, such as in the left hand of a right-handed person, to leave the dominant hand available for selecting a target location and deploying the device 100. Accordingly, the device 100 can be used equally by right-handed and left-handed individuals, and is not specific to grip direction. Indeed, in some embodiments the handle 21 may be rotatable about an axis, as shown in FIG. 4A, to accommodate different grip orientations or positions or to obtain different image views when imaging.

Figure 4B:
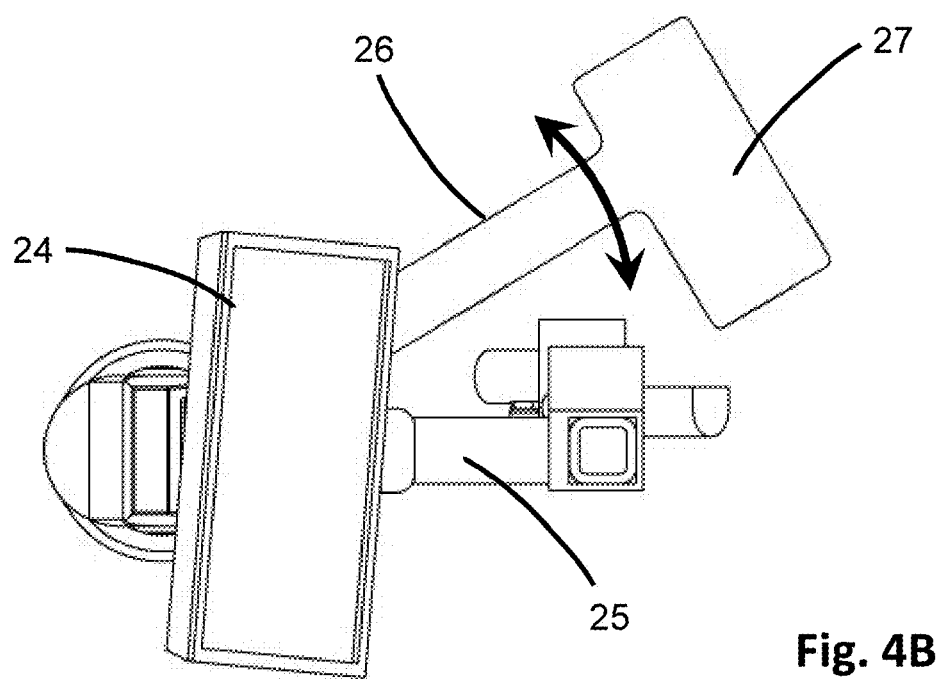
FIG. 4B is a top plan view of the insertion device of FIG. 2 showing adjustment of the side arm for positioning.

In at least one embodiment, the insertion device 100 also includes a support 27 which may be positioned in the elbow, shoulder, arm or chest of the user. The support 27 provides additional stability for a user when positioning and using the device 100. As depicted in FIG. 4B, the support 27 may be spaced apart from the handle 21, such as by a side arm 26 that corresponds to a user's arm, and may be adjustable in length to accommodate a user's reach. The side arm 26 may be movable in an arcuate path, as indicated by the directional arrow in FIG. 4B, to adjust the angle of the side arm and permit a user positioned next to a patient to comfortably use the insertion device 100 while properly aligning it as desired to target a vessel. The range of motion for the side arm 26 may be up to 360°, and therefore may permit any desired angle of approach. For example, a user may sit or stand adjacent to the patient and perpendicular to the desired target blood vessel, and yet the insertion device 100 may still be used to position the penetrating member 10 in alignment with the target blood vessel. The full range of motion of the side arm 26 may also permit switching from right-handed to left-handed use.

The insertion device 100 includes a detector 20 which is placed near, adjacent to, or even touching the area of the patient to be imaged, such as depicted in FIG. 2. In at least one embodiment, the detector 20 is located at a terminal end of the handle 21, such that the detector 20 may be positioned along the skin or other tissue 5 of a patient by moving the handle 21 over the patient. The detector 20 obtains information or data about the surrounding area, such as the subdermal area, and may including locational information of the tissue 5, cavities 7 and other structures therein. In at least one embodiment, the detector 20 is of an imaging modality to visualize a subcutaneous or percutaneous area of a patient, also referred to as a target zone 28 as shown in FIG. 5B, for targeting a particular blood vessel or body cavity 7. The target zone 28 imaged may be any shape, volume, or depth D as the particular imaging modality is capable of producing. The imaging modality may be any suitable form of imaging the subdermal area of a patient, such as but not limited to ultrasound, computerized tomography, and magnetic resonance imaging. In a preferred embodiment, as shown in FIG. 5C, ultrasound is useful for its ability to provide images that clearly distinguish between tissue 5 and body cavity 7, such as the interior of a blood vessel, below the surface of the skin. As used herein, "tissue" may refer to any tissue or organ of the body, and refers specifically to substantive material having mass. For instance, tissue may refer equally to skin, muscle, tendon, fat, bone, and organ walls. In contrast, "body cavity" as used herein may refer to the cavity, open interior, lumen or volume of space within a tissue or organ, such as blood vessels, veins, arteries, and the like.

Therefore, in at least one embodiment, the detector 20 is an ultrasound transducer that emits and receives ultrasound waves through the skin and tissue of a patient for visualization. Typical B-mode ultrasound imaging may be used in the detector 20, though Doppler ultrasound could also be used to distinguish blood flows of different directions. Linear or curvilinear ultrasound transducers are preferable, though sector phased arrays may be used in some embodiments. The ultrasound detector 20 may operate in the frequency range of 3-15 MHz, but more preferably in the range of 6-10 MHz to provide a good contrast between resolution and depth of penetration of the ultrasound, since depth of penetration is inversely related to frequency. Highly accurate measurement of the pixel size is important as it relates to distance, or phase velocity of sound in tissue, for accurate placement of the penetrating member 10. The ultrasound detector 20 may be operated in a long-axis image plane view, where vessels are viewed longitudinally, or a short-axis view, where the vessels are viewed in cross-section and appear as circular structures in resulting images, as in FIG. 5C. Imaging in the short-axis view is preferable in at least one embodiment to better visualize the body cavities 7, which appear as black spaces against the tissue 5, shown in white. The short-axis view permits the depth of the blood vessel to be seen for determining optimal placement of a target point 29 so as not to blow the vein or vessel. In either view scheme, the image plane produced by the detector 20 is at a known angle relative to the various actuators, discussed below, for proper positioning accuracy and co-registration of the ultrasound image and penetrating member 10 spatial coordinates.

The insertion device 100 further includes a processor 22 in electronic communication with the detector 20, and receives the data obtained by the detector 20 regarding the location of tissue 5 and cavities 7 therein. In some embodiments, these data are arranged as images of the subdermal area obtained by the detector 20, and are transmitted to the processor 22 and to a display 24, such as a screen that presents the images for visualization by a user, as depicted in FIGS. 1 and 2. FIG. 5C shows an example of an ultrasound image obtained by the detector 20 as presented on the display 24. The display 24 also shows a pictorial representation of the target point 29', such as with crosshairs, a target sign, or other symbol in conjunction with the images from the detector 20. The representative target point 29' image on the display 24 may be moved around, such as up and down on the display 24, by a user. As the representative target point 29' is moved, the positioning of the penetrating member 10 is adjusted, as described below, which may occur automatically and in real time. The display 24 may show additional information, including but not limited to parameters of the detector 20 (such as the frequency used), screen resolution, magnification, measurements or position information from the various components of the positioner 120 (discussed in greater detail below), and buttons or areas to activate various components of the insertion device 100.

The display 24 may be a passive or interactive screen. In at least one embodiment, the display 24 is a touch screen that may operate through a resistive mechanism, capacitive mechanism, or other haptic feedback mechanism. For instance, the representative target point 29' on the display 24 may be movable by touch on the touch screen, such as by sliding a finger, thumb or selection device along the display 24 in a continuous path, or by touching the display 24 screen in discrete locations to select new positions for the representative target point 29'. In some embodiments, the display 24 and processor 22 may be included in a single device, such as a smart phone, personal digital assistant (PDA) or tablet computer that may be removably connected to the insertion device 100 through a wireless protocol such as Bluetooth® or through a wired, multi-pin connector. In other embodiments, the display 24 and processor 22 are included in a single device, which may be integrated with the rest of the insertion device 100. In further embodiments, the processor 22 is an integrated component of the insertion device 100, and may be located within a housing 23 as in FIG. 1, and the display 24 may be separately removable from the remainder of the insertion device 100.

In other embodiments, the display 24 is a passive screen, such as a monitor, and the device 100 may include a joystick or directional button(s) (not shown) to enable the user to guide the imaging assembly 110 and target the vein. The joystick or directional button(s) may output a direction signal to the processor 22 based on the orientation and inclination of the joystick lever, or the particular directional button(s) pressed or selected. The output signal from the joystick or directional button(s) controls the position of a representative target point 29', such as a crosshair, shown on the display 24 such that the target point 29 image overlays the target location. In some embodiments, the joystick or directional button(s) may be located at or near the display 24, such as along the edges of the frame of the monitor. In other embodiments, the joystick or directional button(s) may be placed on the handle 21 to enable one-handed operation of the device 100 for imaging.

The processor 22 is in electrical communication with, receives information from, the display 24 on the location and change of location of the desired target point 29 as indicated by a user from interacting with the representative target point 29' on the display 24, such as by touch screen interaction. The processor 22 includes program(s), software, logic circuits, or other computational abilities to calculate how to adjust the penetrating member 10 from its existing position to a position that will bring it to the target point 29 as indicated by the user-indicated information provided from the display 24 interaction.

Figure 5A:
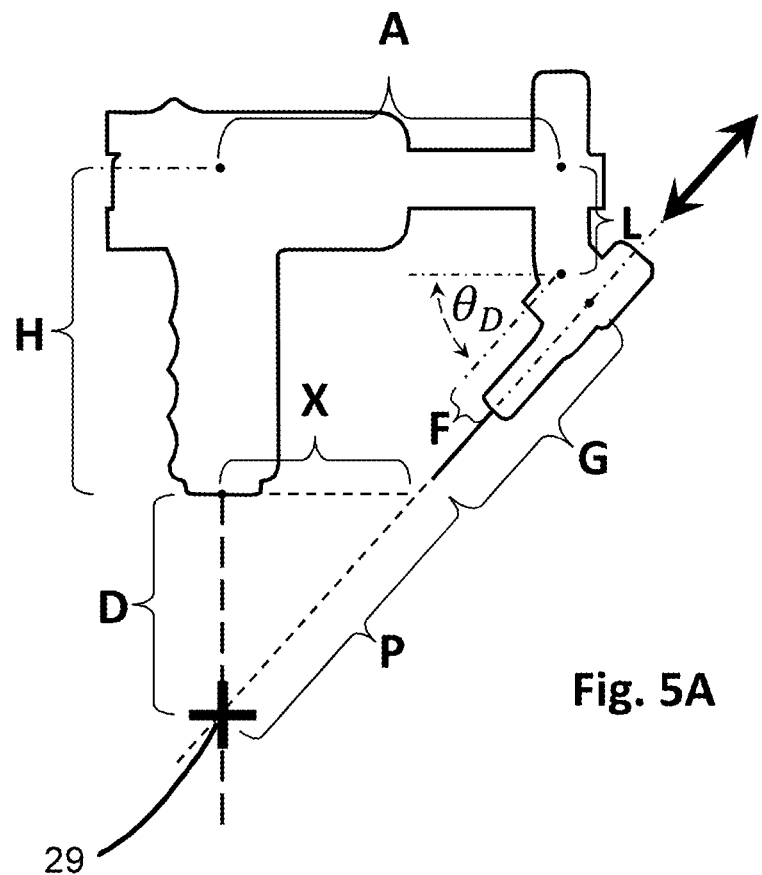
FIG. 5A is a schematic diagram of the insertion device showing dimensions used for calculations by the processor.
Figure 5B:
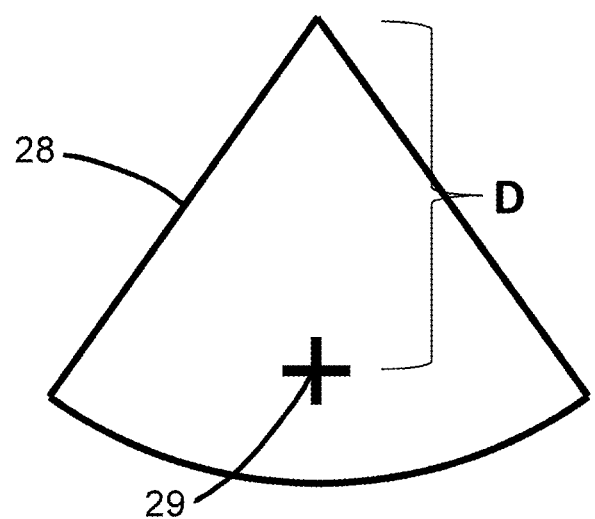
FIG. 5B is a schematic diagram showing the target zone used for calculations by the processor.
Figure 5C:
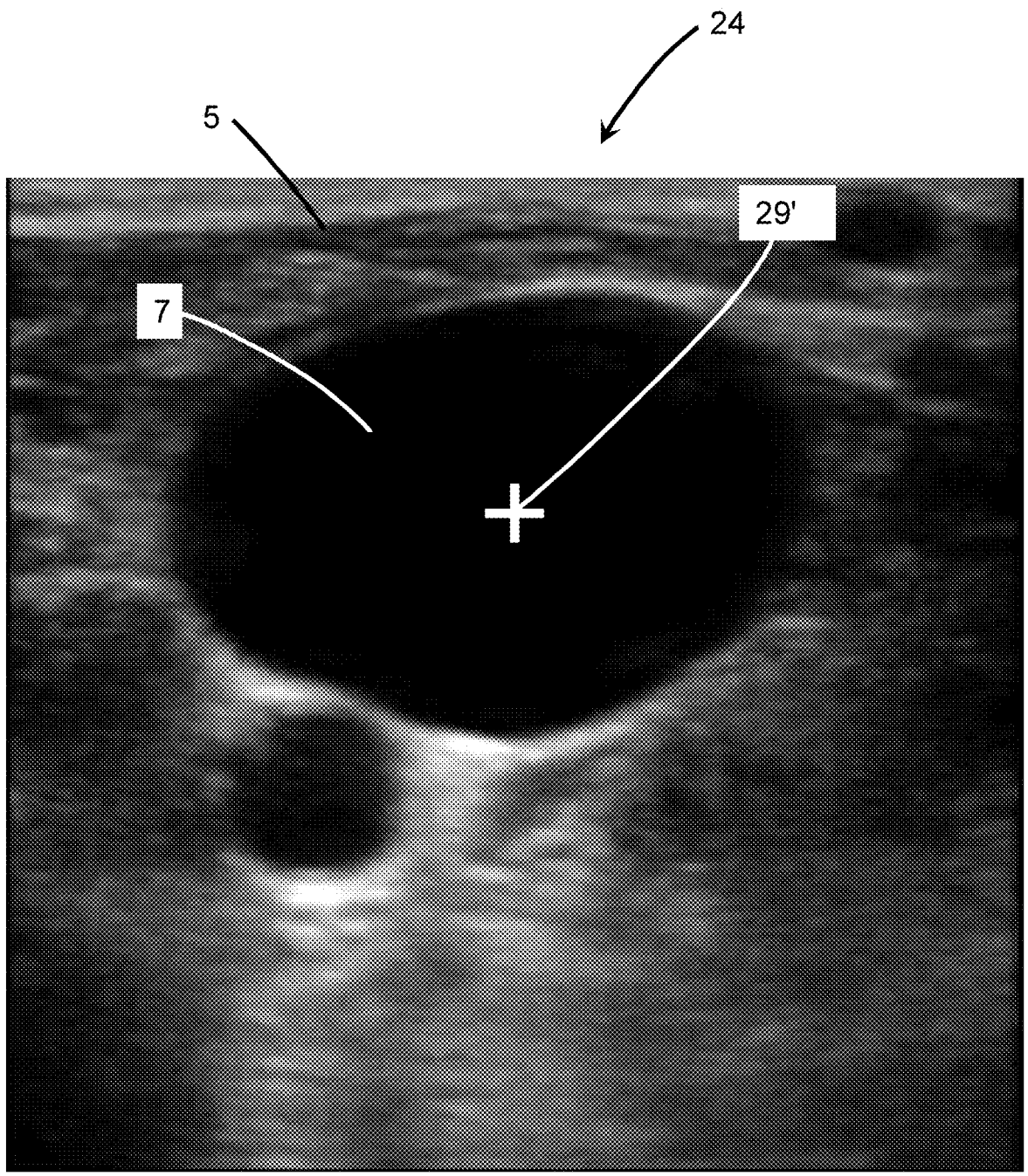
FIG. 5C is an exemplary ultrasound display used in visually adjusting the insertion device.

For example, FIG. 5A shows a schematic representation of the insertion device 100 depicting various dimensions used in the calculations by the processor 22. Some of these dimensions are fixed dimensions of the device 100. For instance, H is the height of the handle 21 from the detector 20 to a center of the primary arm 25. The distance A is the length of the primary arm 25 from the center of the handle 21 to the center of the positioner 120, such as the vertical actuator 32. In some embodiments, A is a fixed length, such as when the primary arm 25 is of a fixed length. The size of the mounting for the penetrating member 10, and the length of the penetrating tip 10, such as a needle, collectively referenced as G, is also known and fixed. The distance between the mounting for the penetrating member 10 and the angular adjustment 30, F, also remains fixed.

Other dimensions of the calculations will vary. For example, D is the distance between the detector 20, located at the surface of the tissue 5 or skin, to the target point 29 within the body cavity 7, such as the interior of a blood vessel beneath the skin. D will therefore vary by patient, as well as which blood vessel is used as the target, how much tissue lies between the target blood vessel and the skin or surface on which the detector 20 is placed, and even the position of the target blood vessel and how full or compressed the blood vessel is. In at least one embodiment, the height L of the positioner 120 may be varied. In some embodiments, the height L of FIG. 5A may be pre-set before use such that it is fixed when the insertion device 100 is in use. Using this information, the microprocessor may determine the angle of inclination, $\theta_D$, and the distance from the tip of the penetrating member 10 to the target point 29, P, using the Pythagorean Theorem and trigonometry. For instance, once way the calculations may be performed are as follows:

$$P = \frac{A + F \cdot \sin\theta D}{\cos\theta D} - G$$

$$(H + D - L) \cdot \cos\theta D - A \cdot \sin\theta D = F$$

Alternatively, the angle $\theta_D$ could be pre-set by a user, and the height L and distance P would be calculated using similar mathematical relationships.

Looking at it another way, and still with reference to FIG. 5A, the depth D forms one side of a triangle, distance X is the distance between the center of the detector 20 to the tip of the penetrating member 10 and forms a right angle with D and another leg of the triangle. The distance for insertion of the penetrating member 10 is P, which is the hypotenuse of the triangle, and is calculated by solving for P in the following equation:

$$D^2 + X^2 = P^2$$

The angle of insertion $\theta_D$ is therefore calculated as:

$$\cos\theta D = \frac{X}{P}$$

Accordingly, there are many ways to perform the calculations based on the known constant dimensions and the variables. The above provide just a few examples. In other embodiments, height L may be adjustable and automated during the use of the insertion device 100, such as when a shallow angle, or acute $\theta_D$, is needed. This may be the case if the target blood vessel is itself very shallow or partially collapsed, or if it is located superficially below the surface of the skin. In such illustrative embodiments, to achieve an appropriate angle, the height L may be increased to position the penetrating member 10 to reach the target point 29. The amount of height L increase or decrease is calculated in real-time by the processor of the processor 22 as the angle $\theta_D$ is also calculated for adjustment based on the information input at the display 24 by the user. For instance, as the user slides a finger up along the display 24, the target point 29 indicator also moves up and the angle $\theta_D$ is made shallower or more acute. Conversely, as the user slides a finger down along the display 24, the target point 29 indicator also moves down and the angle $\theta_D$ increases or becomes deeper. Sliding a finger along a touchscreen display 24 is just one embodiment. In other embodiments, knobs or dials can be used to move the representative target point 29' up or down on the screen, which would correspond to adjustments in the angle $\theta_D$ as determined by the processor 22.

The processor 22 is also in electrical communication with a positioner 120 that is spaced apart from the imaging assembly 110 of the insertion device 100, such as by a primary arm 25. The primary arm 25 may be of any suitable length sufficient to space the penetrating member 10 from the detector 20 so that the penetrating member 10 can approach, and reach, the desired target point 29. The primary arm 25 may be adjustable, such as manually or automated such as with an actuator, but in at least one embodiment it is stationary and of a fixed length.

Figure 6:
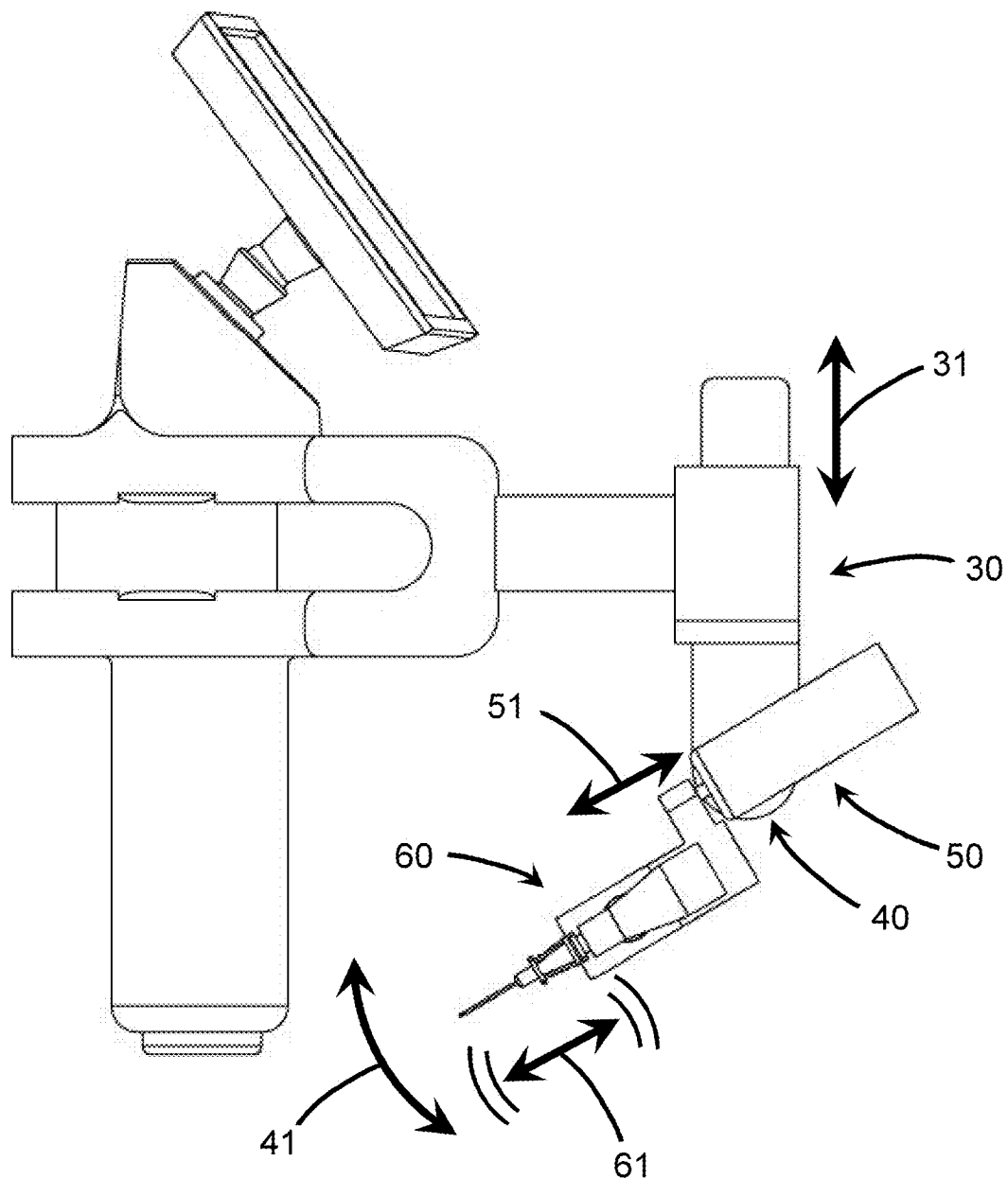
FIG. 6 is side view of the insertion device of FIG. 1 showing schematic representations of the various adjustments directed by the processor for automated insertion.
Figure 7:
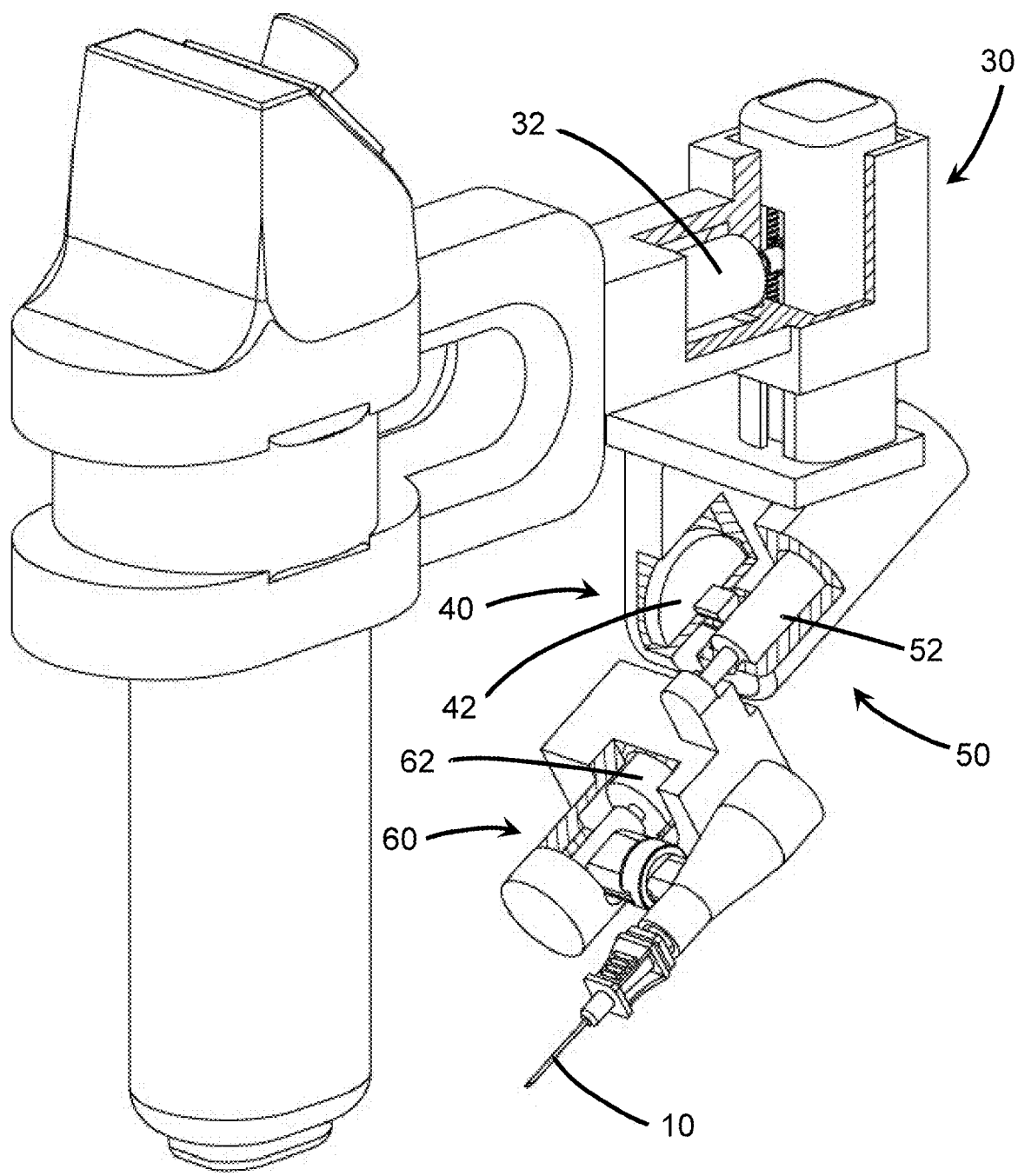
FIG. 7 shows perspective view of the insertion device of FIG. 6 in partial cut-away to show the various actuators.

With reference to FIGS. 1, 2 and 6, the positioner 120 includes a vertical adjustment 30 that adjusts the penetrating member 10 in a vertical direction 31; an angular adjustment 40 that adjusts the angle of inclination of the penetrating member 10 along an angular direction 41; and an extension adjustment 50 that moves the penetrating member in a linear direction 51 toward or away from the target point 29 for insertion and removal. A vibrator 60 that provides reciprocating motion in a longitudinal direction 61 along the penetrating member 10 is also present in the insertion device 100, but need not be a component of the positioner 120. As seen in FIG. 7, each of the adjustment parameters is affected by actuators 32, 42, 52, 62 that receive signals from the processor 22 providing instruction on movement parameters and may automatically move according to those instructions to adjust the positioning of the penetrating member 10.

Figure 8A:
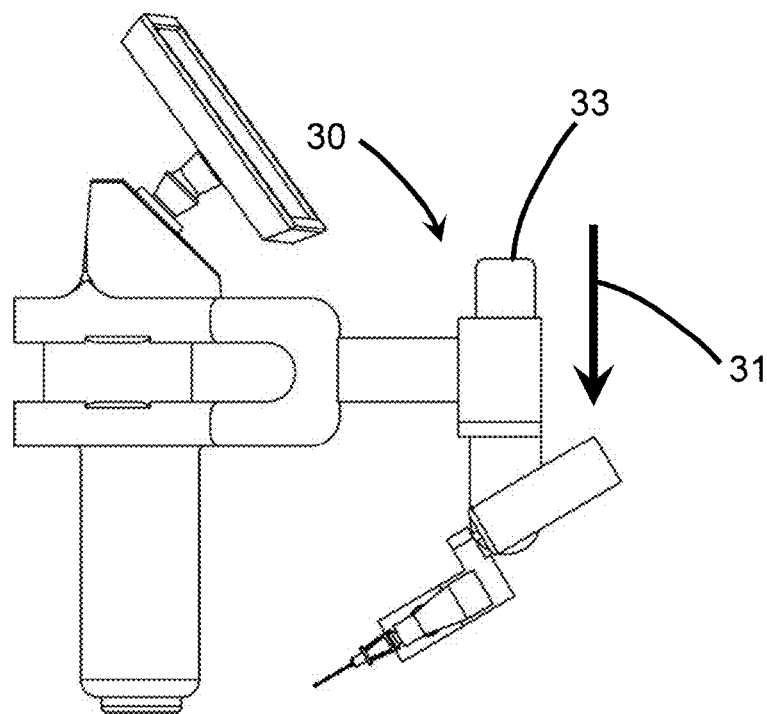
FIGS. 8A and 8B are side views showing the adjustment in the vertical direction by a vertical actuator.
Figure 8B:
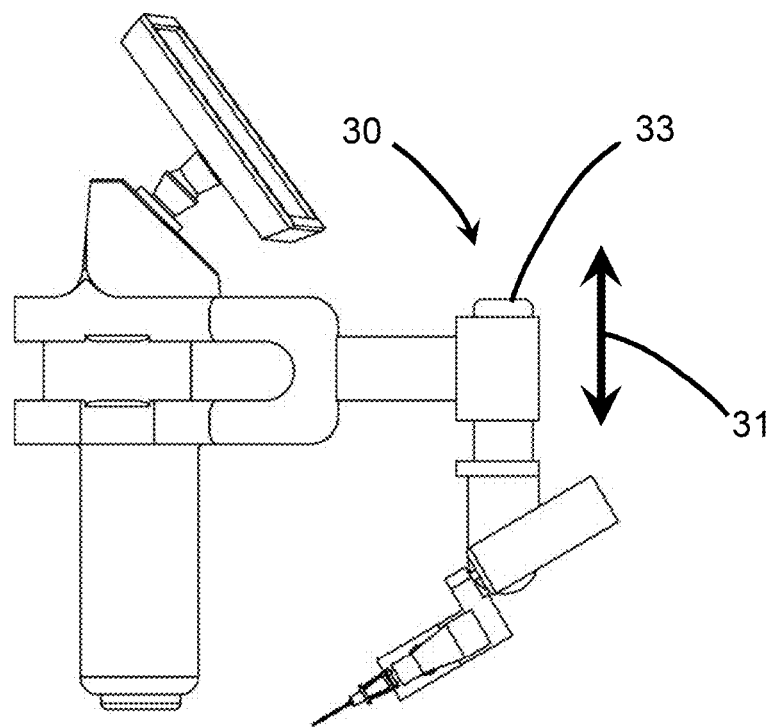
Figure 9:
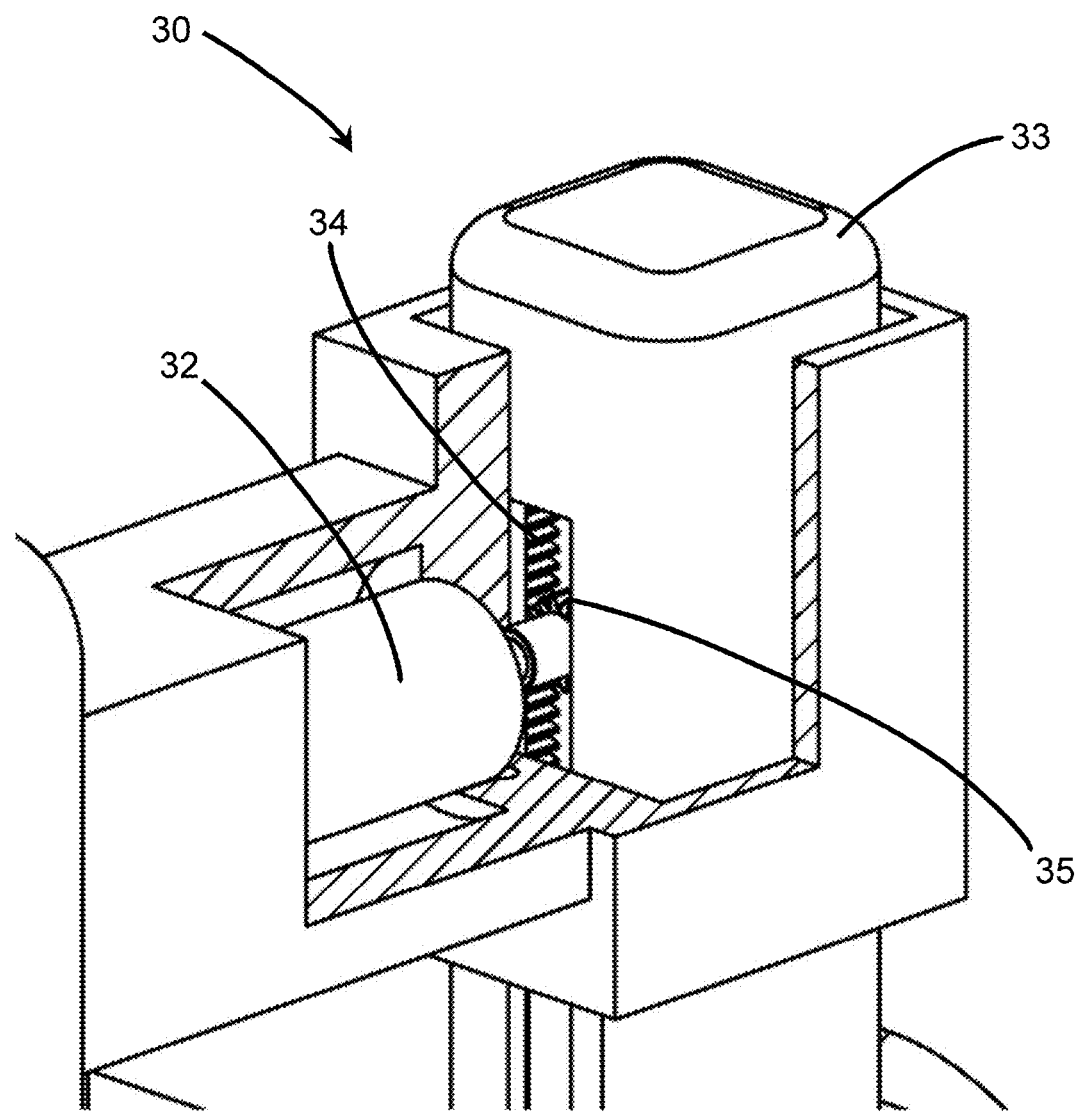
FIG. 9 is a partial cut-away showing one embodiment of the vertical actuator for vertical adjustment.

For instance, with reference to FIGS. 7-9, the vertical adjustment 30 provides a mechanism for raising or lowering the mounted penetrating member 10. Specifically, the vertical adjustment 30 includes a vertical actuator 32 which is in electrical communication with the processor 22 to receive vertical adjustment data for activation and movement. Upon receiving the signal or data from the processor 22, the vertical actuator 32 activates and moves according to the vertical adjustment data calculated by the processor 22 so as to adjust the penetrating member 10 in a vertical direction 31 with respect to the surface of the skin or other tissue being imaged for insertion. The vertical actuator 32 may be a motor that turns or acts on a shaft. For example, in at least one embodiment, as depicted in FIG. 9, the vertical actuator 32 is a rotational motor that turns a pin 35 which extends from the vertical actuator 32. The pin 35 engages a track 34, such as in an interlocking fashion between corresponding teeth or grooves on the pin 35 and track 34, such as in a rack and pinion system. As the pin 35 rotates in one direction, its extensions interdigitate with those of the track 34, and move the track 34 up or down in the vertical direction 31. When the vertical actuator 32 turns the pin 35 in the opposite direction, the track 34 is correspondingly moved in the opposite vertical direction. Accordingly, the vertical actuator 32 may be positioned perpendicular to the track 34. The track 34 may be located within a vertical housing 33. In other embodiments, the track 34 may be a slide bar, and the vertical actuator 32 may move a pin 35 between different locking positions along the slide bar to move the slide bar in the vertical direction. In still other embodiments, the vertical actuator 32 may be a linear motor disposed along the vertical direction 31, such that upon activation it causes a pin 35 or other elongate shaft to extend, thereby causing movement of the housing 33 in the vertical direction 31. As discussed above, in some embodiments, the vertical actuator 32 may be automated by the processor 22 and move in real-time as adjustments are made to the target point 29 at the display 24. In some embodiments, however, the vertical actuator 32 may not be activated, such as if adjustment in the vertical direction 31 is not needed or if the vertical height component is intended to be fixed.

Figure 10:
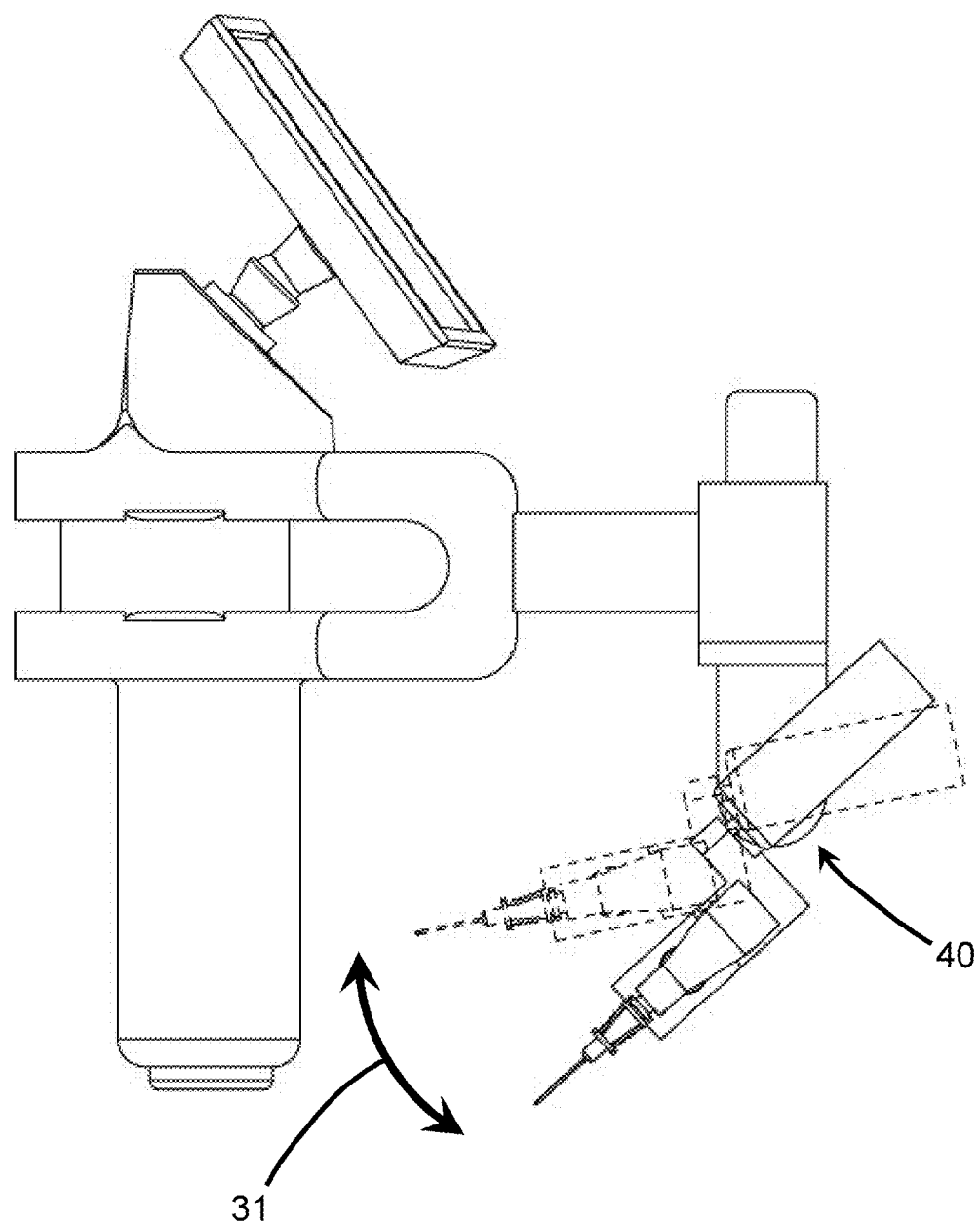
FIG. 10 is a side view showing the angular adjustment by the angular actuator.

The positioner 120 also includes an angular adjustment 40, as depicted in FIGS. 7 and 10-12B. The angular adjustment 40 includes an angular actuator 42 in electrical communication with the processor 22. The angular actuator 42 receives signals, such as angular adjustment data, from the processor 22 providing instructions on activation for changing the angle of inclination of the penetrating member 10. The angle of inclination may be any angle between 0° and 180° with respect to the surface of the tissue. In at least one embodiment, the angle of inclination is an acute angle between 0° and 90°. The angle of inclination is adjusted in the angular direction 41 as seen in FIG. 10, according to the calculations performed by the processor 22. Accordingly, the angle for penetration can be made shallower or steeper as determined by a user. In imaging embodiments, when the user moves the representative target point 29' up or down on the display 24, the corresponding signal is relayed from the processor 22, and the processor 22 updates the calculations to determine an updated or new angular adjustment data based on the new position of the representative target point 29'. This updated data is sent to the angular actuator 42, which activates to adjust the angle of the penetrating member 10 accordingly, which may be in real-time. This activation is automated by the processor 22. The angular actuator 42 may be a motor suitable for changing the angle of inclination. In a preferred embodiment, the angular actuator 42 is a rotational motor that rotates upon activation. In such embodiments, a shaft 43 extends from the angular actuator 42 into a receiver 45 or other structure not fixed and independently movable from the angular actuator. The shaft 43 and corresponding receiver 45 may be correspondingly shaped, such as being matingly fit or in a complimenting keyed arrangement, so that rotation of the shaft 43 imparted from the angular actuator 42 correspondingly turns the mating receiver 45.

Figure 11:
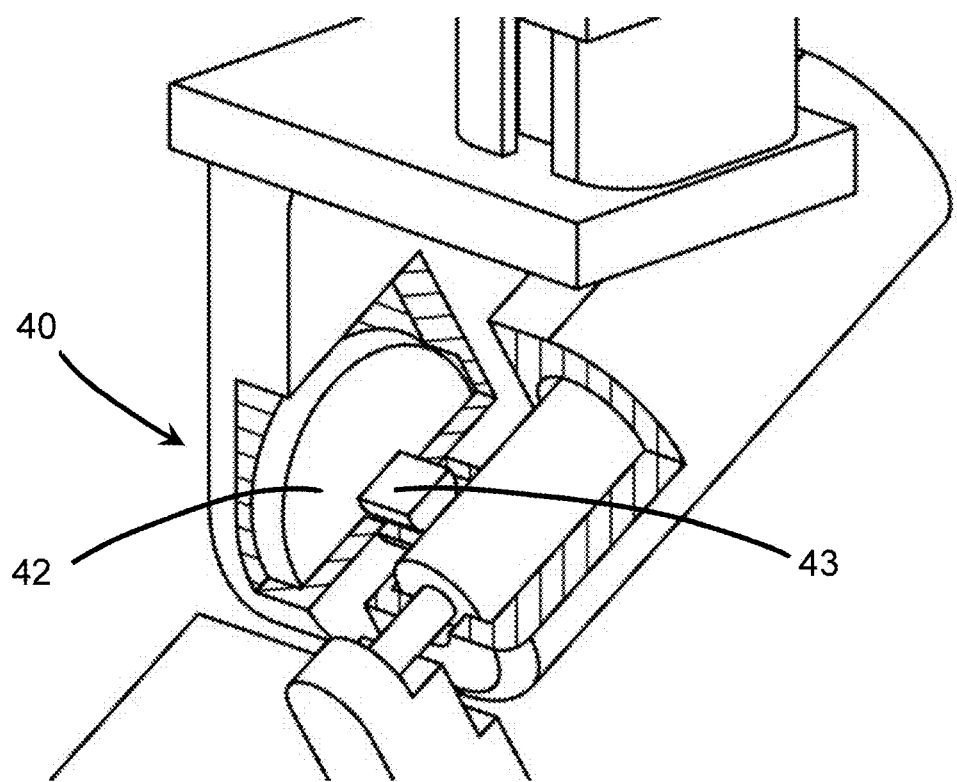
FIG. 11 is a partial cut-away showing one embodiment of the angular actuator for angular adjustment.
Figure 12A:
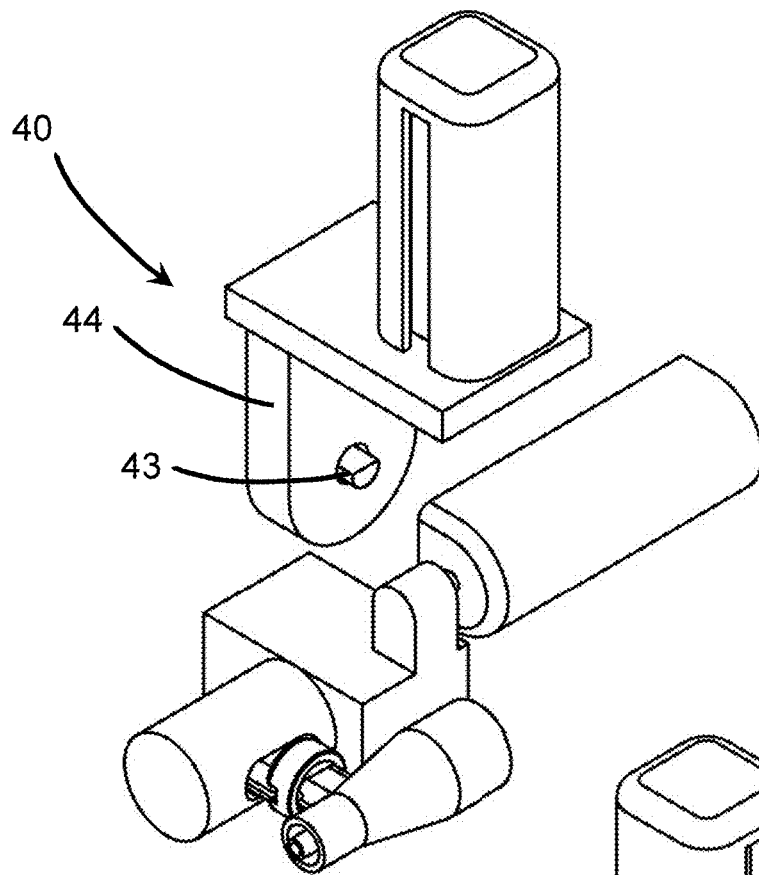
FIGS. 12A and 12B are exploded views of the portion of the insertion device having an angular actuator, showing a keyed relationship of the angular actuator from opposite directions.
Figure 12B:
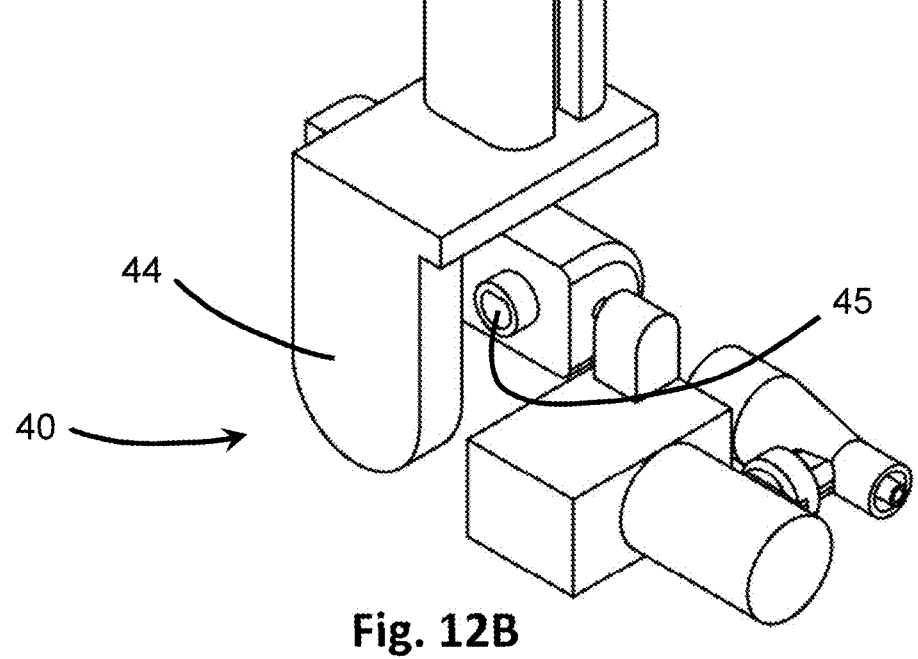

For example, in the embodiment of FIGS. 11, 12A and 12B, the shaft 43 has a keyed configuration such that it has an irregular shape, such as having a flat surface along one side of an otherwise cylindrical shape. The receiver 45 into which the shaft 43 extends is similarly keyed, having a flat surface along at least a portion of its perimeter. Accordingly, when the shaft 43 is rotated by the angular actuator 42, the specific shape engages the corresponding shape of the receiver 45 and transfers the rotational motion on to the receiver 45, thereby turning the receiver 45 as well. Since the receiver 45 is integral with a separate component of the positioner 120 from the angular actuator 42, the rotational motion conveyed to the receiver 45 through the correspondingly shaped interaction with the shaft 43 also turns the remaining portion of the positioner 120, as shown in FIG. 10. The angular actuator 42 may be surrounded by angular motor housing 44, which may include an aperture through which the shaft 43 extends, as seen in FIGS. 11 and 12A.

Figure 13:
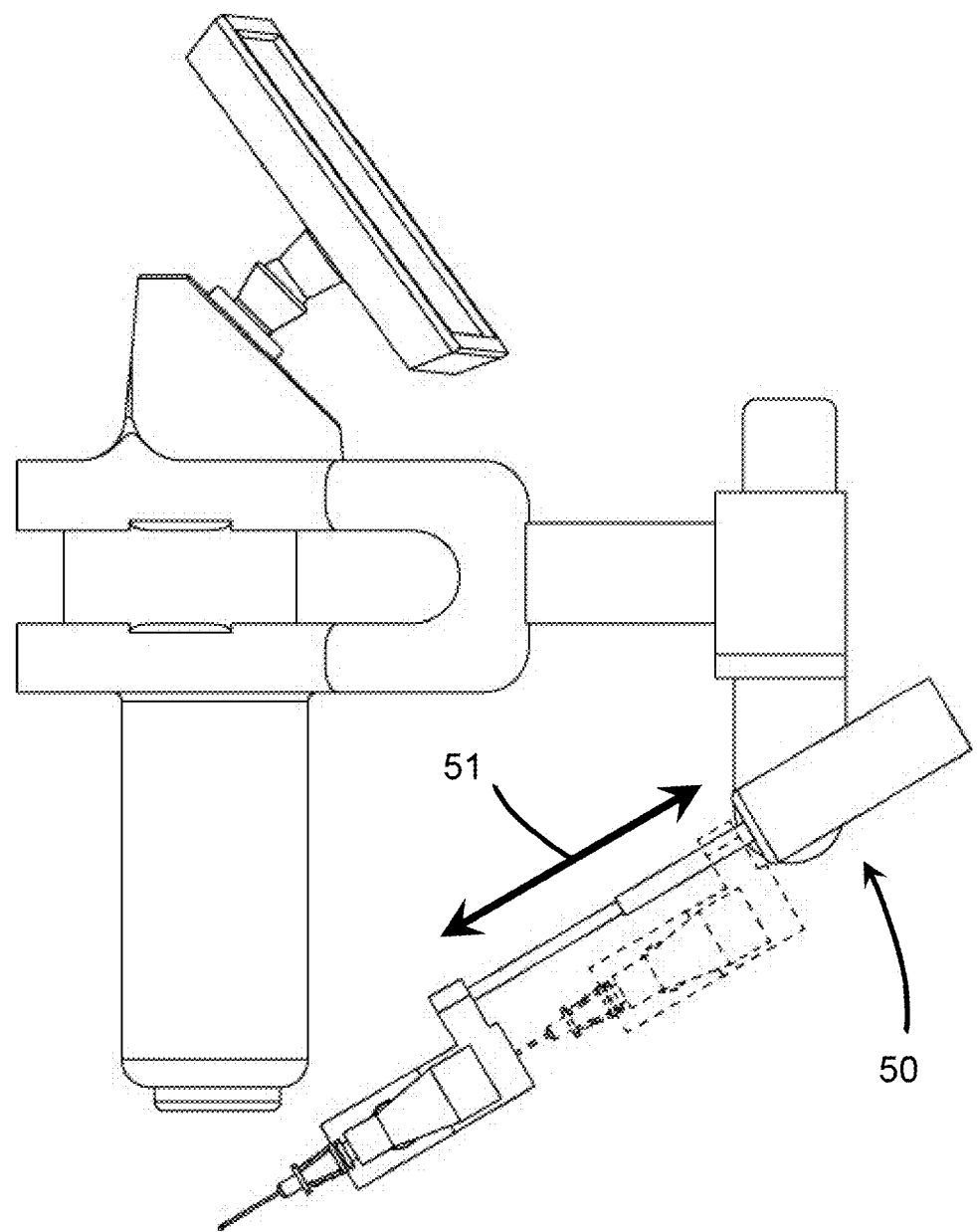
FIG. 13 is a side view showing the adjustment by linear extension.
Figure 14:
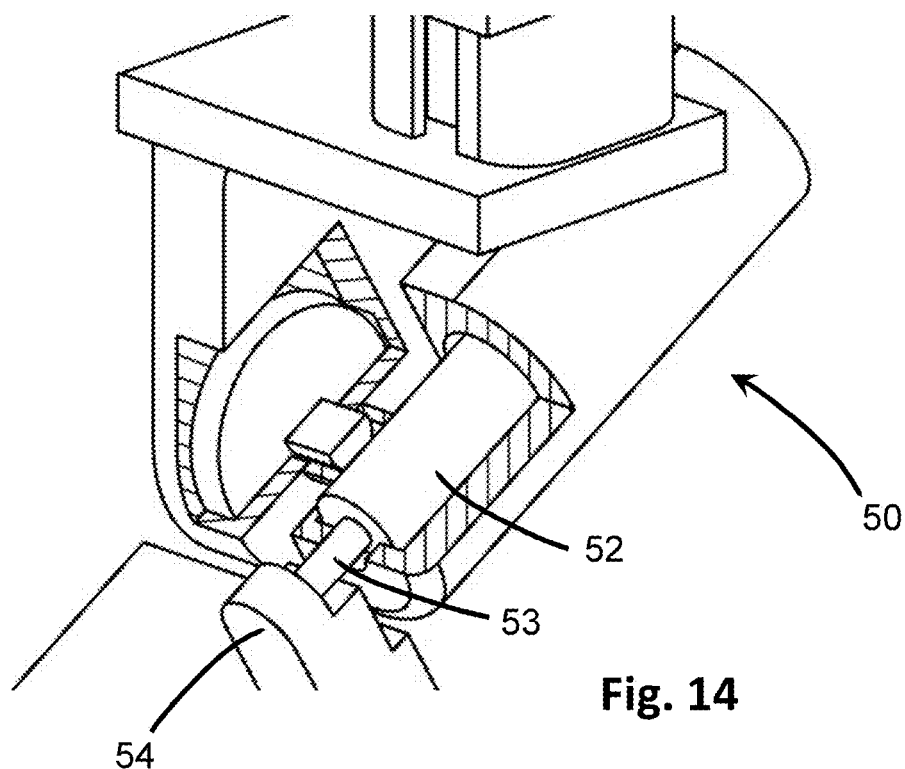
FIG. 14 is a partial cut-away showing one embodiment of the extension actuator for extension.
Figure 15A:
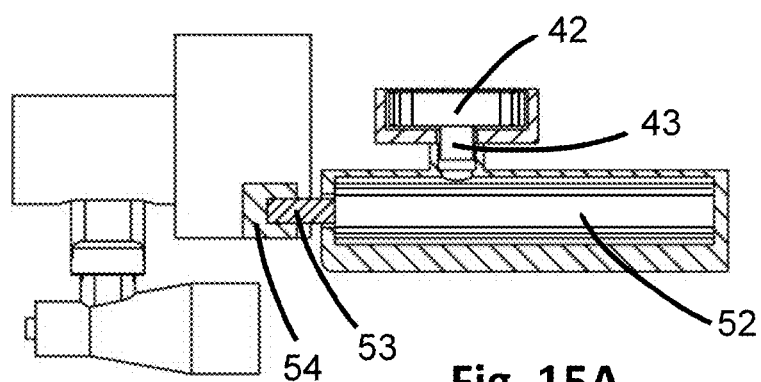
FIG. 15A is a top view in partial cross-section showing the extension actuator and connected extension shaft in a retracted position.
Figure 15B:
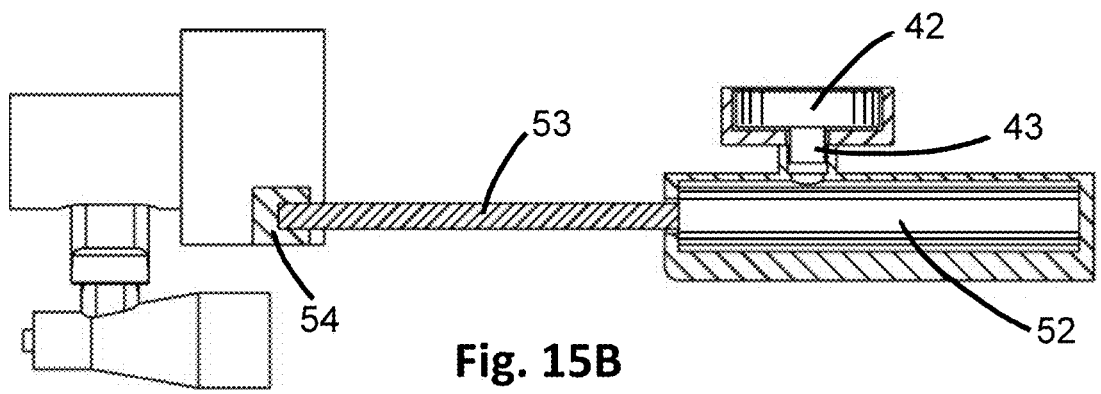
FIG. 15B is a top view in partial cross-section showing the extension actuator and connected extension shaft of FIG. 15A in an extended position.

The positioner 120 further includes an extender 50, shown in FIGS. 7 and 13-15B. The extender 50 includes an extension actuator 52 in electrical communication with the processor 22 to receive extension adjustment data and instructions on activation and distance to move. When data are received, the extension actuator 52 activates to move the penetrating member 10 in a linear direction 51, as seen in FIG. 13, by a predetermined distance as calculated by the processor 22. In at least one embodiment, as shown in FIGS. 13-15B, the extension actuator 52 is a linear motor, although other forms of motors may be used for achieving movement of the penetrating member along the linear direction 51.

The extender 50 also includes an extension shaft 53 that extends out from the extension actuator 52 to an oppositely disposed extension mount 54 located on a separate component of the positioner 120. The extension shaft 53 may be secured to or integrally formed with the extension actuator 52, the extension mount 54, or both. The extension shaft 53 may retract into or be housed within the extension actuator 52 or share a common housing, and may be pushed out of the housing by the extension actuator. In some embodiments, as shown in FIG. 13, the extension shaft 53 may be a telescoping shaft. In other embodiments, as in FIGS. 15A and 15B, the extension shaft 53 may be a uniform bar or elongate member that is moved into and out of the extension actuator 52 upon activation. The distance the extension shaft 53 is pushed out of the extension actuator 52 is directed and calculated by the processor of the processor 22, based on the positioning information for the target point 29 input by the user on the display 24. The extension shaft 53 is made of a rigid material, such that as the extension shaft 53 is moved, the extension mount 54 in which it terminates is correspondingly moved. In this manner, the penetrating member 10 is moved the calculated distance in the linear direction 51 by the extension actuator 52, as shown in FIG. 13.

In some embodiments, the extension actuator 52 is used to move the penetrating member 10 a calculated distance to align it or otherwise position it for use, such as by moving it so the tip of the penetrating member 10 touches the skin or tissue 5 of the patient. In other embodiments, the extension actuator 52 is used to deploy the penetrating member 10 such that the tip of the penetrating member 10 moves from a ready position to the location of the target point 29. In at least one embodiment, the extension actuator 53 is used to both align and deploy the penetrating member 10 in a linear direction toward the target point 29. Both alignment and deployment of the penetrating member 10 may be automated. In at least one embodiment, deployment of the penetrating member 10 occurs as a result of activation of a button or particular area of the display 24, such as a soft button or virtual button on a touch screen, or button on a joystick or other part of the insertion device 100, which may be activated separately from the alignment and positioning of the penetrating member 10 in the other various dimensions by the user's placement of the detector 20 and the action of the vertical and angular actuators 32, 42.

Figure 16A:
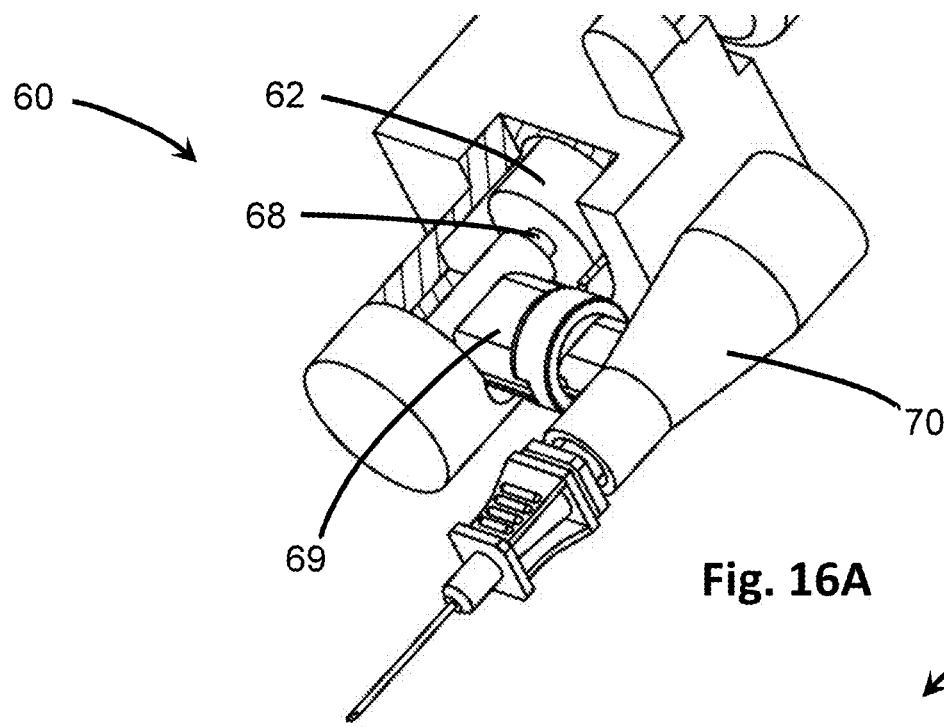
FIG. 16A is a partial cut-away showing one embodiment of the vibrational actuator for vibrational motion.
Figure 16B:
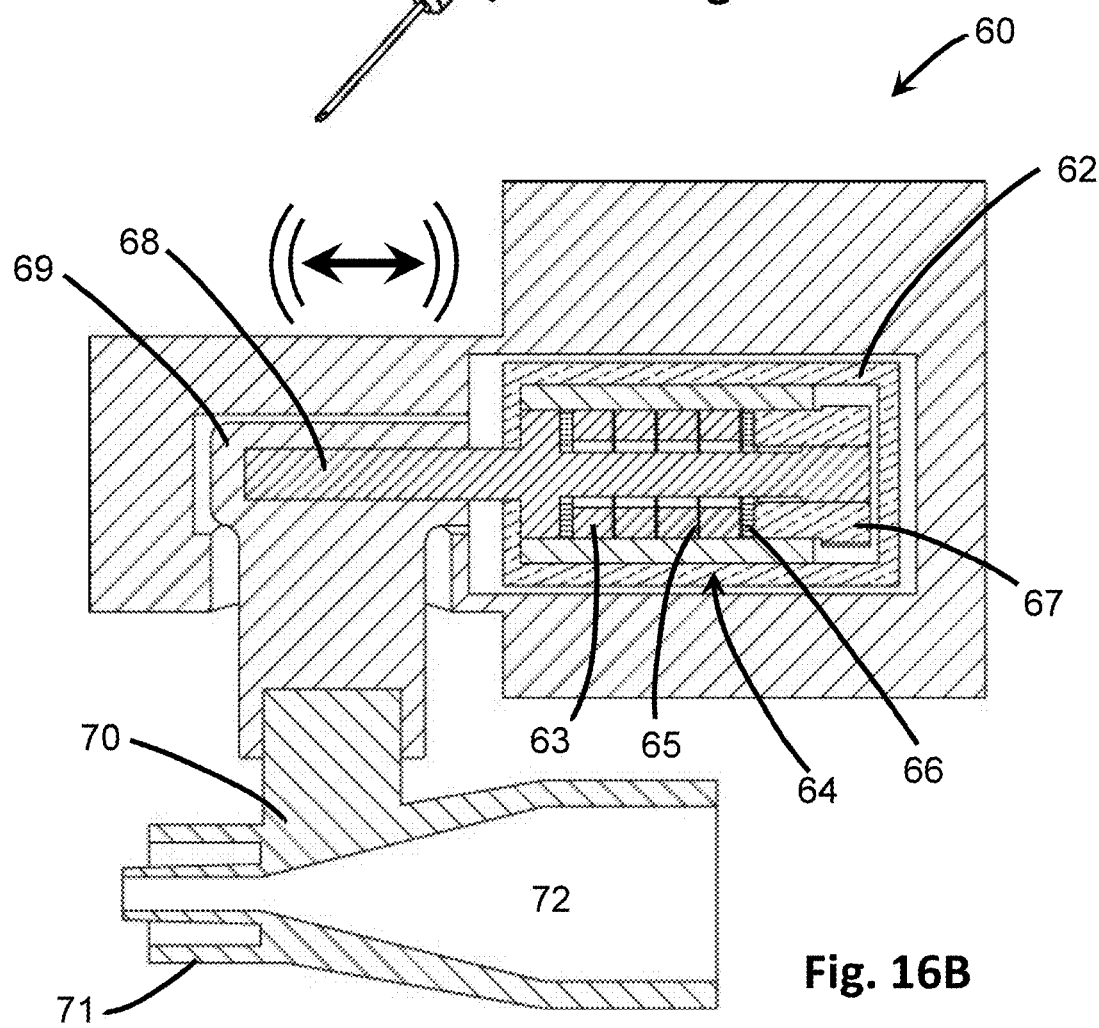
FIG. 16B is a cross-section of one embodiment of the vibrational actuator for vibrational motion.
Figure 17:
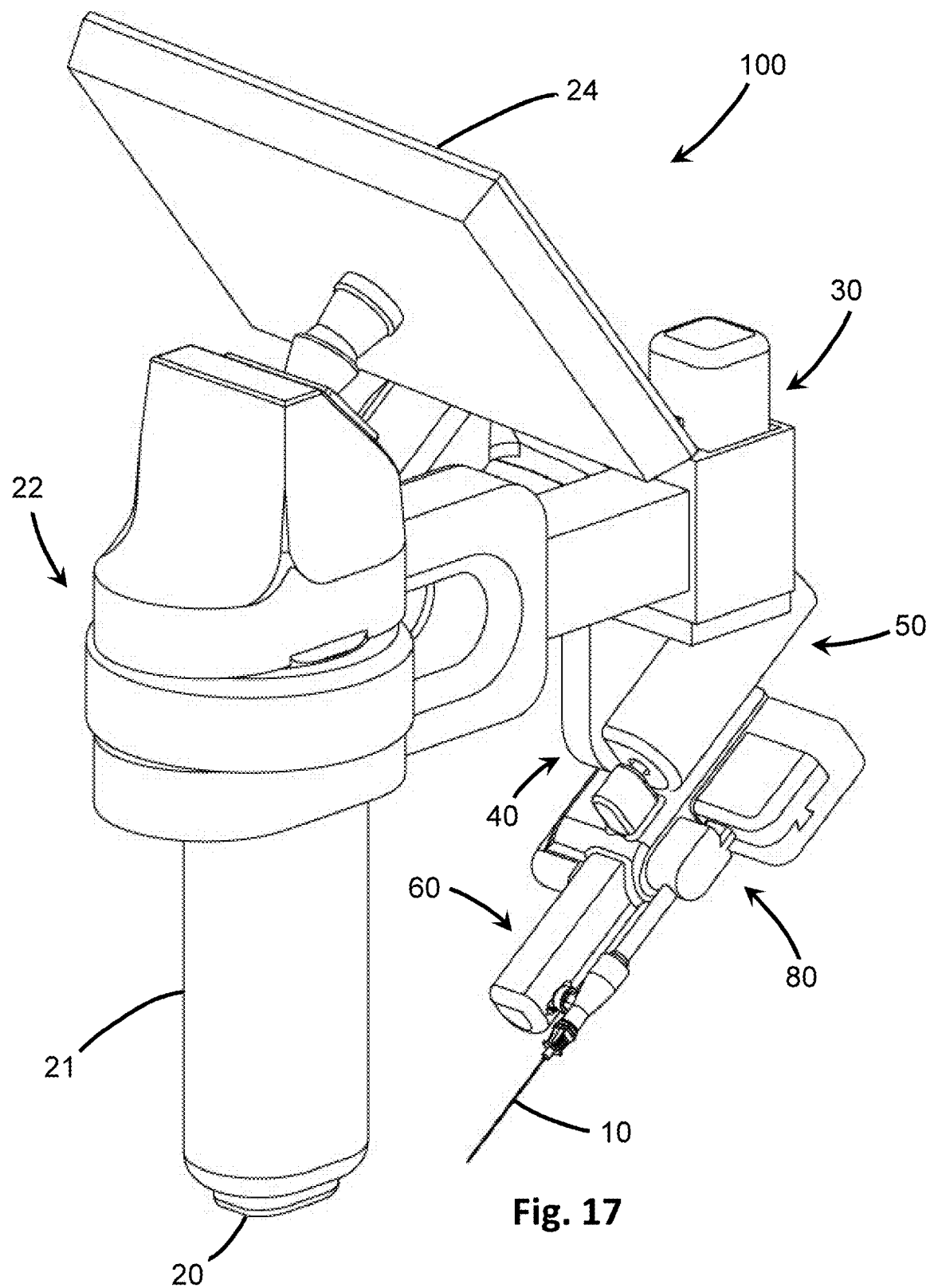
FIG. 17 is a perspective view of another embodiment of the insertion device including a guidewire for insertion.

The insertion device 100 also includes a vibrator 60, for example as shown in FIGS. 7, 16A and 16B. The vibrator 60 includes a vibrational actuator 62 in electrical communication with the processor 22 and receives vibrational data from the processor 20 instructing when to activate and the operational parameters to use, which are determined by the processor 20 and may be based on a variety of factors, including but not limited to the type of vibrational actuator 62 used, and the type and condition of the tissue 5 being penetrated. When activated, the vibrational actuator 62 provides repetitive, reciprocating or oscillating motion to the penetrating member 10 back and forth along a longitudinal direction 61. The longitudinal direction 61 is coincident with the axis of the penetrating member 10. As used herein, the terms "reciprocating," "oscillating," and "vibrating" may be used interchangeably, and refer to a back and forth motion in a longitudinal direction 61 coincident with or parallel to the length of the penetrating member 10.

Upon receiving the activation signal from the processor 22, the vibrational actuator 62 turns on. Activation may occur automatically, or only at a certain point in the insertion process, such as once the penetrating member 10 is properly positioned and aligned but prior to being deployed for insertion. Activation of the vibrational actuator 62 may therefore occur only once the proper positioning of the penetrating member 10 is confirmed by a user in some embodiments, or may automatically begin once the target point 29 is aligned.

The vibrator 60 includes a drive shaft 68 that extends from the vibrational actuator 62 to a coupler or housing connected to the penetrating member 10. The drive shaft 68 transfers the mechanical vibrational motion generated by the vibrational actuator 62 to the penetrating member 10. The vibrator 60, and therefore the vibrational actuator 62, may be axially offset from the penetrating member 10 in some embodiments, as in FIGS. 16A and 16B, or may be inline or coaxial with the penetrating member 10, as in FIGS. 20A and 20B.

In at least one embodiment, as shown in FIGS. 16A and 16B, the vibrational actuator 62 is axially offset from the penetrating member 10. Here, the vibrating assembly 60 includes a drive shaft 68 that extends from the vibrational actuator 62 to a driving coupler 69. In some embodiments, the drive shaft 68 extends at least partially into the driving coupler 69. The driving coupler 69 coordinates with, such as by connecting to, an offset coupler 70. For instance, at least a portion of the driving coupler 69 may extend into the offset coupler 70, or vice versa. The offset coupler 70 includes a hub 71 at which a proximal end of the penetrating member 10 connects, such as by a screw, twist, threaded, or keyed connection, or other suitable connection. The driving coupler 69 and offset coupler 70 run perpendicular to the drive shaft 68 and the penetrating member 10. Therefore, the driving coupler 69 and offset coupler 70 collectively transfer the vibratory motion generated by the vibrational actuator 62 and propagated by the drive shaft 68 to the penetrating member 10 along a different, parallel axis.

Figure 20A:
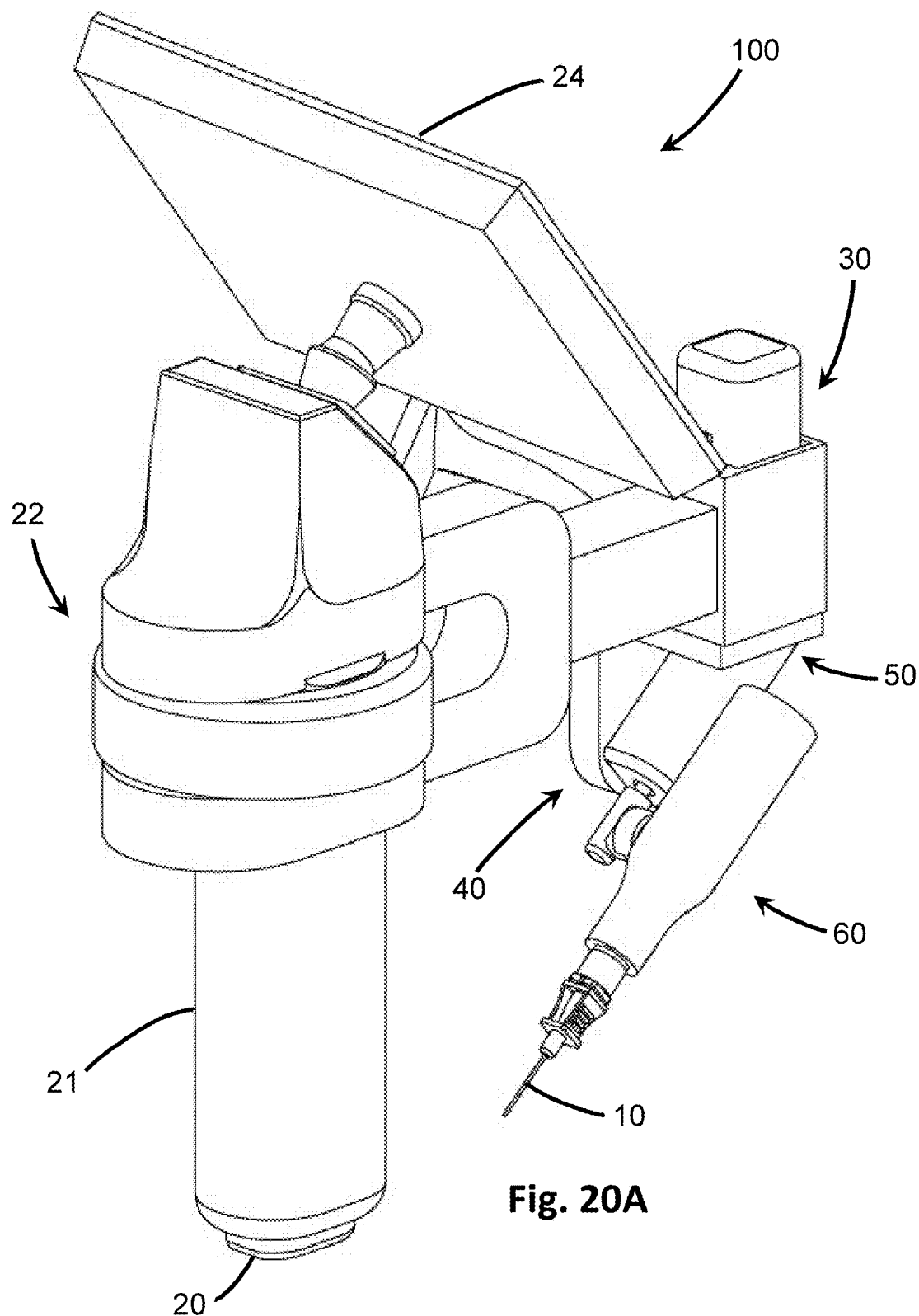
FIG. 20A is a perspective view of another embodiment of the insertion device in which reciprocating motion and the vibrational actuator is inline with the penetrating member.
Figure 20B:
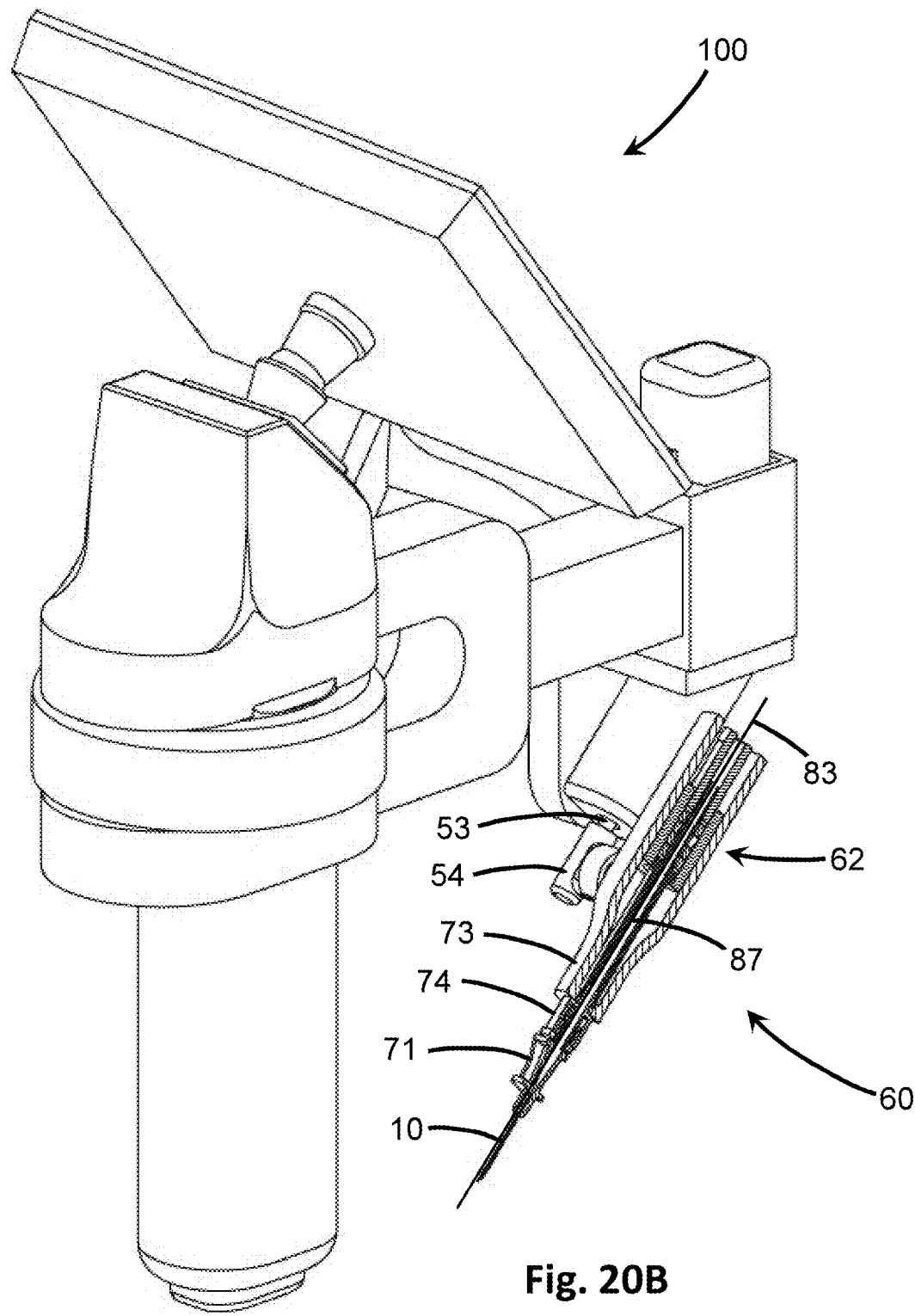
FIG. 20B shows a partial cross-section of the embodiment of FIG. 20A showing a guidewire passing through the vibrational actuator.

In at least one other embodiment, as in FIGS. 20A and 20B, the vibrator 60' and vibrational actuator 62' of the insertion device 100' is coaxial, or inline, with the penetrating member 10. In such embodiments, the drive shaft 68' extends from the vibrational actuator 62' to a portion of the housing 73. The housing 73 may include the vibrational actuator 62' as well, and connects to a hub 71 a distal end where the penetrating member 10 connects. In some embodiments, the housing 73 may further include a neck 74 that extends between the housing 73 and the hub 71, such as if additional space is needed.

Regardless of whether the vibrator 60, 60' is offset or inline with the penetrating member 10, vibration of the penetrating member 10 by the vibrational actuator 62 may be accomplished in a variety of ways, which may be selected based on the type of tissue being penetrated. The particular actuation mechanism useful to overcome the tissue deformation and insertion force depends on the resonance frequency and other electromechanical properties of the system to beneficially interact with the resonance and other mechanical properties of the tissue, vessels or other structures encountered by the advancing tip of the penetrating member 10.

For instance, in at least one embodiment, the vibrational actuator 62 is a piezoelectric motor. Transducer technologies that rely on conventional, single or stacked piezoelectric ceramic assemblies for actuation can be hindered by the maximum strain limit of the piezoelectric materials themselves. Because the maximum strain limit of conventional piezoelectric ceramics is about 0.1% for poly crystalline piezoelectric materials, such as ceramic lead zirconate titanate (PZT) and 0.5% for single crystal piezoelectric materials, it would require a large stack of cells to approach displacement or actuation of several millimeters or even many tens of microns. Using a large stack of cells to actuate components would also require that the medical tool size be increased beyond usable biometric design for handheld instruments.

Flextensional transducer assembly designs have been developed which provide amplification in piezoelectric material stack strain displacement. The flextensional designs com-prise a piezoelectric material transducer driving cell disposed within a frame, platen, endcaps or housing. The geometry of the frame, platen, endcaps or housing provides amplification of the axial or longitudinal motions of the driver cell to obtain a larger displacement of the flextensional assembly in a particular direction. Essentially, the flextensional transducer assembly more efficiently converts strain in one direction into movement (or force) in a second direction.

Therefore, as shown in FIG. 16B, the vibrational actuator 62 is a flextensional transducer which includes a plurality of piezoelectric elements 63 stacked together with electrodes 65 placed between adjacent piezoelectric elements 63. The plurality of piezoelectric elements 63 and electrodes 65 stacked together form a piezoelectric stack 64. An insulator 66 caps the end of the stack 64 to shield the remainder of the device from the energy produced by the piezoelectric elements 63. A rear mass 67 located on the opposite side of the insulator 66 applies tension to the piezoelectric stack 64 and keeps the stack 64 compressed together for increased efficiency. At least the piezoelectric stack 64, and preferably the insulator 66 and rear mass 67 as well, are cylindrical and formed with a hollow bore running through the center. The drive shaft 68 extends through this hollow bore through the vibrational actuator 62. When the electrodes 65 are electrically stimulated, such as when the vibrational actuator 62 receives a signal from the processor 22 to activate, the electrical energy channeled through the electrodes 65 is converted into mechanical vibrational energy by the piezoelectric elements 63, which in turn is transferred to the drive shaft 68 to move the drive shaft 68 in a repetitive, oscillatory motion in the linear direction 61.

A variety of flextensional transducers are contemplated for use as the vibrational actuator 62, 62'. For example, in one embodiment, flextensional transducers are of the cymbal type, as described in U.S. Pat. No. 5,729,077 (Newnham), which is incorporated herein by reference. In another embodiment, flextensional transducers are of the amplified piezoelectric actuator ("APA") type as described in U.S. Pat. No. 6,465,936 (Knowles), which is also incorporated herein by reference. In yet another embodiment, the transducer is a Langevin or bolted dumbbell-type transducer, similar to, but not limited to that which is disclosed in United States Patent Application Publication No. 2007/0063618 A1 (Bromfield), which is also incorporated herein by reference. FIG. 16B shows one particular example implementing a Langevin transducer as the vibrational actuator 62.

In one embodiment, the flextensional transducer assembly may utilize flextensional cymbal transducer technology or in another example, amplified piezoelectric actuator (APA) transducer technology. The flextensional transducer assembly provides for improved amplification and improved performance, which are above that of a conventional handheld device. For example, the amplification may be improved by up to about 50-fold. Additionally, the flextensional transducer assembly enables housing configurations to have a more simplified design and a smaller format. When electrically activated by an external electrical signal source, the vibrational actuator 62, 62' converts the electrical signal into mechanical energy that results in vibratory motion of the penetrating member 10. The oscillations produced by the vibrational actuator 62, 62' are in short increments (such as displacements of up to 1 millimeter) and at such a frequency (such as approximately 125-175 Hz) as to reduce the force necessary for puncturing and sliding through tissue, thereby improving insertion control with less tissue deformation and trauma, ultimately producing a higher vessel penetration/access success rate.

The vibratory motion produced by the vibrational actuator 62, 62' creates waves, which may be sinusoidal waves, square waves, standing waves, saw-tooth waves, or other types of waves in various embodiments. In the case of a Langevin actuator, as in FIG. 16B, the vibratory motion produced by the piezoelectric elements 63 generates a standing wave through the whole assembly. Because at a given frequency, a standing wave is comprised of locations of zero-displacement (node, or zero node) and maximum displacement (anti-node) in a continuous manner, the displacement that results at any point along the vibrational actuator 62 depends on the location where the displacement is to be measured. Therefore, the horn of a Langevin transducer is typically designed with such a length so as to provide the distal end of the horn at an anti-node when the device is operated. In this way, the distal end of the horn experiences a large vibratory displacement in a longitudinal direction 61 with respect to the long axis of the vibrational actuator 62. Conversely, the zero node points are locations best suited for adding port openings or slots so as to make it possible to attach external devices.

In other embodiments, the vibrational actuator 62, 62' may be a voice coil for the driving actuator rather than piezoelectric elements. Voice coil actuator (also referred to as a "voice coil motor") creates low frequency reciprocating motion. The voice coil has a bandwidth of approximately 10-60 Hz and a displacement of up to 10 mm that is dependent upon applied AC voltage. In particular, when an alternating electric current is applied through a conducting coil, the result is a Lorentz Force in a direction defined by a function of the cross-product between the direction of current through the conductive coil and magnetic field vectors of the magnetic member. The force results in a reciprocating motion of the magnetic member relative to the coil support tube which is held in place by the body. With a magnetic member fixed to a driving tube, the driving tube communicates this motion to an extension member, such as a drive shaft 68, which in turn communicates motion to the penetrating member 10. A first attachment point fixes the distal end of the coil support tube to the body. A second attachment point fixes the proximal end of the coil support tube to the body. The magnetic member may be made of s Neodymium-Iron-Boron (NdFeB) composition. However other compositions such as, but not limited to Samarium-Cobalt (SmCo), Alnico (AlNiCoCuFe), Strontium Ferrite (SrFeO), or Barium Ferrite (BaFeO) could be used. Slightly weaker magnets could be more optimal in some embodiments, such as a case where the physical size of the system is relatively small and strong magnets would be too powerful.

The conducting coil may be made of different configurations including but not limited to several layers formed by a single wire, several layers formed of different wires either round or other geometric shapes. In a first embodiment of the conducting coil, a first layer of conductive wire is formed by wrapping the wire in a turn-like and spiral fashion and in a radial direction around the coil-support tube, with each complete revolution forming a turn next to the previous one and down a first longitudinal direction of the coil support tube. After a predetermined number of turns, an additional layer is formed over the first layer by overlapping a first turn of a second layer of the wire over the last turn of the first layer and, while continuing to wrap the wire in the same radial direction as the first layer, forming a second spiral of wiring with at least the same number of turns as the first layer, each turn formed next to the previous one and in a longitudinal direction opposite to that of the direction in which the first layer was formed. Additional layers may be added by overlapping a first turn of each additional layer of the wire over the last turn of a previous layer and, while continuing to wrap the wire in the same radial direction as the previous layer, forming an additional spiral of wiring with at least the same number of turns as the previous layer, each turn formed next to the previous one and in a longitudinal direction opposite to that of the direction in which the previous layer is formed. In an alternative voice coil embodiment, the locations of the magnetic member and conductive coil are switched. In other words, the conductive coil is wrapped around and attached to the driving tube and the magnetic member is located along an outside radius of the coil support tube. An electrical signal is applied at the conductive attachment sites and causes the formation of the Lorentz force to form in an alternating direction that moves the conductive coil and extension member reciprocally along the longitudinal axis of the device. The conductive coils are physically in contact with the driving tube in this embodiment.

In another embodiment, the vibrational actuator 62, 62' employs a dual-coil mechanism in which the magnetic member of the voice-coil is replaced with a second conductive coil. In other words, the second conductive coil is wrapped around and attached to the driving tube and the first conductive coil is located along an outside radius of the coil support tube as before. In a first version, the inner coil conducts direct current DC and the outer coil conducts alternating current AC. In a second version, the inner coil conducts alternating current AC and the outer coil conducts direct current DC. In a third version, both the inner and outer coils conduct alternating current AC. In all of the voice coil actuator configurations described, springs may be used to limit and control certain dynamic aspects of the penetrating member 10.

In still another embodiment, the vibrational actuator 62, 62' is a solenoid actuator. As with the other voice coil embodiments using coils, the basic principle of actuation with a solenoid actuator is caused by a time varying magnetic field created inside a solenoid coil which acts on a set of very strong permanent magnets. The magnets and the entire penetrating member assembly oscillate back and forth through the solenoid coil. Springs absorb and release energy at each cycle, amplifying the vibration seen at the penetrating member 10. The resonant properties of the vibrational actuator 62, 62' can be optimized by magnet selection, number of coil turns in the solenoid, mass of the shaft, and the stiffness of the springs.

While piezoelectric and voice coil mechanisms have been discussed for the vibrational actuator 62, 62', these are not the only approaches to actuating or oscillating the penetrating member 10. Other approaches, such as a rotating motor, could be used for the vibrational actuator 62, 62'. Generally, any type of motor comprising an actuator assembly, further comprising a mass coupled to a piezoelectric material, or a voice coil motor, or solenoid, or any other translational motion device, would also fall within the spirit and scope of the invention.

During use, feedback to track or confirm the vibrating tip of the penetrating member 10 has reached the desired target point 29 location may be obtained in several forms. First, the vibrating tip of the penetrating member 10 may be visualized on the display 24 as its echo is picked up by the detector 20 during ongoing imaging through the insertion process. This can be performed while viewing the image in long-axis view or short-axis view (as in FIG. 5C), or a user may toggle between long and short-axis views as desired to follow the progress of the tip of the penetrating member 10. Second, the appearance of fluid, such as blood, in the penetrating member, also referred to as "flashback," may be detected through mechanisms such as visual identification, change in resistance to a sub-circuit, or change in resonance frequency or phase of the vibrating needle tip, to name but a few. Other methods of confirming the tip of the penetrating member 10 has reached the preselected target point 29 may also be used.

Figure 21A:
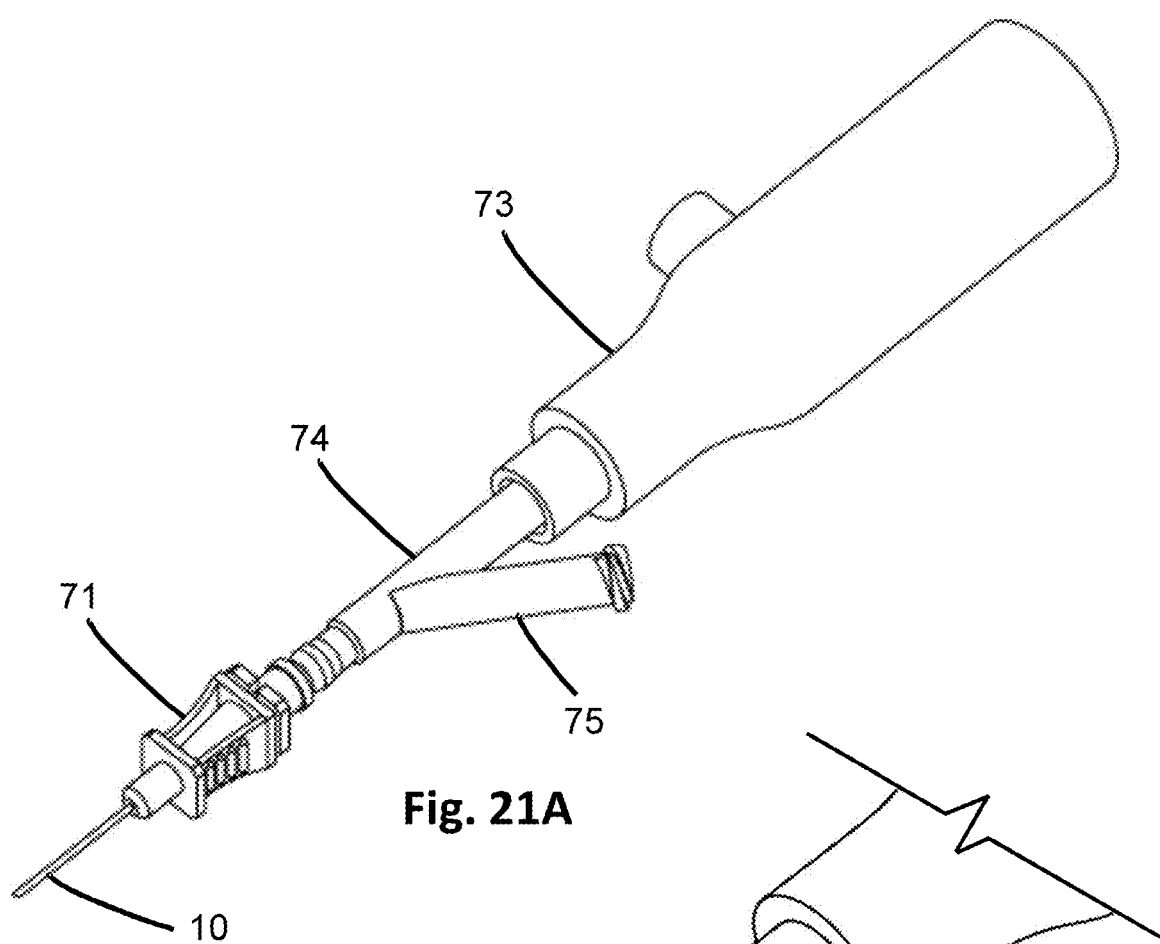
FIG. 21A shows a perspective view of one embodiment of an inline housing having a sideport.
Figure 21B:
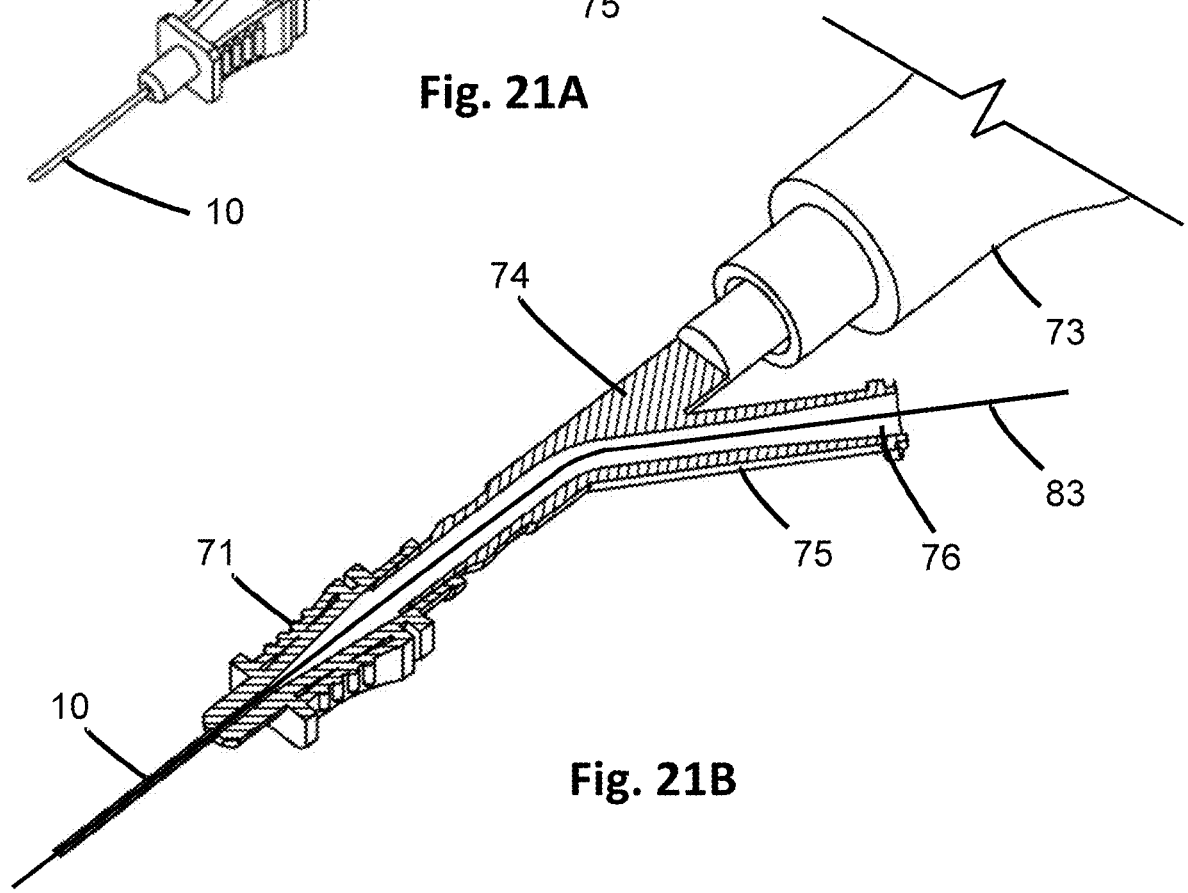
FIG. 21B shows a cross-sectional view of the embodiment of FIG. 21A.
Figure 22:
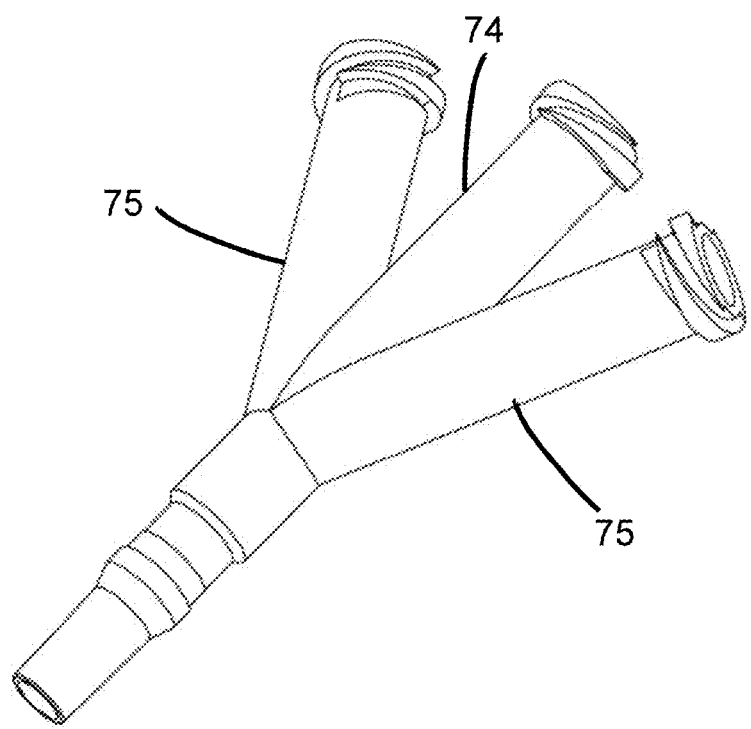
FIG. 22 shows another embodiment of the neck having a plurality of sideports.

After the tip of the penetrating member 10 is successfully inserted in the target vessel and positioned at the desired target point 29, the remainder of the procedure for successful central venous catheterization, discussed above according to the Seldinger technique, could be accomplished. For instance, in one embodiment, a guidewire 83 may be fed through the penetrating member 10 for insertion into the target vessel. The penetrating member 10 may therefore be dimensioned to accommodate a guidewire 83, having an inner diameter at least as large as the diameter of a guidewire 83 which is to be inserted therein. For instance, in some embodiments the penetrating member 10 may be between 14 and 18 gauge, while the outer diameter of the guidewire 75 may range of 0.9 to 0.6 millimeters (0.035-0.024 inches). Of course, other sizes and gauges are also contemplated herein. The guidewire 83 may be extended beyond the tip of the penetrating member 10 by 1-3 cm, although shorter and longer distances for guidewire insertion are also contemplated. For instance, the guidewire 83 may be fed through an interior 72 volume or space of the offset coupler 70 that has an opening in alignment with the hub 71, and therefore, penetrating member 10, as seen in FIG. 16B. In other embodiments, as in FIGS. 21A-22, the guidewire 83 may be fed through a lumen 76 in a side port(s) 75 at the housing 73 of the vibrator 60', such as the neck 74 before the hub 71. The housing 73, neck 74, sideport(s) 75 and hub 71 may all be integrally formed together, or may all be separate components that are selectively attachable to each other, such as with a Luer connection or other suitable selectively removable connection mechanism, or any combination thereof. For instance, in some embodiments, the sideport(s) 75 is integrally formed with the neck 74, which is attachable to the housing 73 on one end and the hub 71 on the opposite end, as shown in FIG. 21B. Accordingly, the neck 74 and sideport 75 may be a Wye adaptor. In other embodiments, the sideport(s) 75 may be separate from and attach to the housing 73 or neck 74. In still other embodiments, the neck 74, sideport(s) 75 and hub 71 may be integrally formed, and connect to the housing 73.

Once the guidewire 83 is inserted through the penetrating member 10 and placed as desired in the target vessel, the penetrating member 10 may then be retracted from the vessel, such as by the extension actuator 52 moving in the reverse direction along the linear direction 51, leaving the guidewire 83 in place. A dilator may also be inserted and retracted as needed to expand the space. A catheter may then be inserted over the guidewire, and the guidewire retracted from the vessel, leaving the catheter in place.

The vertical actuator 32, angular actuator 42, extension actuator 52 and vibrational actuator 62 are integrated in the insertion device 100. Accordingly, in at least one embodiment, the penetrating member 10 may be selectively removable from the insertion device 100, such as by attachment and detachment at the hub 71, so that a sterile penetrating member 10 may be used with each new patient or use. Accordingly, the penetrating member 10 may be disposable and the rest of the insertion device 100, including the detector 20, processor 22, and various actuators 32, 42, 52, 62, all remain intact and are reusable.

In at least one embodiment, at least a portion of, but preferable the entire insertion device 100 up to and including the hub 71 is reusable and may be included in a sterility bag to maintain sterile conditions. In some embodiments, the sterility bag may be wiped down, such as with alcohol or bleach, between patients or uses, such that full sterility measures do not need to be taken on the reusable insertion device 100 between uses every time. In other embodiments, the hub 71 may be removable from the offset coupler 70 or housing 73 for sterilization between uses or disposal. In still other embodiments, the offset coupler 70 or housing 70 may be removable from the remainder of the device 100, 100" for sterilization between uses or disposal. Throughout the various embodiments, it is contemplated that the reusable portions of the insertion device 100, 100" may be encased in a sterility bag or like structure to maintain sterile conditions between use.

In at least one embodiment, as shown in FIGS. 17-19B, the insertion device 100' may include a guidewire adjustment 80 for inserting a guidewire 83 as directed by the processor 22. A guidewire actuator 82 is in electrical communication with the processor 22 and receives operative data from the processor 22 directing activation and operational parameters based on the type of actuator, location of guidewire, etc. For instance, in at least one embodiment shown in FIGS. 18A and 18B, the guidewire actuator 82 is a rotational motor, which may have at least one, but in some instances, two elongate members 85 that extend from the guidewire actuator 82. A gear(s) 84 of the guidewire actuator 82 turns at least one of the elongate member(s) 85. In some embodiments, only one elongate member 85 is active, being primarily engaged by the gear 84 for turning or rotating. Another elongate member 85 may also be present, such as paired with the first active elongate member, but may be passive such that it is not rotated by the guidewire actuator 82. Accordingly, a passive elongate member 85 may only rotate by action in response to movement of a paired active elongate member 85, such as by interdigitation of teeth on coordinating gears 84 between the elongate member 85.

Figure 18A:
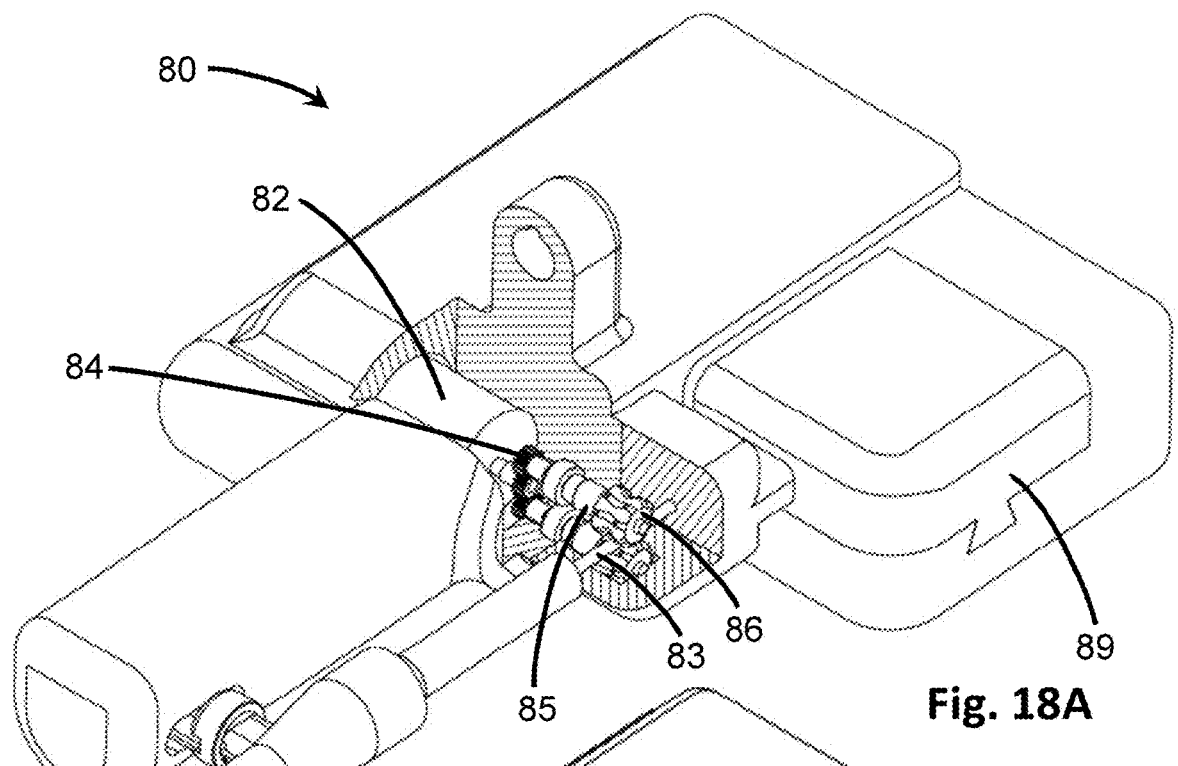
FIG. 18A is a perspective view in partial cut-away of the embodiment of FIG. 17 showing a guidewire actuator for guidewire placement.
Figure 18B:
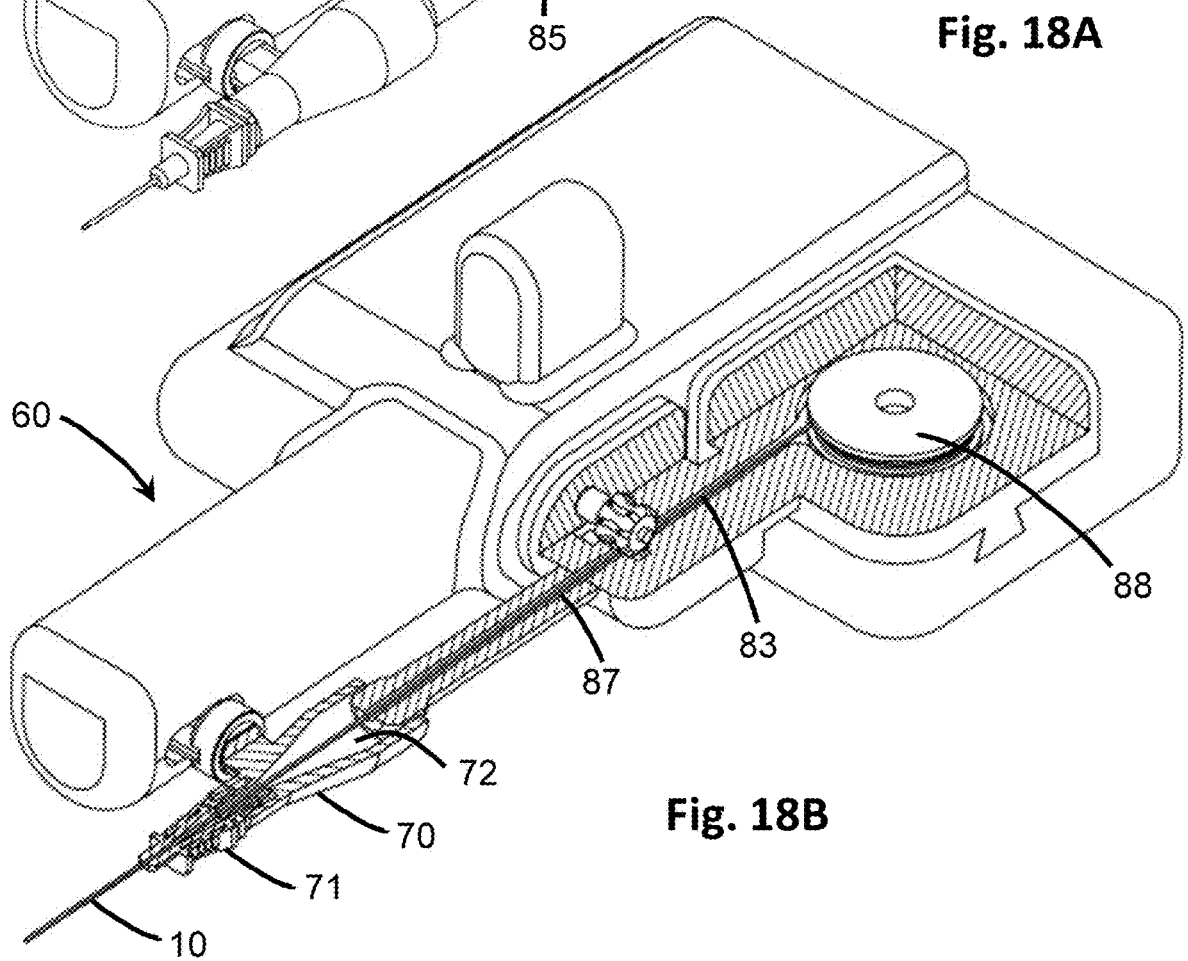
FIG. 18B is a perspective view in partial cut-away of the embodiment of FIG. 17 showing guidewire positioning through the insertion device.

Opposite from the guidewire actuator 82, the elongate member(s) 85 include a frictional member 86. In at least one embodiment, each elongate member 85 includes a frictional member 86, which may be at the terminal end of the elongate member 85. In other embodiments, only the primary elongate member 85 includes a frictional member 86, although preferably both active and passive elongate members 85 include their own respective frictional members 86. In embodiments where there are multiple active elongate members 85, each one includes a frictional member 86. The frictional member(s) 86 grip the guidewire 83 and using frictional engagement, move the guidewire 83 as they rotate. Some embodiments, as shown in FIGS. 18A and 18B, the guidewire 83 may be attached and enclosed in a guidewire housing 89, keeping the guidewire 83 sterile when not in use. In some embodiments, the guidewire 83 is retained as a spool 88 within the housing 89 for compact storage and easy unwinding when needed. In other embodiments, the guidewire 83 may extend out from the insertion device 100' and may be fed through the device 100' as needed. Regardless of whether coiled in a spool or not, as the guidewire actuator 82 turns the elongate member(s) 85, the frictional member(s) 86 engage the guidewire 83 and turn to move the guidewire 83, either advancing or retracting the guidewire, depending on the direction of rotation.

The guidewire 83 is moved through a guidewire channel 87 in the guidewire housing 89. The guidewire channel 87 is aligned with and in fluid communication with the interior 72 of the offset coupler 70, such that the guidewire 83 is advanced through the channel 87, through the interior 72 of the offset coupler 70, hub 71, and penetrating member 10. The guidewire 83 may be advanced beyond the tip of the penetrating member 10, as described previously. The guidewire 83 may be retracted through the same route and mechanism of the insertion device 100', but rotating the elongate member(s) 85 and frictional member(s) 86 in the opposite direction.

Figure 19A:
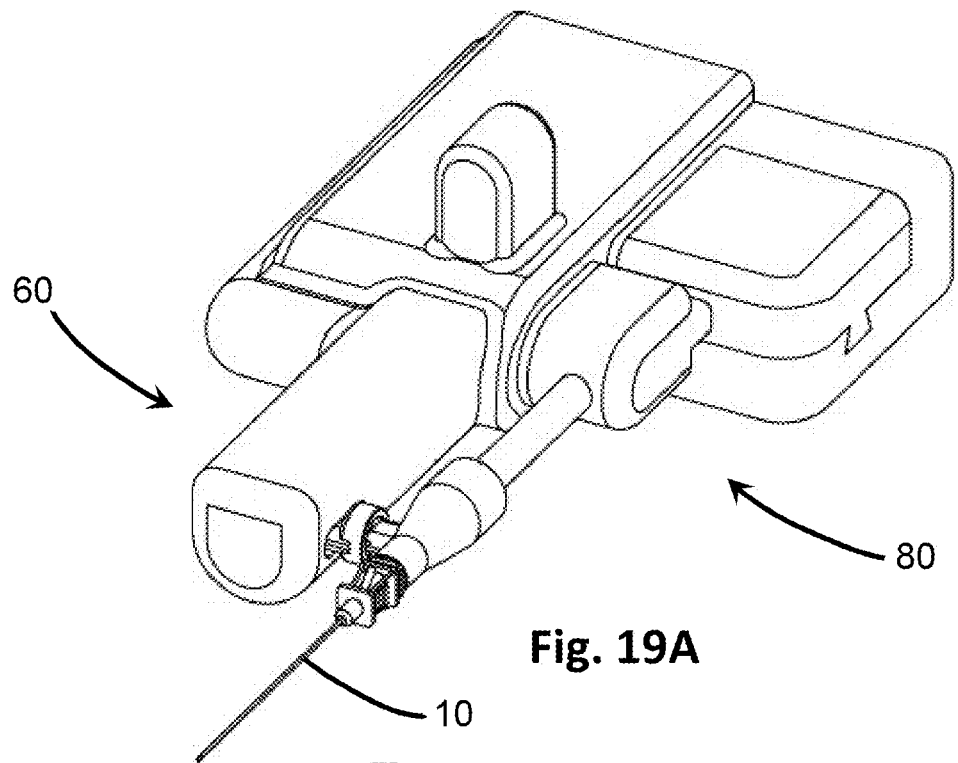
FIG. 19A shows a perspective view of one embodiment of the embodiment of FIG. 17 showing the guidewire housing attached.
Figure 19B:
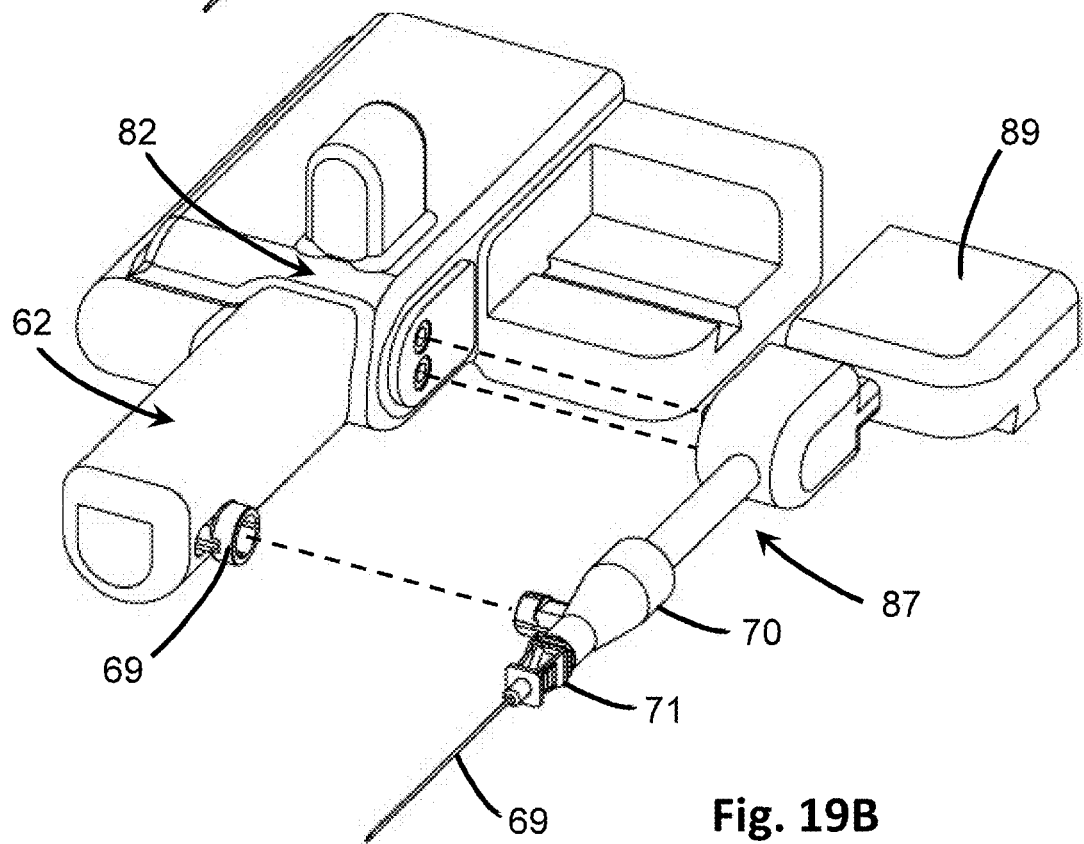
FIG. 19B shows an exploded view of the embodiment of FIG. 19A showing the guidewire housing detached.

The guidewire 83 must also be sterile for use. Accordingly, in some embodiments, such as shown in FIGS. 19A and 19B, anything that the guidewire 83 touches may be selectively detachable and disposable, such as for one-time use. For instance, the guidewire housing 89 containing the spool 88, together with the guidewire channel 87, offset coupler 70, hub 71 and penetrating member 10 may all be separable from the remainder of the insertion device 100', such that the detector 20, processor 22, and actuators 32, 42, 52, 62, and 82 all remain sterile and reusable. This is one benefit to having an offset alignment of the penetrating member 10 from the vibrational actuator 62. In other embodiments, just the guidewire 83 and penetrating member 10 may be removable and disposable, and the guidewire channel 87, offset coupler 70 and hub 71 may be sterilized between uses.

Figure 20C:
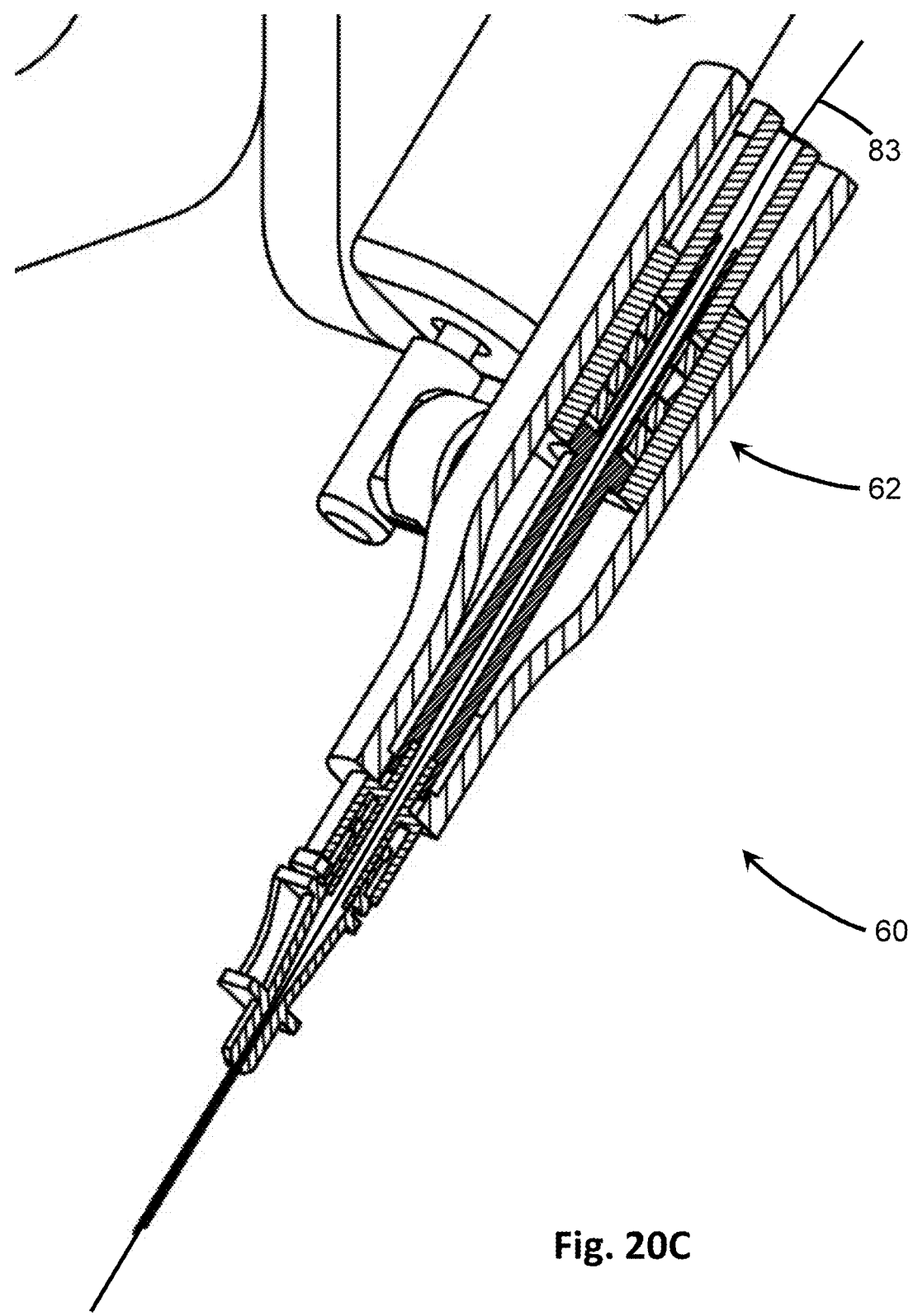
FIG. 20C shows a close-up of the cross-section of FIG. 20B.

In still other embodiments, such as depicted in FIG. 20C, the guidewire 83 passes through the vibrational actuator 62. In such embodiments, the vibrational actuator 62 and the drive shaft 68 may have aligned lumens extending therethrough which act as a guidewire channel 87. The guidewire 83 may be advanced and retracted through these lumens.

ADDITIONAL EMBODIMENTS

FIGS. 23-28 depict further embodiments of an automated insertion device 300 and method 400 of using the same. These embodiments are hand-held devices that can be used to automatically insert a penetrating member 310 such as a needle or catheter into a body cavity such as blood vessels for access to blood and fluid as well as placement of guidewires, dilators, catheters such as CVCs, and the like.

Figure 23:
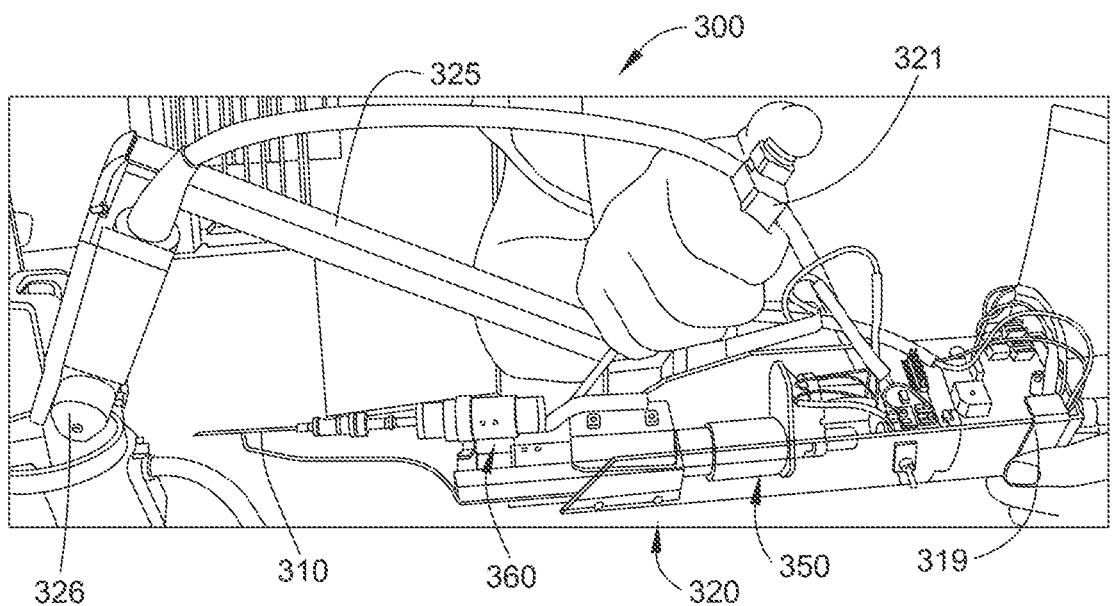
FIG. 23 is a perspective view of another embodiment of the automatic insertion device of the present invention, shown in a retracted position.

As shown in FIG. 23, the insertion device 300 includes a detector 326 to visualize a subcutaneous target site. As with previous embodiments, the detector 326 may be an ultrasound probe capable of using ultrasound to produce images of the target site, though other types of imaging detectors are also contemplated. The detector 326 is in electrical communication with a controller 319 and provides imaging data obtained by the detector 326 to the controller 319. This imaging data may be relayed to a display for viewing by a practitioner or user of the device 300. An arm 325 joins the detector 326 to the remainder of the device 300. A handle 321 that may be gripped by an operator when in use may connect to the arm 325 to enable manipulation of the device 300 to align the detector 326 until the appropriate target site is identified. As used herein, the terms "practitioner," "operator," "user" and other similar terminology may be used interchangeably to refer to a person who uses the device to control the insertion of a penetrating member.

Figure 26:
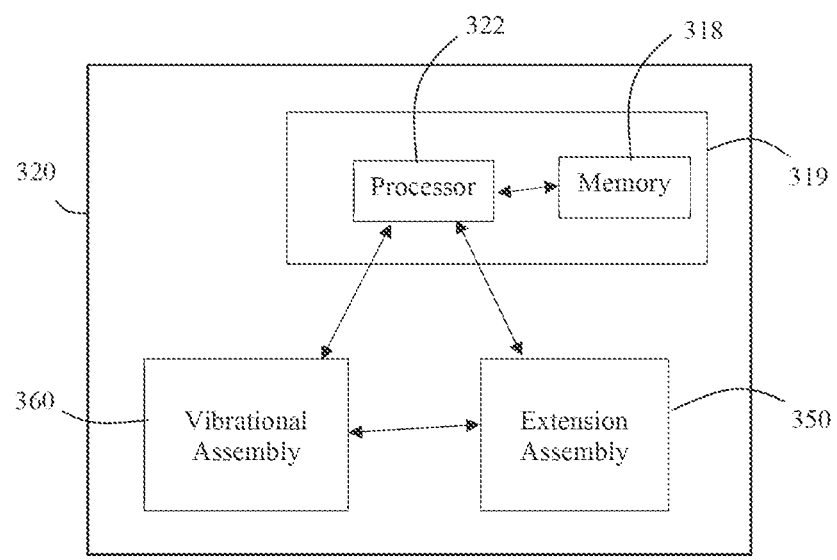
FIG. 26 is a schematic diagram of an embodiment of the automatic insertion device showing the interconnected operation of the extension assembly and vibration assembly.
Figure 27:
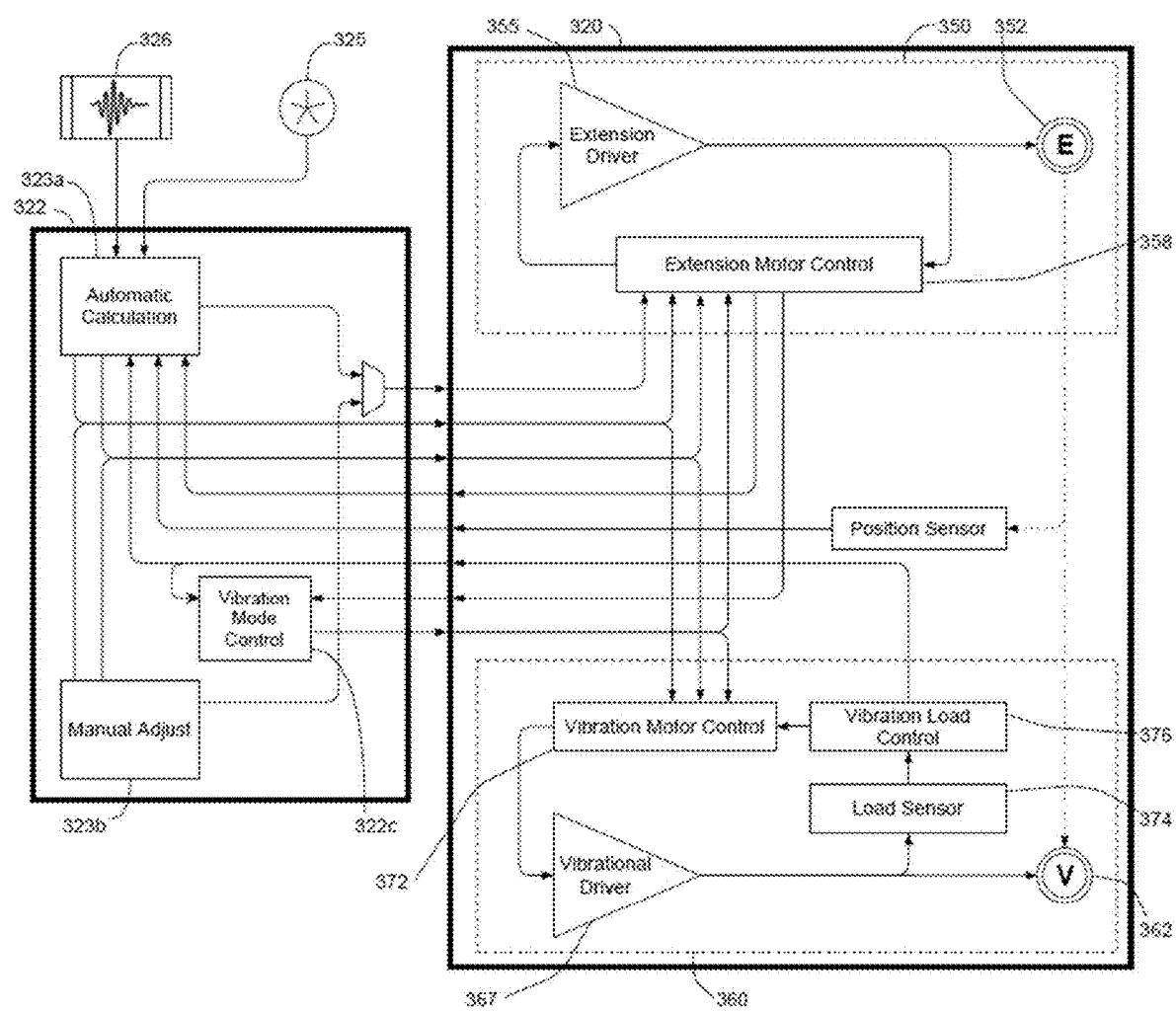
FIG. 27 is an electrical flow diagram showing an embodiment of the operation of the device.
Figure 28:
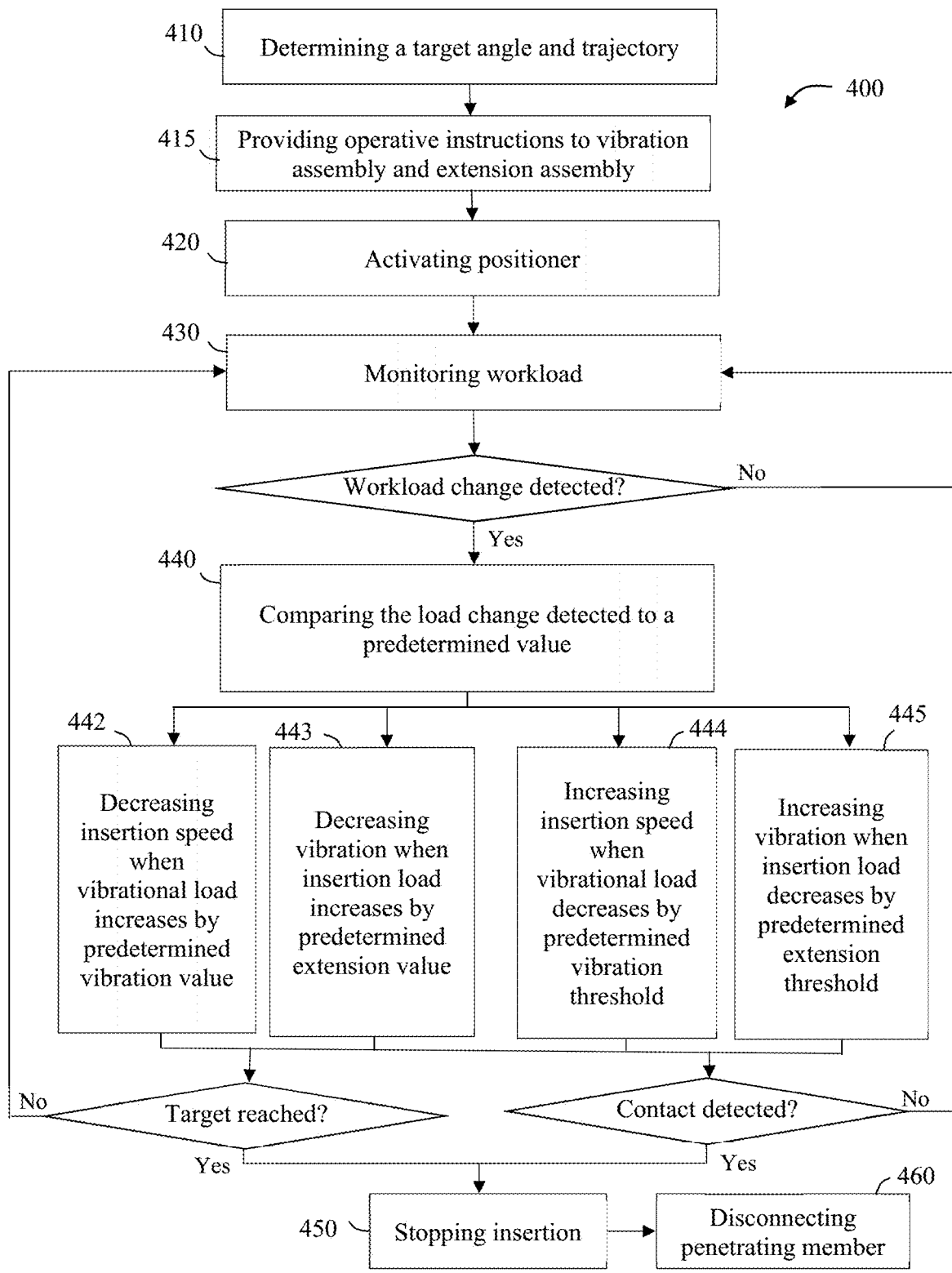
FIG. 28 is a schematic diagram of steps of a method of operating the automatic insertion device.

The controller 319 further includes a processor 322, as shown in FIGS. 26 and 27, that receives the imaging data from the detector 326 and may further process the imaging data, such as by converting the imaging data by automatic calculation 323a into targeting information corresponding to the coordinates of the indicated target site in three-dimensional space, such as an X and Y coordinate solution representative of the depth index of the target site as determined from the imaging data. The processor 322 may be a microprocessor or otherwise as described above. The controller 319 also includes memory 219, shown in FIG. 26, where the imaging data from the detector 326 and targeting information may be saved. The processor 322 further includes capabilities to calculate an insertion angle for the penetrating member 310 to enter the tissue based on the depth and other three-dimensional targeting information. In some embodiments, the processor 322 includes a manual adjust 323b option in which the user may manually adjust the angle of the positioner 320 to optimize the angle of entry for the penetrating member 310.

The detector 326 remains adjacent to the skin surface during use of the device 300. The corresponding imaging data, including depth telemetry and X and Y target coordinates of the target site provided by the detector 326, may vary during the insertion process based upon deformity or movement of the underlying tissue. Imaging data is therefore iteratively collected by the detector 326 at regular intervals, such as every 20 milliseconds in at least one embodiment. Each iterative image data is provided to the processor 322, which then uses the automatic calculation 323a to recalculate and update the targeting information for every iterative packet of image data received to ensure the penetrating member 310 proceeds to the selected and saved target and remains on course.

Figure 24:
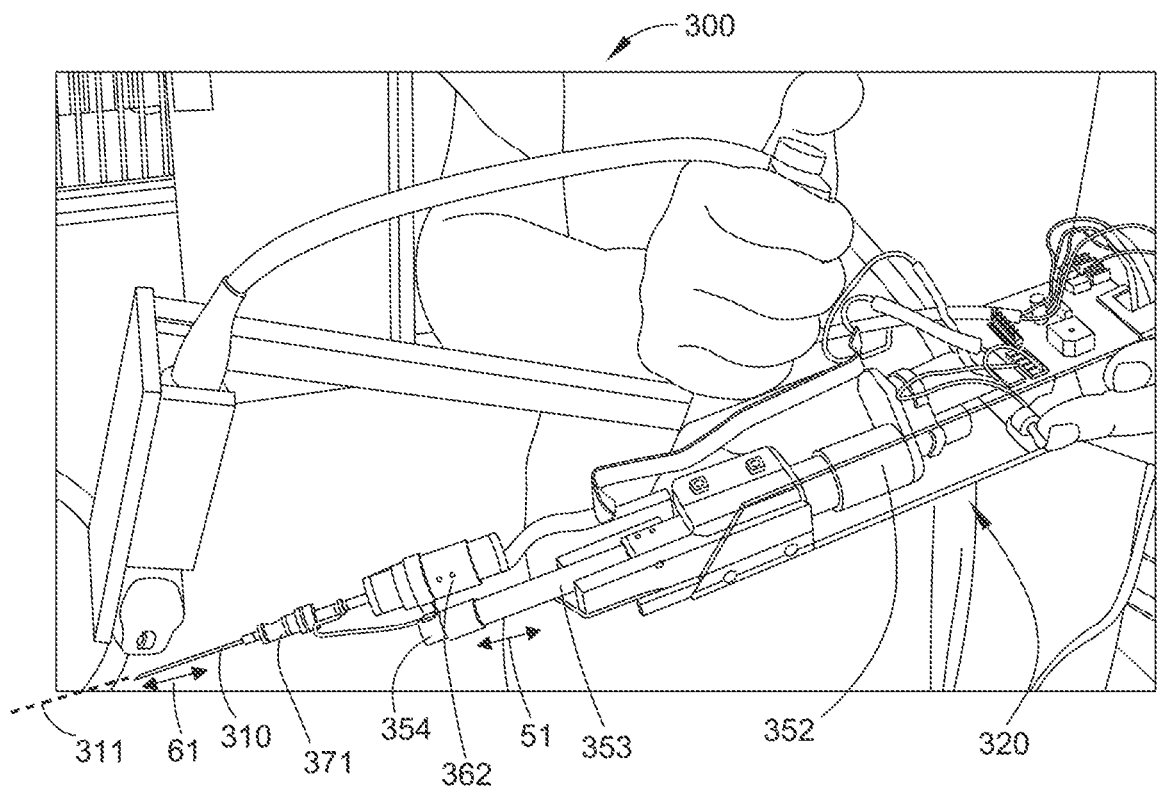
FIG. 24 is a perspective of the insertion device of FIG. 23, shown in an extended position.

As shown in FIG. 24, the device 300 may include a positioner 320 in which the controller 319 may be mounted. The positioner 320 may also carry, house and otherwise include a vibration assembly 360 and extension assembly 350 as discussed below in greater detail. The penetrating member 310 is affixed to the distal end of the vibration assembly 360 and is moved along an insertion axis 311 defined by the targeting information for insertion into the tissue by movement of the extension assembly 350. The positioner 320 may be a platform or housing enclosing the components. In some embodiments, the processor 322 may further provide instructions to the positioner 320 on which the vibration assembly 360 and extension assembly 350 are located to move, such as by rotation to adjust the angle of the penetrating member 310 according to the targeting information discussed above.

The positioner 320 may also include at least one surface proximity sensor 325, depicted schematically in FIG. 27, located preferably at the exterior surface and/or distal surface of the positioner 320 to detect any contact of the positioner 320 with the tissue surface. Such detection may indicate the penetrating member 310 is not long enough to reach the selected targeted site and a different penetrating member 310 may be needed, or that the calculated target information based on the image data needs to be updated to change the angle of insertion to avoid contact of the positioner 320 with the tissue surface. Accordingly, the processor 322 may receive contact information from the surface proximity sensor 325 indicating contact of the positioner 320 with the tissue surface has been made. If such contact information is received, the processor 322 may recalculate the targeting information to avoid further contact. In the absence of contact information from the surface proximity sensor 325, the processor 322 may validate the appropriateness of the targeting information, be it initial targeting information or updated based on iterative imaging data.

The controller 319, and specifically the processor 322, is in electronic communication with a vibration assembly 360 and an extension assembly 350, explained in greater detail below, and is capable of providing instructions such as by transmitting operative instructions based on the targeting information and updated targeting information to the vibration assembly 360 and extension assembly 350.

The device 300 includes a vibration assembly 360, shown in FIGS. 23 and 24, configured to generate oscillations in a longitudinal direction 61 as described above for previous embodiments. It is connected to a penetrating member 310, either directly or through a hub 371 as in FIG. 24, such that vibrations or oscillations generated by the vibration assembly 360 are transferred to the penetrating member 310. The vibration assembly 360 includes a vibrational actuator 362 such as a motor that generates the vibrations or oscillations when activated. As used herein, the terms "vibration" and "oscillation" may be used interchangeably. The vibrational actuator 362 may be any suitable motor, such as but not limited to a voice coil motor (VCM), piezoelectric motor having at least one piezo element therein, and a DC motor. The vibrational actuator 362 is capable of producing vibrations at a rate of 50-50,000 oscillations per second depending on the type of vibrational actuator, frequency and/or input power. In at least one embodiment, the vibration rate may preferably be up to a maximum of about 150 oscillations per second. The vibrations produced can vibrate the penetrating member 310 at amplitudes of about 5 um-1 mm, and preferably 0.5 mm in at least one embodiment.

The vibrational actuator 362 is in electrical communication with the controller 319, and specifically the processor 322, and receives instructions for operation from the controller 319. For instance, the device 300 may include a vibrational power switch 368, shown in FIG. 25, which may be an on-off switch in communication with the controller 319. When activated or switched on, the controller 319 sends a signal to the vibrational actuator 362 to turn on and begin generating vibrations as specified by the controller 319. Vibrations may be stopped by turning the vibrational power switch 368 off. It may also be in direct electrical communication with the vibration actuator 362 in other embodiments, and in some embodiments may be a potentiometer or otherwise have the ability to adjust the power supplied to the vibrational actuator 362 along a continuum rather than on or off.

With reference to FIG. 27 which shows an electrical flow diagram of the device 300, the vibration assembly 360 includes a vibrational control 372 which is an electrical module that determines the relative output level at which the vibrational actuator 362 should operate depending on the signals received from the controller 319, processor 322, vibration control mode 322c (an optional subcomponent of the processor 322) and/or the extension assembly 350 discussed below. The output level of the vibrational actuator 362 is governed by the voltage applied to the actuator and or the drive signal frequency. Instructions may be sent from the controller 319, processor 322 or vibration control mode 322c to the vibrational control 372, which relays the operative instructions to a vibrational driver 367 which sends a signal such as voltage to the vibrational actuator 367 to activate and/or continue operation of the vibrational actuator 367. The vibrational actuator 362 may contain sensors that detect amplitude, power consumption and load experienced by the penetrating member 310 during insertion. This information is relayed to the extension assembly 350, either directly or indirectly through the controller 319 or processor 322, as explained in more detail below.

A vibrational load sensor 374 may be included that detects the load placed on the penetrating member 310 and consequent damping of the vibrations experienced by the penetrating member 310 during insertion. The vibrational actuator 362 operates at a frequency, but this frequency will shift when the connected and vibrating penetrating member 310 engages with tissue because the additional elasticity of the biological tissue increases the stiffness of the combined system (the vibrational actuator 362 plus the tissue). When the vibrating penetrating member 310 engages the tissue, the tissue dampens the amplitude and effectiveness of the vibration. To limit damping the amplitude and effectiveness of the vibration, the frequency/voltage of the drive signal to the vibrational actuator 362 must change. Changing the frequency/voltage of the drive signal requires additional power supplied to the vibrational actuator 362 to limit the damping of the amplitude. The amount of power (such as in watts) supplied to the vibrational actuator 362 is referred to as the vibrational power consumption. Vibrational power consumption may also be detected through voltage sensing elements within the vibration assembly 360 according to the following formula:

$$\text{Power} = I\_rms * V\_rms$$

where I_rms is current and V_rms is voltage. Vibrational power consumption can be determined from the current and voltage measured at the vibrational actuator 362. Therefore, damping of vibration amplitude requires additional power consumption to combat the damping.

The "load" is the axial force applied to the penetrating member 310 in Newtons (N), which can be detected by the vibrational load sensor 374 that measures force. The vibrational load sensor 374 may be a circuit or other suitable mechanism. In one embodiment, the vibrational load sensor 374 may be a shunt resistor and amplifier. In other embodiments, the load and damping on the penetrating member 310 may be mechanically sensed using an LVDT sensor. The vibrational actuator 362 itself may also act as a vibrational load sensor receiving feedback of the force applied to the penetrating member 310 through the coils or magnets within the vibrational actuator 362 also receiving such force. Additionally, the power consumed by the extensional actuator when tougher tissues are encountered by the penetrating needle could likewise modulate based on "load" as defined here. Alternately, the phase relationship between the load current and voltage of the vibrational actuator 362 may be monitored and the effect of damping or load on the penetrating member 310 may be inferred from changes in this phase relationship.

Feedback of the damping on the penetrating member 310 and load current on the vibrational actuator 362 may be sent to a vibration power and load control 376 module which determines the effect of the load and damping experienced by the penetrating member 310 as it relates to the operative parameters of the vibrational actuator 362. The vibration load control 376 may send signals to the vibration motor control 372, processor 322 and/or vibration mode control 322c to adjust the speed of oscillation based on the feedback from the penetrating member 310. It may also send this information to the extension assembly 350, either directly or through the controller 319 and/or processor 322, to adjust the speed of insertion based on the vibrational load experienced by the penetrating member 310 under vibration.

Figure 25:
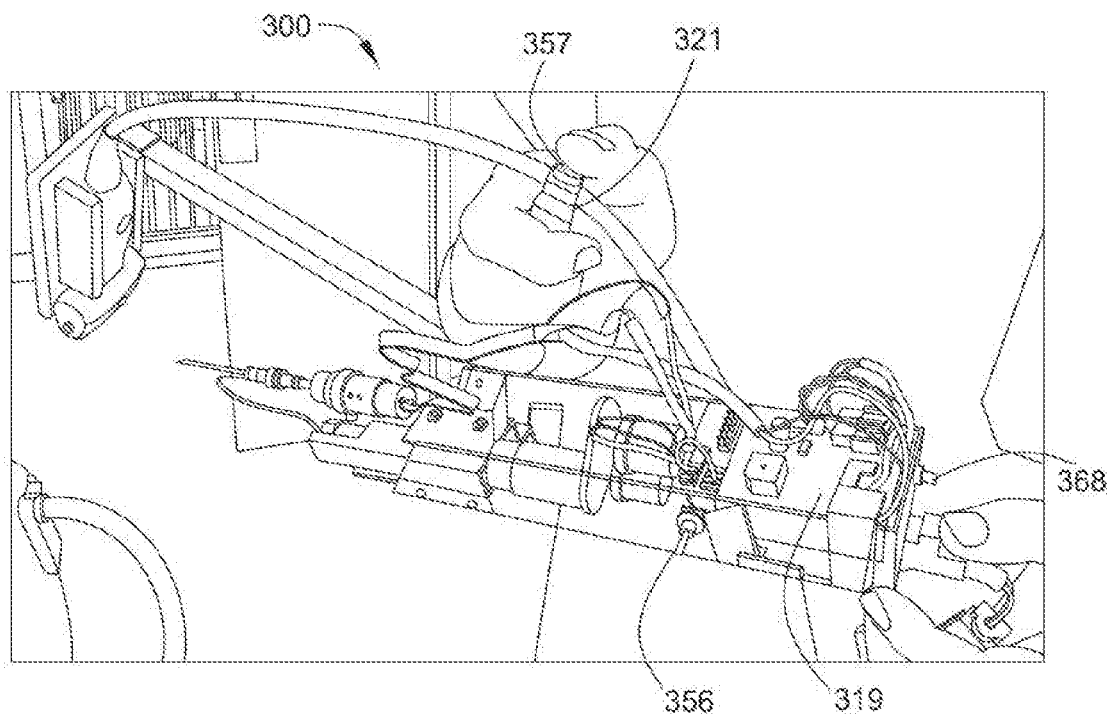
FIG. 25 is a perspective view of the insertion device of FIG. 23, showing the proximal end of the device.

The device 300 also includes an extension assembly 350 as shown throughout the Figures. As discussed above, the extension assembly 350 is configured to move the penetrating member 310 in a linear direction 51 for insertion and retraction of the penetrating member 310. The extension assembly 350 includes an extension actuator 352 that is a motor, such as but not limited to a linear or translational motor and can operate by any suitable mechanism. An extension shaft 353 is mechanically joined to the extension actuator 352 at one location and at another, spaced apart location to the penetrating member 310, hub 371, the vibrational actuator 362 or any other component movable with the penetrating member 310, such as through an extension mount 354 as shown in FIG. 24. The extension shaft 353 is preferably rigid and may extend by telescopic action in at least one embodiment. The extension assembly 350 is in electronic communication with the controller 319 and/or processor 322 to provide and receive operative instructions. For instance, the extension assembly 350 may also include an extender power switch 357, which may be attached anywhere on the device 300 such as to the controller 319, exterior surface of the positioner 320, or to the handle 321 as shown in FIG. 25. The extender power switch 357 can be used to turn the extension assembly 350 on and off. In at least one embodiment, the extender power switch 357 closes a circuit to provide operative power to the extension actuator 352 to move the extension shaft 353 in the linear direction 351. The direction of movement may be controlled by a directional switch 356, shown in FIG. 25, which may also be located anywhere on the device 300. The directional switch 356 may be a switch that can be toggled between a forward direction for advancing the extension shaft 353 for insertion of the penetrating member 310 and a reverse direction for retraction of the extension shaft 353 and removal of the penetrating member 310. A ready or retracted position of the extension assembly 350 is shown in FIG. 23 with the extension shaft 353 fully retracted, and an insertion or deployed position is shown in FIG. 24 with the extension shaft 353 fully extended in the linear direction 51.

The extension actuator 352 is configured to operate at various speeds for inserting the penetrating member 310 at different speeds, depending on the vibrational load and/or damping experienced by the penetrating member 310 during insertion. For instance, in at least one embodiment the extension actuator 352 is operative at a first operative speed in a first mode, a second operative speed in a second mode, and a third operative speed in a third mode. Any number of modes are contemplated each with their own respective operative speed. The operative speeds may be a range or a specific speed, and may be any speed along a continuum of possible speeds based on the capabilities of the particular extension actuator 352 used. For instance, in at least one embodiment, the extension actuator 352 is configured to operate at a first operative speed of about 2.0 cm/s in a first mode, about 1.0 cm/s in a second mode, and 0.5 cm/s in a third mode. The various modes may therefore be used to adjust the speed of insertion depending on what the penetrating member 310 is encountering during insertion. For instance, slower insertion speeds may be used when increased load or vibrational damping is experienced by the penetrating member 310, and faster insertion speeds may be used when less load or vibrational damping is experienced by the penetrating member 310. Any of the operative modes may be set as the default mode at which the extension actuator 352 operates by default unless otherwise determined, as explained below. For instance, the extension actuator 352 may use the first mode with an operational speed of 2.0 cm/s in at least one embodiment and may reduce in insertion speed to compensate for increased vibrational loads experienced during insertion.

Power consumption may also be defined by the power required by the extension motor to continue advancement as different tissues are penetrated by the attached penetrating member 310. This power consumption may be referred to as extension power consumption. The extension actuator 352 may itself be a sensor for how much resistance is being placed on the penetrating member 310 during insertion, such as may occur when denser tissue is encountered, which would increase the extension power consumption on the extension actuator 352 to continue operating at a particular insertion speed. Accordingly, feedback of the extension power consumption and current insertion speed may be sent to the vibrational assembly 360, either directly or indirectly through the controller 319 and/or processor 322, to adjust the vibration based on the extension power load experienced by the penetrating member 310 experienced by the extension actuator 352 during insertion.

The extension assembly 350 also includes electrical circuitry to receive and transmit signals and information with the controller 319, processor 322 and vibration assembly 360. For instance, as shown in FIG. 27, the extension assembly 350 may include an extension motor control 358 that receives operative signals from the controller 319, such as to activate the extender actuator 352 when the extender power switch 357 is activated or to direct which operative mode and speed to use. The definitional parameters for each operative mode and its corresponding speed(s) may be stored in memory 318 within the controller 319 or may be stored in the extension motor control 358 or memory within the extension assembly 350. The extension motor control 358 sends operative instructions to an extension driver 355 that in turn sends signals to the extension actuator 352, such as voltage, to activate the extension actuator 352 and move the penetrating member 310 in the direction indicated by the directional switch 356.

The extension motor control 358 may also receive signals from the vibration assembly 360, such as from the vibration load control 376, regarding the load and damping experienced by the penetrating member 310. This may be in the form of vibrational amplitude and/or motor power consumption changes experienced by the vibrational actuator 362 coupled to the penetrating member 310. Preferably, these signals and/or adjustment occur at regular intervals iteratively throughout the insertion process, such every 20 milliseconds though other time intervals less than the total time for insertion are contemplated.

The speed of the extension actuator 352 may be adjusted by the extension motor control 358 to increase or decrease depending on the vibrational amplitude damping and/or changes in power consumption of the vibrational actuator 362, which results from the load on the penetrating member 310 as it progresses through different tissue types. For instance, when the penetrating member 310 encounters stiffer, harder or more difficult to penetrate tissue, such as tendon, it dampens the vibration imparted to the penetrating member 310 and increases the load on the penetrating member 310 and the power consumption of the vibrating actuator 362 changes and/or greater drive signal (e.g., voltage amplitude) is required to maintain vibrational displacement. When such signals of increased load are sent to the extension assembly 350, the extension actuator 352 slows the insertion speed to accommodate for the increased load. For instance, it may adjust from a first mode to the second mode for a lower speed, or from the second mode to the third mode for a still slower speed, depending on which mode the extension actuator 352 is currently operating in. Conversely, when decreased load is experienced by the penetrating member 310, such as indicating softer tissue is now being encountered, signals of the decreased vibrational load are sent to the extender 352 and the extension actuator 352 is adjusted to a faster operative speed, such as moving from a third mode to the second mode for a faster speed, or from the second mode to the first mode. Whenever a change reaching a predefined threshold is reached, the operative mode of the extension actuator 352 is changed to the next closest mode depending on whether the change reflects increased or decreased load.

The invention also includes a method 400 of using the device 300 described above, shown in FIG. 28. The method 400 first includes determining a target angle and trajectory, as at 410. This may be accomplished by positioning the detector 326 on the skin or other surface of the tissue and using the automatic calculation 323a of the processor 322 to determine the appropriate insertion angle and distance from the current position of the penetrating member 310 to the selected target as previously described. In certain embodiments, it may include determining the target angle based on the manual adjust 323b previously discussed. The selected target site, determined or calculated insertion angle and distance may be stored in the memory 318 of the controller 319.

The method 400 continues with providing operative instructions of vibrational parameters to the vibration assembly 360 and of an insertion speed and distance to the extension assembly 350, as at 415. For the vibration assembly 360, these may include the amplitude, voltage, frequency of vibration, and other parameters as discussed above. For the extension assembly 350, the operative parameters for insertion speed may be the speed corresponding to the default mode. The distance corresponds to the targeting information and trajectory determined based on the imaging information from the detector 326, such as may be determined by the controller 319 and/or processor 322. The operative instructions may be provided to each assembly 350. 360 once the device 300 is turned on or may be stored in the circuitry or memory of the vibration assembly 360 or in the memory of the controller 319.

The method 400 continues with activating the positioner 320, as at 420. This may include turning the power on for the positioner 320, the vibrating actuator 362, and the extension actuator 352. This may occur in stages, each one at a time, or simultaneously. In at least one embodiment, the vibrational actuator 362 is activated prior to the extension actuator 352 so that the penetrating member 310 is vibrating longitudinally before it is advanced for insertion. Once activated, each of the actuators 362, 352 will operate according to their initial or default operative parameters, which may be stored in their respective circuitry such as the vibration control 372 and extension motor control 358, or may be stored and operative instructions provided from the controller 319 and/or processor 322 of the device 300. In at least one embodiment, the extension actuator 352 begins operating in the first mode and the vibrational actuator 362 may operate in a first vibrational mode.

The method 400 includes monitoring the vibrational power consumption and/or vibrational displacement provided by the vibrational actuator 362 and the extension power consumption and/or load on the extension actuator 352, as at 430, such as by detecting the respective workloads continually or iteratively throughout the insertion process. Each iteration of monitoring may occur at any time interval, such as but not limited to 20 milliseconds, depending on how sensitive it is desired for the system to be. It may be accomplished by the vibrational load sensor 374 and the extension actuator 352 or other insertion load sensor as described above. The method then includes comparing the vibrational load detected to a predetermined vibrational value and the insertion load detected to a predetermined extension value, as at 440, and adjusting the insertion speed of the extension actuator 352 if and when a sufficient deviation from the vibrational workload of the vibrational actuator 362 is detected and/or adjusting the vibration of the vibrational actuator 362 if and when a sufficient deviation from the extension workload of the extension actuator 350 is detected. These adjustments may occur by providing a signal to the appropriate vibration assembly 360 and/or extension assembly 350 to make the corresponding adjustment, which may depend on the change in workload detected and whether it exceeds the predetermined values in either a positive or negative direction. For example, the method 400 may include decreasing the insertion speed when the vibrational load of the vibrational actuator 362 increases by a predetermined vibrational threshold, as at 442. For instance, the predetermined vibrational value may be an increase of 30% amplitude and/or 50% power consumption compared to the either the initial starting value or the load sample from the most recent iterative sampling. Similarly, the method 400 may include decreasing the vibration power, amplitude or other operative parameter when the insertion load of the extension actuator 352 increases by a predetermined extension value, as at 443. In some embodiments, the predetermined extension value may be an increase of 0.25×, 0.5×, 1.0×, 1.5×, or 2.0× in power over the initial starting power or the insertion load sample from the most recent iterative sampling. The predetermined vibration and extension values may be different in other embodiments and may depend on a number of factors, including but not limited to the initial starting workload and speed, the tissue(s) being penetrated, the characteristics and type of vibrational actuator 362 and extension actuator 352 used, the amount of initial power supplied and others factors. This reduction in insertion speed may correspond to transitioning from operating the extension actuator 352 from one operative mode to the next available operative mode to adjust the insertion speed, such as moving from a first mode to a second mode, or from a second mode to a third mode, each with decreasing levels of insertion speed. It may also correspond to transitioning the vibrational actuator 362 from one vibrational mode to another. The method 400 contemplates changing the operative parameters of both, just one of, or neither of the vibrational actuator 362 and extension actuator 352 depending on what the loads are on the opposite actuator.

Conversely, the method 400 includes increasing the insertion speed when the vibrational load of the vibrational actuator 362 decreases by a predetermined vibrational value, as at 444, or increasing the vibration of the vibrational actuator 362 when the insertion load on the extension actuator 352 decreases by a predetermined extension value, as at 445. The predetermined vibration value or extension value for increasing insertion speed or vibration may be the same as that for decreasing insertion speed or vibration, respectively. Therefore, the change may also be described as a deviation from the predetermined values, such as a deviation of 30% amplitude and/or 50% power consumption compared to a previous vibrational load sample on the vibrational actuator 362 or a deviation of 0.5× insertion load compared to a previous insertion load on the extension actuator 352. In other embodiments, however, the predetermined vibration and extension values for increasing insertion speed or vibration may be different than that for decreasing insertion speed or vibration. Here again, the increase in insertion speed or vibration may occur by transitioning to the next available operative mode, such as moving from the third mode to the second mode or from the second mode to the third mode for the extension actuator 352, each with increasing insertion speeds. In addition, the sampling rate or interval may continue to be the same as previously, such as every 20 milliseconds, or the sampling rate may change over time. For instance, the sampling interval may become smaller, providing more frequent feedback when the vibrational load increases and may then lengthen, providing less frequent feedback when the vibrational load decreases, or vice versa. In at least one embodiment, the sampling rate or interval may remain constant throughout the insertion process.

Monitoring the vibrational workload, as at 430, continues throughout the insertion process, with adjustments made to increase or decrease insertion speed or vibration, preferably in a stepwise fashion between operative modes of the extension actuator 352 and vibrational actuator 362, throughout the insertion process as needed based on what loads the other actuator is experiencing.

The method 400 concludes by stopping insertion, as at 450, which may occur a number of ways, for instance, automatically when the preselected target is reached according to the calculated or determined trajectory based on the imaging information. Achieving the target site may be confirmed by the presence of an appropriate volume of blood or fluid escaping from the target, indicating the distal tip of the penetrating member 310 is located within the interior volume of a blood vessel. Stopping insertion, as at 450, may also occur in the event contact of the device 300 with the surface of the tissue is detected, such as by the surface proximity sensor 325 discussed above. In this event, the vibrational actuator 362 may will concurrently suspend vibration and the extension actuator 352 may reverse and retract the penetrating member 310. The positioner 320 may also inform the operator that the length of the penetrating member 310 is insufficient for the intended target depth, such as by a light, sound or other indicator observable to the operator.

When insertion of the penetrating member 310 stops, active operations of the vibrational actuator 362 and extension actuator 352 are suspended by the processor 322. Upon confirmation of successful introduction of the penetrating member 310 to the intended target, such as by the appearance of blood or other bodily fluid appropriate for the tissue penetrated, the interior of the target site may be access for extracting or inserting materials through the penetrating member 310. For instance, blood may be collected, drugs or solutions may be applied, and/or a flexible guide wire may be inserted through hollow interior of the penetrating member 310. The penetrating member 310 still resident within the target site may be disconnected from the device, as at 460, such as by detaching from the vibration assembly 360 at the hub 371. The hub 371 may then be used as a connection point for a syringe or vial for blood collection or drug/solution delivery, or as a connection point for an IV system. A guidewire may be inserted through the penetrating member 310 before or after disconnection from the remainder of the insertion device 300. If the guidewire is inserted through the penetrating member 310 while still connected to the device 300, the positioner 320 with attached penetrating member 310 and the remainder of the device 300 may be gently withdrawn over the flexible guide wire from the tissue until the operator can appreciate evidence of the flexible guide wire extending from the skin surface, at which point the operator can safely disassociate the positioner 320 and penetrating member 310 from interaction with the flexible guide wire.

Since many modifications, variations and changes in detail can be made to the described preferred embodiments, it is intended that all matters in the foregoing description and shown in the accompanying drawings be interpreted as illustrative and not in a limiting sense. Thus, the scope of the invention should be determined by the appended claims and their legal equivalents. Now that the invention has been described,

What is claimed is:
1. A method for automatically inserting a penetrating member into tissue, the method comprising:
providing a device having a detector, a vibrational actuator and an extension actuator;
determining a target site within the tissue for the penetrating member to be inserted;
obtaining imaging data of the target site with the detector;
determining targeting information of at least an insertion distance for the penetrating member to reach the determined target site based on the imaging data;
providing operative instructions of vibrational parameters to the vibrational actuator and of an insertion speed and distance to the extension actuator based on the targeting information;
activating the vibrational actuator to initiate vibration and the extension actuator to initiate insertion of the penetrating member into the tissue according to the operative instructions;
detecting a vibrational load on the vibrational actuator and an insertion load on the extension actuator;
comparing the detected vibrational load to a predetermined vibrational value and the detected insertion load to a predetermined extension value; and
adjusting the insertion speed of the extension actuator when the detected vibrational load deviates from the predetermined vibrational value and adjusting the vibration of the vibrational actuator when the detected insertion load deviates from the predetermined extension value;
wherein adjusting the insertion speed further comprises one of: (a) decreasing the insertion speed when the detected vibrational load on the vibrational actuator increases above the predetermined vibrational value, and (b) increasing the insertion speed when the detected vibrational load on the vibrational actuator decreases below the predetermined vibrational value;

wherein the predetermined vibrational value is at least one of a percentage amount of amplitude and a percentage amount of power consumption of the vibrational actuator; and wherein the predetermined vibrational value is at least one of 30% amplitude and 50% power consumption.

2. The method as recited in claim 1, wherein adjusting the vibration further comprises one of:

(a) increasing one of the power, amplitude and frequency of the vibrational actuator when the detected insertion load on the extension actuator decreases below the predetermined extension value, and (b) decreasing one of the power, amplitude and frequency of the vibrational actuator when the detected insertion load on the extension actuator increases above the predetermined extension value.

3. The method as recited in claim 2, wherein the predetermined extension value is one of 0.25×, 0.5×, 1.0×, 1.5×, and 2.0× power of said extension actuator.

4. The method as recited in claim 1, further comprising monitoring the vibrational load on the vibrational actuator and the insertion load on the extension actuator by iterative detection, and wherein comparing the detected vibrational and insertion loads to the predetermined vibrational and extension values respectively occurs with each iterative detection.

5. The method as recited in claim 1, further comprising stopping the insertion of the penetrating member at an earlier occurrence of: (a) traversing the full predetermined distance to reach the determined target site, and (b) detecting contact with a surface of the tissue by a component of the device other than the penetrating member.

6. The method as recited in claim 1, further comprising inserting a guidewire through the penetrating member once the determined target site is reached.

7. The method as recited in claim 1, further comprising disconnecting the penetrating member from the device.

8. A method for automatically inserting a penetrating member into tissue, the method comprising:

providing a device having a detector, a vibrational actuator and an extension actuator;

determining a target site within the tissue for the penetrating member to be inserted;

obtaining imaging data of the target site with the detector;

determining targeting information of at least an insertion distance for the penetrating member to reach the determined target site based on the imaging data;

providing operative instructions of vibrational parameters to the vibrational actuator and of an insertion speed and distance to the extension actuator based on the targeting information;

activating the vibrational actuator to initiate vibration and the extension actuator to initiate insertion of the penetrating member into the tissue according to the operative instructions;

detecting a vibrational load on the vibrational actuator and an insertion load on the extension actuator;

comparing the detected vibrational load to a predetermined vibrational value and the detected insertion load to a predetermined extension value; and adjusting the insertion speed of the extension actuator when the detected vibrational load deviates from the predetermined vibrational value and adjusting the vibration of the vibrational actuator when the detected insertion load deviates from the predetermined extension value;

wherein adjusting the vibration further comprises one of:

(a) increasing one of the power, amplitude and frequency of the vibrational actuator when the detected insertion load on the extension actuator decreases below the predetermined extension value, and (b) decreasing one of the power, amplitude and frequency of the vibrational actuator when the detected insertion load on the extension actuator increases above the predetermined extension value; and wherein the predetermined extension value is one of 0.25×, 0.5×, 1.0×, 1.5×, and 2.0× power of said extension actuator.

9. The method as recited in claim 8, wherein adjusting the insertion speed further comprises one of: (a) decreasing the insertion speed when the detected vibrational load on the vibrational actuator increases above the predetermined vibrational value, and (b) increasing the insertion speed when the detected vibrational load on the vibrational actuator decreases below the predetermined vibrational value.

10. The method as recited in claim 9, wherein the predetermined vibrational value is at least one of a percentage amount of amplitude and a percentage amount of power consumption of the vibrational actuator.

11. The method as recited in claim 10, wherein the predetermined vibrational value is at least one of 30% amplitude and 50% power consumption.

12. The method as recited in claim 8, further comprising monitoring the vibrational load on the vibrational actuator and the insertion load on the extension actuator by iterative detection, and wherein comparing the detected vibrational and insertion loads to the predetermined vibrational and extension values respectively occurs with each iterative detection.

13. The method as recited in claim 8, further comprising stopping the insertion of the penetrating member at an earlier occurrence of: (a) traversing the predetermined distance to reach the determined target site, and (b) detecting contact with a surface of the tissue by a component of the device other than the penetrating member.

14. The method as recited in claim 8, further comprising inserting a guidewire through the penetrating member once the determined target site is reached.

15. The method as recited in claim 8, further comprising disconnecting the penetrating member from the device.

* * * * *